United States Patent
Kayyali et al.

(10) Patent No.: US 11,857,333 B1
(45) Date of Patent: *Jan. 2, 2024

(54) INTEGRATED SLEEP DIAGNOSTIC AND THERAPEUTIC SYSTEM AND METHOD

(71) Applicants: Hani Kayyali, Shaker Heights, OH (US); Dan Bishop, Tallmadge, OH (US); Brian M. Kolkowski, Leroy, OH (US)

(72) Inventors: Hani Kayyali, Shaker Heights, OH (US); Dan Bishop, Tallmadge, OH (US); Brian M. Kolkowski, Leroy, OH (US)

(73) Assignee: Cleveland Medical Devices Inc., Cleveland, OH (US)

( * ) Notice: Subject to any disclaimer, the term of this patent is extended or adjusted under 35 U.S.C. 154(b) by 1801 days.

This patent is subject to a terminal disclaimer.

(21) Appl. No.: 15/641,715

(22) Filed: Jul. 5, 2017

Related U.S. Application Data

(63) Continuation of application No. 13/074,901, filed on Mar. 29, 2011, now Pat. No. 9,730,632, which is a
(Continued)

(51) Int. Cl.
*A61B 5/02* (2006.01)
*A61B 5/08* (2006.01)
(Continued)

(52) U.S. Cl.
CPC ............ *A61B 5/4818* (2013.01); *A61B 5/08* (2013.01); *A61B 5/4836* (2013.01); *A61M 16/00* (2013.01); *A61M 16/0003* (2014.02); *A61B 5/02* (2013.01)

(58) Field of Classification Search
CPC . A61M 16/00; A61M 16/0003; A61B 5/4818; A61B 5/4836; A61B 5/08; A61B 5/02
(Continued)

(56) References Cited

U.S. PATENT DOCUMENTS 5,237,990 A 8/1993 Psaros et al.
5,353,788 A 10/1994 Miles
(Continued)

FOREIGN PATENT DOCUMENTS

WO 2002078775 A2 10/2002
WO 2005028029 A2 3/2005
WO 2005096737 A2 10/2005

OTHER PUBLICATIONS

Jasemian et al., Evaluation of realtime, remote monitoring telemedicine system using the Bluetooth protocol and a mobile phone network, Journal of Telemedicine and Telecare 2005, vol. 11, Issue 5, at 256.
(Continued)

*Primary Examiner* — Navin Natnithithadha
(74) *Attorney, Agent, or Firm* — Brian Kolkowski

(57) ABSTRACT

The present invention relates to an integrated sleep diagnosis and treatment device, and more particularly to an integrated apnea diagnosis and treatment device. The present invention additionally relates to methods of sleep diagnosis and treatment. The sleep disorder treatment system of the present invention can use a diagnosis device to perform various forms of analysis to determine or diagnose a subject's sleeping disorder or symptoms of a subject's sleep disorder, and using this analysis or diagnosis can with or in some embodiments without human intervention treat the subject either physically or chemically to improve the sleeping disorder or the symptoms of the sleeping disorder. The diagnostic part of the system can use many different types of sensors and methods for diagnosing the severity of the symptoms of or the sleep disorder itself. The treatment part of the system can use a device to physically or chemically treat the subject's symptoms or sleep disorder itself.

29 Claims, 15 Drawing Sheets

Related U.S. Application Data continuation of application No. 11/879,934, filed on Jul. 19, 2007, now Pat. No. 7,942,824, which is a continuation-in-part of application No. 11/266,899, filed on Nov. 4, 2005, now Pat. No. 8,172,766.

(51) Int. Cl.
*A61B 5/00* (2006.01)
*A61M 16/00* (2006.01)

(58) Field of Classification Search
USPC .......................... 128/204.23; 600/529–543
See application file for complete search history.

(56) References Cited

U.S. PATENT DOCUMENTS

| | | | |
|---|---|---|---|
| 5,645,043 A | 7/1997 | Long et al. | |
| 5,704,345 A | 1/1998 | Berthon-Jones | |
| 5,803,078 A | 9/1998 | Brauner | |
| 5,953,713 A * | 9/1999 | Behbehani | A61M 16/026 706/16 |
| 5,961,447 A | 10/1999 | Raviv et al. | |
| 6,029,664 A | 2/2000 | Zdrojkowski et al. | |
| 6,138,675 A | 10/2000 | Berthon-Jones | |
| 6,152,129 A | 11/2000 | Berthon-Jones | |
| 6,167,258 A | 12/2000 | Schmidt et al. | |
| 6,229,581 B1 | 5/2001 | Yamamoto et al. | |
| 6,287,264 B1 | 9/2001 | Hoffman | |
| 6,299,581 B1 * | 10/2001 | Rapoport | A61B 5/0002 128/204.21 |
| 6,336,454 B1 | 1/2002 | Farrell et al. | |
| 6,349,724 B1 * | 2/2002 | Burton | F04D 25/166 128/204.18 |
| 6,431,171 B1 | 8/2002 | Burton et al. | |
| 6,475,153 B1 | 11/2002 | Khair et al. | |
| 6,532,957 B2 | 3/2003 | Berthon-Jones | |
| 6,532,959 B1 | 3/2003 | Berthon-Jones | |
| 6,533,729 B1 | 3/2003 | Khair et al. | |
| 6,551,252 B2 | 4/2003 | Sackner et al. | |
| 6,752,766 B2 * | 6/2004 | Kowallik | A61M 16/0051 600/538 |
| 6,832,609 B2 | 12/2004 | Wright et al. | |
| 6,889,691 B2 | 5/2005 | Eklund et al. | |
| 7,018,341 B2 | 3/2006 | Wright et al. | |
| 7,101,341 B2 * | 9/2006 | Tsukashima | A61B 5/083 422/84 |
| 7,190,995 B2 | 3/2007 | Chervin et al. | |
| 7,195,013 B2 | 3/2007 | Lurie | |
| 7,204,250 B1 | 4/2007 | Burton | |
| 7,225,809 B1 | 6/2007 | Bowen et al. | |
| 7,309,314 B2 | 12/2007 | Grant et al. | |
| 7,575,005 B2 | 8/2009 | Mumford et al. | |
| 7,662,101 B2 | 2/2010 | Lee et al. | |
| 7,668,579 B2 | 2/2010 | Lynn | |
| 7,670,295 B2 | 3/2010 | Sackner et al. | |
| 7,757,690 B2 | 7/2010 | Stahmann et al. | |
| 7,878,198 B2 | 2/2011 | Farrell et al. | |
| 7,942,824 B1 | 5/2011 | Kayyali et al. | |
| 8,069,852 B2 | 12/2011 | Burton et al. | |
| 8,172,766 B1 | 5/2012 | Kayyali et al. | |
| 8,308,641 B2 | 11/2012 | Moroney, III et al. | |
| 8,356,594 B2 | 1/2013 | Ujhazy et al. | |
| 8,365,730 B2 | 2/2013 | Baker, Jr. et al. | |
| 8,545,416 B1 | 10/2013 | Kayyali et al. | |
| 9,533,114 B1 | 1/2017 | Kayyali et al. | |
| 10,076,269 B1 | 9/2018 | Kayyali et al. | |
| 10,543,328 B1 | 1/2020 | Kayyali et al. | |
| 2001/0018557 A1 | 8/2001 | Lynn et al. | |
| 2002/0022973 A1 | 2/2002 | Sun et al. | |
| 2002/0032386 A1 | 3/2002 | Sackner et al. | |
| 2002/0165462 A1 | 11/2002 | Westbrook et al. | |
| 2002/0185130 A1 | 12/2002 | Wright et al. | |
| 2003/0000528 A1 | 1/2003 | Eklund et al. | |
| 2003/0135127 A1 | 7/2003 | Sackner et al. | |
| 2003/0183226 A1 * | 10/2003 | Brand | A61M 16/161 128/200.23 |
| 2003/0213489 A1 | 11/2003 | Mechlenberg et al. | |
| 2003/0236450 A1 | 12/2003 | Kocinski | |
| 2004/0073098 A1 * | 4/2004 | Geva | A61B 5/24 600/300 |
| 2004/0116784 A1 | 6/2004 | Gavish | |
| 2004/0138576 A1 | 7/2004 | Wright et al. | |
| 2004/0163648 A1 | 8/2004 | Burton | |
| 2004/0200474 A1 | 10/2004 | Lurie | |
| 2004/0210153 A1 | 12/2004 | Tsukashima et al. | |
| 2004/0254493 A1 | 12/2004 | Chervin et al. | |
| 2005/0081847 A1 | 4/2005 | Lee et al. | |
| 2005/0085738 A1 | 4/2005 | Stahmann et al. | |
| 2005/0115561 A1 * | 6/2005 | Stahmann | A61N 1/3627 128/200.24 |
| 2005/0119586 A1 * | 6/2005 | Coyle | A61B 5/4818 600/538 |
| 2005/0165323 A1 | 7/2005 | Montgomery et al. | |
| 2005/0188991 A1 | 9/2005 | Sun et al. | |
| 2005/0197588 A1 * | 9/2005 | Freeberg | A61N 1/3601 600/529 |
| 2005/0211249 A1 | 9/2005 | Wagner et al. | |
| 2005/0217674 A1 | 10/2005 | Burton et al. | |
| 2005/0222502 A1 * | 10/2005 | Cooper | A61B 5/1495 600/323 |
| 2005/0239838 A1 | 10/2005 | Edgar et al. | |
| 2005/0268916 A1 | 12/2005 | Mumford et al. | |
| 2006/0042627 A1 | 3/2006 | MacMillan et al. | |
| 2006/0070624 A1 | 4/2006 | Kane et al. | |
| 2006/0084877 A1 | 4/2006 | Ujhazy et al. | |
| 2006/0135878 A1 | 6/2006 | Wright et al. | |
| 2006/0247546 A1 | 11/2006 | Imose | |
| 2007/0135724 A1 | 6/2007 | Ujhazy et al. | |
| 2007/0161913 A1 | 7/2007 | Farrell et al. | |
| 2007/0209662 A1 | 9/2007 | Bowen et al. | |
| 2008/0066753 A1 | 3/2008 | Martin et al. | |
| 2008/0257349 A1 | 10/2008 | Hedner et al. | |
| 2008/0269583 A1 | 10/2008 | Reisfeld | |
| 2008/0276939 A1 | 11/2008 | Tiedje | |
| 2010/0043795 A1 | 2/2010 | Ujhazy et al. | |
| 2010/0258126 A1 | 10/2010 | Ujhazy et al. | |
| 2013/0331726 A1 * | 12/2013 | Weber | A61M 16/06 600/538 |

OTHER PUBLICATIONS

Woodward et al., Wireless Telemedicine: The Next Step, 4th Int'l IEEE EMBS Special Topic Conference on Information Technology Applications in Biomedicine, 2003, at 43.

Rasid et al., Bluetooth Telemedicine Processor for Multichannel Biomedical Signal Transmission via Mobile Cellular Networks, IEEE Transactions on Information Technology in Biomedicine, vol. 9, No. 1, Mar. 2005, at 35.

Mohd Fadlee A Rasid, Multi-Channel GPRS-Based Mobile Telemedicine System With Bluetooth and J2ME Interfaces, Doctoral Thesis, Department of Electronic and Electrical Engineering, Loughborough University (Oct. 2005).

D. Alan Lankford, Wireless CPAP Patient Monitoring: Accuracy Study, Telemedicine Journal and e-Health, vol. 10, No. 2, 2004, at 162.

R. Paradiso, et al., Wearable Health Care System for Vital Signs Monitoring, 4thAnnual IEEE Conf. on Information Technology Applications in Biomedicine, 2003, at 283.

M. J. Moron, E. Casilari, R. Luque and J. A. Gazquez, A wireless monitoring system for pulse-oximetry sensors, 2005 Systems Communications (ICW'05, ICHSN'05, ICMCS'05, SENET'05), 2005, at 79-84.

Guilleminault C, van den Hoed J, and Mitler MM, Clinical overview of the sleep apnea syndromes. In: C Guilleminault and WC Dement (Eds), Sleep Apnea Syndromes, Alan R Liss, New York, 1978, pp. 1-12.

Christian Guilleminault and Vivien C. Abad, Obstructive sleep apnea syndromes, Med. Clin. N. Am. 88, 2004, pp. 611-630.

(56) References Cited

OTHER PUBLICATIONS

Francoise J. Roux and Janet Hilbert, Continuous positive airway pressure: new generations, Clin. Chest Med. 24, 2003, at 315-342.
The AASM Manual for the Scoring of Sleep and Associated Events, 2007.
Kirianaki, et al., Data Acquisition and Signal Processing for Smart Sensors, 2002, John Wiley & Sons Ltd.
Elena, et al., Design of a Mobile Telecardiology System Using GPRS/GSM Technology, Engineering in Medicine and Biology, 2002, Departamento Ingeniería Electrónica, Escuela Superior Ingenieros.
ResMed AutoSet T Service Manual.
ResMed AutoSet Spirit Service Manual 1.
ResMed AutoSet Spirit Service Manual 2.
ResMed AutoSet Spirit Service Manual 3.
ResMed AutoSet Spirit, AutoSet Respond, S7 Elite Service Manual.
Resmed S7 Elite Clinician's Manual.
ResMed AutoSet Spirit, AutoSet Respond, AutoSet S7 Elite Service Manual.
ResMed AutoSet Spirit, AutoSet Respond, AutoSet S7 Elite Service Manual 2.
ResMed S8 AutoSet Vantage System Clinician's Manual.
ResMed S8 Elite/AutoSet Service Manual.
ResMed ResLink Service Manual.
ResMed ResTraxx Quick Reference Guide.
ResMed AutoSet Respond Clinician's Manual.
ResMed ResTraxx Wireless Patient Monitoring Flyer.
ResMed ResTraxx Wireless Patient Monitoring Atlas.
ResMed FDA 510(k) application letter.
ResMed FDA 510(k) application summary.
ResMed VPAP III & VPAP II Series Data Management Guide.
ResMed VPAP II Clinician's Guide.

* cited by examiner

INTEGRATED SLEEP DIAGNOSTIC AND THERAPEUTIC SYSTEM AND METHOD

CROSS REFERENCE TO RELATED APPLICATIONS

This application is a continuation of U.S. patent application Ser. No. 13/074,901 filed on Mar. 29, 2011, which is a continuation of U.S. patent application Ser. No. 11/879,934 filed on Jul. 19, 2007 and issued as U.S. Pat. No. 7,942,824 on May 17, 2011, which is a continuation-in-part of U.S. patent application Ser. No. 11/266,899 filed on Nov. 4, 2005 and issued as U.S. Pat. No. 8,172,766 on May 8, 2012.

The U.S. Government has a paid-up license in this invention and the right in limited circumstances to require the patent owner to license others on reasonable terms provided for by the terms of grant number 2R44HL075983-02 awarded by the National Institutes of Health.

BACKGROUND OF THE INVENTION

Nearly one in seven people in the United States suffer from some type of chronic sleep disorder, and only 50% of people are estimated to get the recommended seven to eight hours of sleep each night. It is further estimated that sleep deprivation and its associated medical and social costs (loss of productivity, industrial accidents, etc.) exceed $150 billion per year. Excessive sleepiness can deteriorate the quality of life and is a major cause of morbidity and mortality due to its role in industrial and transportation accidents. Sleepiness further has undesirable effects on motor vehicle driving, employment, higher earning and job promotion opportunities, education, recreation, and personal life.

Primary sleep disorders affect approximately 50 million Americans of all ages and include narcolepsy, restless legs/periodic leg movement, insomnia, and most commonly, sleep apnea. Sleep apnea is defined as the cessation of breathing during sleep. The three major types of sleep apnea are obstructive sleep apnea (OSA), central sleep apnea (CSA), and complex sleep apnea (CompSA). Of these three, CSA is rare, while OSA is the most common. CompSA is a relatively new disease state that manifests itself after therapy is applied. Patients with CompSA are characterized by the emergence of new CSA events after the application of Continuous Positive Airway Pressure (CPAP). OSA's prevalence in society is comparable with diabetes, asthma, and the lifetime risk of colon cancer. OSA is grossly under diagnosed; an estimated 80-90% of persons afflicted have not received a clinical diagnosis. OSA is characterized by repetitive pauses in breathing during sleep due to the obstruction and/or collapse of the upper airway (throat), usually accompanied by a reduction in blood oxygen saturation, and often followed by an awakening to breathe (an apnea event). Respiratory effort continues during the episodes of OSA. Multiple episodes of apnea may occur in one night, causing sleep disruption. CSA is a neurological condition causing cessation of all respiratory effort during sleep, usually with corresponding decreases in blood oxygen saturation. In contrast to OSA, where there is respiratory effort from the brain stem but a physical blockage prevents inhalation of oxygen, in CSA the brainstem center controlling breathing shuts down, resulting in no respiratory effort and no breathing. The subject is aroused from sleep by an automatic breathing reflex. Frequent activation of the reflex results in very little sleep for the subject. The neurological mechanism behind CSA is very different from the physical cause of OSA. Although the effects of CSA and OSA are highly similar, effective treatment can differ. CompSA can be thought of as a combination of OSA and CSA. As mentioned before, CompSA is characterized by an emergence of CSA events after CPAP initiation.

Medications, hygiene, or some physical form of therapy can be used to treat apneas. Treatment of OSA and CSA vary substantially, which makes a proper diagnosis of the correct type of sleep apnea (OSA, CSA, or CompSA) critical for an effective treatment. Apnea treatment is provided based on the type of apnea, and can be adjusted by re-testing the subject at some later time to determine whether the condition or the symptoms have been alleviated. The most common method of treating OSA is continuous positive airway pressure (CPAP) and positive airway pressure (PAP) devices applied to the subject's airway to force the subject to breathe. When using a simple CPAP device to treat OSA, the air pressure acts as a splint, holding the airway open and reducing or removing the obstruction. The optimal pressure is determined by a sleep technician during a single titration night. The sleep technician manually adjusts the device to deliver a minimum pressure sufficient to force the airway open and reduce the number of apneas. Once the optimal pressure is determined, the device is programmed to consistently provide this pressure, and the patient is sent home.

Slightly more advanced PAP devices automatically adjust the air pressure based on sensors built into the device. The sensors measure gas flow, pressure, or other fluid characteristics in the device or its mask, and adjust the delivered pressure based on various algorithms known in the art. These auto-PAP devices rely on the single physiological variable (the measured or estimated fluid characteristics) to predict or detect an apnea event.

None of the devices on the market can be used to adjust the gas flow delivered to a subject based on a comprehensive evaluation of the subject's current physiological state or the subject's current symptoms. Further, none of the current devices can use a rich data set to predict or detect apnea and provide appropriate treatment. Still further, none of the current CPAP or PAP titration methods use a rich set of data over single or multiple nights to set the optimal pressure and other parameters. Still even further, none of the current devices can be used to automatically adjust a treatment device based on the subject's physiological signals. Still even further, none of the current titration devices can be used in the subject's home.

It is therefore an object of the present invention to adjust the treatment gas flow or pressure delivered to the subject based on the subject's current physiological state or symptoms. It is another object of the present invention to use a rich data set over multiple nights to titrate the CPAP treatment. It is another object of the present invention to use a closed-loop or partially closed-loop system to automatically titrate the CPAP treatment based on the subject's physiological signals. It is still another object of the present invention to treat a subject's apnea in a predictive manner. It is still another object of the present invention to provide a system or method of treating a subject's apnea using the subject's physiological signals. It is still another object of the present invention to provide a device and method of titration in the subject's home. It is still another object of the present invention to provide a device and method of titration in the hospital's acute or sub-acute settings, such as for postoperative management of care.

SUMMARY OF THE INVENTION

The present invention relates to an integrated sleep diagnosis and treatment device, and more particularly to an integrated apnea diagnosis and treatment device. The present invention additionally relates to methods of sleep diagnosis and treatment.

There are numerous embodiments of the present invention with a few of those listed below. The present invention further relates to a sleep diagnosis device integrated with a treatment device. The sleep disorder treatment system of the present invention can use a diagnosis device to perform various forms of analysis to determine or diagnose a subject's sleeping disorder or symptoms of a subject's sleep disorder, and using this analysis or diagnosis can with, or in some embodiments without, human intervention treat the subject either physically or chemically to improve the sleeping disorder or the symptoms of the sleeping disorder. The diagnostic part of the system can use many different types of sensors and methods for diagnosing the severity of the symptoms of or the sleep disorder itself. The treatment part of the system can use a device to physically or chemically treat the subject's symptoms or sleep disorder itself.

The diagnostic part of the system or device can use various sensors for measuring the subject's respirations, cardiac signals, brain wave signals, blood gases, EMG, EOG, airway pressure, and the like. Any sensor that can or has been used with a full polysomnogram (PSG) may likewise be used alone or in combination with other sensors. Sensors for measuring the subject's brain wave signals include EEG electrodes and the like. Sensors for measuring the subject's respirations or oxygen levels include sensors to measure airflow, respiratory effort, oxygenation and ventilation, and the like. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound and the like. Measurement of respiratory effort is preferably measured by esophageal pressure, surface diaphragmatic EMG, inductive plethysmography, and the like. Measurement of oxygenation and ventilation is preferably measured by pulse oximetry, transcutaneous oxygen monitoring, transcutaneous carbon dioxide monitoring, expired end carbon dioxide monitoring, and the like.

Signals from these sensors are then analyzed to determine the level of severity of the symptoms of the subject's sleep disorder and in some cases to diagnose the sleep disorder itself. One particular embodiment of the present invention involves diagnosing the level of severity of a subject's sleep apnea and with or without human intervention adjusting an apparatus for providing positive airway pressure to the subject. The treatment device can be adjusted by either by a closed loop control system (automatically) which uses, in part, the data or signals from the diagnosis device to actuate a physical or chemical treatment system for the subject, or an open loop control system (manually) which can alert a human who then adjusts the treatment device based in part on the data or signals from the diagnosis device. Alternatively, signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc.

The diagnostic device can be linked to the treatment device electronically. By electronically linking, it is envisioned that the devices can be linked through a tether, wireless link or some combination thereof. These wireless links can be RF, IR, RF cellular, RF internet, and the like. The diagnostic device preferably incorporates electronics which allow for the wireless transmission of signals from the diagnostic device to an intermediary device or to the treatment device itself. The intermediary device may be a cell phone, a modem, a wireless router, a router, a PDA, a computer, a processor, combinations thereof, and the like. The diagnostic device may transmit signals over any known communications systems or combination thereof to a remote location or to the treatment device itself as well. The communications can include for example cellular systems, copper wire systems, fiber optic systems, broad band cable systems, the internet, combinations thereof and the like.

Signals from these sensors can also be transmitted to a remote location to allow for remote review or processing of signals for diagnostic or treatment purposes. This allows for attended home titration of the treatment device or remotely attended hospital in-patient titration of the treatment device. The treatment devices can then either be adjusted automatically or manually from the remote location, or automatically adjusted at the location of the subject being titrated. Because this titration or adjustment system allows for the more robust collection of data from the subjects, this system can be better used to titrate the treatment device or devices, and in particular can be used to better adjust a PAP or CPAP device. Since traditional PAP or CPAP devices rely on limited sensor input to adjust the treatment device, mainly airflow pressure at some point on the device, this robust data collected during the titration with the diagnostic device can be used to teach or train the treatment device to correlate the more robust data from the diagnostic device to limited sensor signatures from the PAP or CPAP device to allow for more accurate control. One method of teaching or training the treatment device would be to teach or train a neural network on the treatment device. Another method of titrating the treatment device would be to use a wavelet algorithm to adjust the processor or controller on the treatment device or more preferably to adjust the PAP or CPAP device The treatment device can be any device known to those skilled in the art. The treatment device can either physically or chemically treat the subject's sleeping disorder. An example of physically treating the subject's sleeping disorder would be a device to provide positive airway pressure to a subject. The treatment device can either be a traditional PAP or CPAP, or can include various devices for chemical or medical treatment of the subject. The treatment device could include a $O_2$ tank or source, a $CO_2$ tank or source, a medication or chemical reservoir, combinations thereof, and the like. The subject may also have two or more treatment devices that are titrated at the same time. For example, the subject could have a PAP device that is being titrated at the same time as a functional electrical stimulation (FES) device. The PAP device preferably being used to treat the general obstructive apneas and the FES device preferably for treating central apneas. This application also covers the treatment device for use with these features as well as the treatment device for use with additional sensors. Preferably, a new CPAP or PAP with a respiratory effort belt is used. Another example of chemically treating the subject's sleeping disorder would be to have a medication reservoir where a drug is delivered to the subject in order to treat symptoms of the sleeping disorder. Preferably, this medication reservoir is placed inline with the airflow of a PAP or CPAP device to deliver a nebulized medication or drug to the subject's lungs. Also preferably, the PAP or CPAP device can be used to deliver $CO_2$ to trigger a breathing response to treat specific central apneas. A few of the many embodiments of the present invention are as follows.

In one embodiment, the present invention includes a sleep apnea treatment system comprising: a data acquisition system comprising at least one sensor having a signal, the sensor for determining a physiological characteristic of a subject, and at least one electronic component for receiving the signal and retransmitting the signal from the at least one sensor or transmitting a signal based at least in part on the signal from the at least one sensor; and a CPAP device for treating the subject's sleep apnea, the CPAP device comprising an electrical connection for receiving the retransmitted or transmitted signal.

In another embodiment, the present invention includes a treatment device for treating a sleep-related breathing disorder, the treatment device comprising a data acquisition system comprising at least one sensor having a signal, the sensor for determining a physiological characteristic of a subject, and at least one electronic component for receiving the signal and retransmitting the signal from the at least one sensor or transmitting a signal based at least in part on the signal from the at least one sensor; and a PAP device for treating the subject's sleep-related breathing disorder, the PAP device comprising an electrical connection for receiving the retransmitted or transmitted signal, wherein the PAP device is titrated or adjusted based on at least in part the retransmitted or transmitted signal. The first device allows for collection of physiological data from the subject, which is then used to adjust the PAP device to effectively treat the subject's sleep-related breathing disorder.

Another embodiment of the present invention includes a sleep apnea treatment system comprising a data acquisition system and sleep screening device comprising two or more sensors each having a signal, the sensors each for determining a physiological characteristic of a subject, and at least one electronic component for receiving the signal and wirelessly retransmitting the signal from the at least one sensor or wirelessly transmitting a signal based at least in part on the signal from the at least one sensor; and a CPAP device for treating the subject's sleep apnea, the CPAP device comprising a wireless receiver or transceiver for receiving the retransmitted or transmitted signal wherein the CPAP device is titrated or adjusted based on at least in part the retransmitted or transmitted signal. The ability to wirelessly transmit and receive signals enables the sleep apnea treatment system to operate without tethering the subject. The freedom afforded by such a wireless system can increase subject compliance because the system is easier to use and less restrictive.

Another embodiment of the present invention includes a sleep apnea treatment system comprising a data acquisition system comprising at least one sensor having an electrical signal, the sensor for determining a physiological characteristic of a subject, and at least one electronic component for receiving the electrical signal from the at least one sensor, generating a processed signal based at least in part on the signal from the at least one sensor, and transmitting the processed signal; a CPAP device for treating the subject's sleep apnea, the CPAP device comprising an electrical connection for receiving a transmitted signal; and a remote monitoring station comprising a transceiver for receiving the processed signal from the data acquisition system and transmitting a command signal based at least in part on the transmitted processed signal to the CPAP device wherein the CPAP device is titrated or adjusted based on at least in part the transmitted command signal.

Still another embodiment of the present invention includes a sleep apnea treatment system comprising: a data acquisition system comprising at least three sensors, the sensors for determining at least respiratory effort, pulse oximetry, and airflow of a subject, and at least one electronic component for receiving the signals and retransmitting the signal from the sensors or retransmitting a signal based at least in part on the signal from the at least one of the at least three sensors; and a CPAP device for treating the subject's sleep apnea, the CPAP device comprising an electrical connection for receiving the retransmitted or transmitted signal wherein the CPAP device is titrated or adjusted based on at least in part the retransmitted or transmitted signal.

Another embodiment of the present invention includes a sleep apnea treatment system comprising a data acquisition system comprising at least three sensors, the sensors for determining at least respiratory effort, pulse oximetry, and airflow of a subject, and at least one electronic component for receiving the signals and retransmitting the signals from the sensors or transmitting a signal based at least in part on the signal from the at least one of the at least three sensors; and a CPAP device for treating the subject's sleep apnea, the CPAP device comprising an electrical connection for receiving the retransmitted or transmitted signal, a display means capable of visually representing the retransmitted or transmitted signal, and an interface means allowing a user input wherein the CPAP device is titrated or adjusted based on at least in part the retransmitted or transmitted signal and at least in part on the user input.

Still another embodiment of the present invention includes a sleep-related breathing disorder treatment system comprising a data acquisition system comprising at least one physiological sensor having a signal and at least one electronic component for receiving the signal and wirelessly retransmitting the signal or wirelessly transmitting a signal based at least in part on the signal from the at least one sensor; a treatment interface device comprising at least one electronic component for wirelessly receiving the signal transmitted from the data acquisition system, optionally processing the signal from the data acquisition system, and retransmitting the signal from the data acquisition system or transmitting a signal based at least in part on at least one of the signals from the data acquisition system; and a PAP device for treating the subject's sleep-related breathing disorder, the PAP device comprising an electrical connection for receiving the signal transmitted from the treatment interface device wherein the PAP device is titrated or adjusted based on at least in part the signal transmitted from the treatment interface device.

Still another embodiment of the present invention includes a sleep-related breathing disorder treatment system comprising a data acquisition system comprising at least two sensors, the sensors for determining at least one physiological characteristic of a subject and a video signal, and at least one electronic component for receiving the signals and retransmitting the signals or transmitting a signal based at least in part on at least one of the signals from the sensors; and a PAP device for treating the subject's sleep-related breathing disorder, the PAP device comprising an electrical connection for receiving the retransmitted or transmitted signals wherein the PAP device is titrated or adjusted based on at least in part the retransmitted or transmitted signals.

Yet another embodiment of the present invention includes the steps of: attaching at least one sensor to a subject; connecting the at least one sensor to a data acquisition system, the data acquisition system being capable of receiving an electrical signal from the at least one sensor and retransmitting the signal or transmitting a processed signal based at least in part on the electrical signal from the at least one sensor; collecting data from the at least one sensor attached to the subject while the subject attempts to sleep; retransmitting the signal or transmitting a processed signal based at least in part on the electrical signal from the at least one sensor from the data acquisition system to a PAP or CPAP device, the PAP or CPAP device being capable of receiving the retransmitted or transmitted signal and delivering a flow of pressurized gas to the subject; and periodically using at least part of the retransmitted or transmitted signal to adjust or titrate the flow of pressurized gas delivered by the PAP or CPAP to the subject. The steps of attaching at least one sensor to a subject and of connecting the at least one sensor to a first device can also be switched in this (and every similar) embodiment, meaning that the sensors could be connected to the data acquisition system and then applied to the subject. It is understood that the step of applying at least one sensor to a subject can be accomplished by applying any physiological sensor.

Another embodiment of the present invention includes the steps of: providing at least one sensor, a data acquisition system, and a PAP or CPAP device to a subject, the data acquisition system being capable of receiving an electrical signal from the at least one sensor and retransmitting the signal or transmitting a processed signal based at least in part on the electrical signal from the at least one sensor, and the PAP or CPAP device capable of receiving a command signal and delivering a flow of pressurized gas to the subject; attaching the at least one sensor to the subject; connecting the at least one sensor to the data acquisition system; collecting preliminary electrical signals for a predetermined amount of time from the at least one sensor attached to the subject while the subject attempts to sleep; using the collected preliminary electrical signals to confirm that the subject suffers from a sleep-related breathing disorder that can be treated with a PAP or CPAP device; continuing to collect the electrical signal from the at least one sensor attached to the subject while the subject sleeps; retransmitting the signal or transmitting a processed signal based at least in part on the electrical signal from the at least one sensor from the first device to a remote monitoring station and the PAP or CPAP device; periodically reviewing at least part of the retransmitted or transmitted signal from the remote monitoring station and using the retransmitted or transmitted signal to calculate a command signal designed to titrate or adjust the PAP or CPAP device; and periodically delivering a command signal from the remote monitoring station to the PAP or CPAP device to adjust the flow of pressurized gas delivered by the PAP or CPAP device to the subject.

Another embodiment of the present invention includes the steps of: providing at least one sensor, a data acquisition system, and a PAP or CPAP device to a subject, the data acquisition system being capable of receiving an electrical signal from the at least one sensor and retransmitting the signal or transmitting a processed signal based at least in part on the electrical signal from the at least one sensor, and the PAP or CPAP device capable of receiving the retransmitted or transmitted signal and delivering a flow of pressurized gas to the subject; attaching the at least one sensor to the subject; connecting the at least one sensor to the data acquisition system; collecting preliminary electrical signals for a predetermined amount of time from the at least one sensor attached to the subject while the subject attempts to sleep; using the collected preliminary electrical signals to confirm that the subject suffers from a sleep-related breathing disorder that can be treated with a PAP or CPAP device; continuing to collect the electrical signal from the at least one sensor attached to the subject while the subject attempts to sleep; retransmitting the signal or transmitting a processed signal based at least in part on the electrical signal from the at least one sensor from the first device to the PAP or CPAP device; periodically using at least part of the retransmitted or transmitted signal to titrate or adjust the flow of pressurized gas delivered by the PAP or CPAP to the subject; and collecting the data acquisition system and the at least one sensor from the subject.

Another embodiment of the present invention includes the steps of: providing at least one sensor, a data acquisition system, and a PAP or CPAP device to a subject, the data acquisition system being capable of receiving an electrical signal from the at least one sensor and retransmitting the signal or transmitting a processed signal based at least in part on the electrical signal from the at least one sensor, and the PAP or CPAP device capable of receiving a command signal and delivering a flow of pressurized gas to the subject; attaching the at least one sensor to the subject; connecting the at least one sensor to the data acquisition system; collecting electrical signals from the at least one sensor attached to the subject while the subject attempts to sleep; retransmitting the signal or transmitting a processed signal based at least in part on the electrical signal from the at least one sensor from the first device to a remote monitoring station and the PAP or CPAP device; periodically reviewing at least part of the retransmitted or transmitted signal from the remote monitoring station and using the retransmitted or transmitted signal to calculate a command signal designed to titrate or adjust the PAP or CPAP device; and periodically delivering a command signal from the remote monitoring station to the PAP or CPAP device to adjust the flow of pressurized gas delivered by the PAP or CPAP device to the subject.

Still another embodiment of the present invention includes the steps of: providing at least one sensor, a data acquisition system, and a PAP or CPAP device to a subject, the data acquisition system being capable of receiving an electrical signal from the at least one sensor and retransmitting the signal or transmitting a processed signal based at least in part on the electrical signal from the at least one sensor, and the PAP or CPAP device capable of receiving a command signal and delivering a flow of pressurized gas to the subject; attaching the at least one sensor to the subject; connecting the at least one sensor to the data acquisition system; collecting electrical signals from the at least one sensor attached to the subject while the subject attempts to sleep; retransmitting the signal or transmitting a processed signal based at least in part on the electrical signal from the at least one sensor from the first device to a remote monitoring station and the PAP or CPAP device; automatically determining a set of final values for the flow of pressurized gas delivered by the PAP or CPAP device; transmitting the set of final values for the flow of pressurized gas to the monitoring station; remotely evaluating and approving the set of final values for the flow of pressurized gas; and remotely programming the PAP or CPAP device to deliver a flow of pressurized gas defined by the approved set of final values.

Finally, in still another embodiment, the present invention includes a sleeping disorder treatment system comprising a device for diagnosing and creating a quantitative output of a level of severity of a subject's sleeping disorder or symptoms comprising a pulse oximeter sensor; and a device for physically or chemically treating a subject's sleeping disorder or symptoms, which can be adjusted using in part the output of the level of severity of the subject's sleeping disorder.

Additional features and advantages of the invention will be set forth in the detailed description that follows, and in part will be readily apparent to those skilled in the art from that description or recognized by practicing the invention as described herein, including the detailed description that follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and, together with the description, serve to explain the principles and operation of the invention.

DESCRIPTION OF THE PREFERRED EMBODIMENTS

Figure 1:
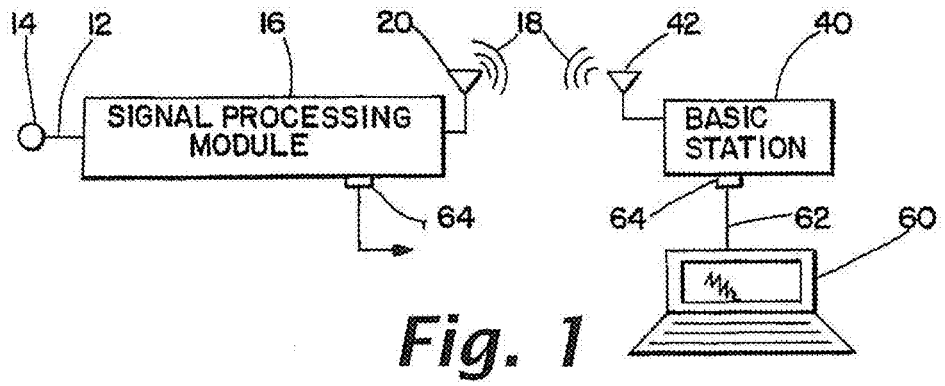
FIG. 1 Block diagram an embodiment of part of the diagnostic device of sleeping disorder treatment system of the present invention.

The present invention is related to a device and method of titrating a sleep disorder treatment, particularly positive airway pressure (PAP) and continuous positive airway pressure (CPAP) treatment for sleep apneas. The present invention is further related to the devices used in executing the method. The present invention includes various embodiments of a method of titrating a sleep disorder treatment device. These embodiments include but are not limited to one or more of the steps described herein. The present invention further includes various embodiments of a device used to titrate a sleep disorder treatment, particularly a PAP or CPAP device. The subjects referred to in the present invention can be any form of animal. Preferably the subject is a mammal, and more preferably a human. Most preferably, the subject is a human being treated for a sleep-related breathing disorder with a PAP or CPAP device.

Various embodiments of the present invention include a step of applying at least one sensor to the subject. The sensors can be applied at any location. Preferably, the sensors are applied in a physician's office or place of business. The physician's place of business includes but is not limited to an office building, a freestanding sleep center, location within a hospital, mobile vehicle or trailer, leased space, or similar location. Just as preferably, the sensors will be mailed to the subject's home or other sleeping location, and the subject will then apply them independently. The subject's sleeping location includes but is not limited to the subject's home, apartment, and the like, as well as a hotel, nursing facility, or other location where an individual could sleep and where this analysis could be done more controllably and/or less expensively than in a sleep lab or hospital setting.

Similarly, the sensors can be applied by a variety of individuals, including but not limited to a physician, nurse, sleep technician, or other healthcare professional. Just as preferably, the sensors could be applied by the subject or the subject's spouse, friend, roommate, or other individual capable of attaching the various sensors. More preferably, the sensors could be applied by the subject or the subject's spouse, friend, roommate, or other individual capable of attaching the various sensors with guidance and instruction. Such guidance and instruction can include static information such as pamphlets, audio recordings (on cassettes, compact discs, and the like), video recordings (on videocassettes, digital video discs, and the like), websites, and the like, as well as dynamic information such as direct real-time communication via telephone, cell phone, videoconference, and the like.

The sensors that are used with various embodiments of the present invention are described herein but can also be any of those known to those skilled in the art for the applications of this method. The collected physiological, kinetic, and environmental signals can be obtained by any method known in the art. Preferably, those sensors include, but are not limited, to wet or dry electrodes, photodetectors, accelerometers, pneumotachometers, sphygmomanometers (for measuring blood pressure), strain gauges, thermal sensors, pH sensors, chemical sensors, gas sensors (such as oxygen and carbon dioxide sensors), transducers, piezo sensors, magnetometers, pressure sensors, static charge-sensitive beds, microphones, audio recorders, video cameras, and the like. Optionally, the data includes a video channel. The invention is envisioned to include those sensors subsequently developed by those skilled in the art to detect these types of signals. For example, the sensors can be magnetic sensors. Because electro-physiological signals are, in general, electrical currents that produce associated magnetic fields, the present invention further anticipates methods of sensing those magnetic fields to acquire the signal. For example, new magnetic sensors could collect brain wave signals similar to those that can be obtained through a traditional electrode applied to the subject's scalp.

Various embodiments of the present invention include a step for applying sensors to the subject. This step can be performed or accomplished in a number of ways. In the simplest form, one sensor is applied to the subject to measure a single channel of physiological or kinetic data. In a more complex form, two sensors are applied to the subject and one additional sensor is contained within the PAP or CPAP device. Preferably, the set of sensors includes one pulse oximeter applied to the subject's index finger, one thoracic respiratory effort belt applied around the subject's chest, and one airflow or air pressure transducer contained within the PAP or CPAP device. In a still more complex form of this step, multiple sensors are applied to the subject to collect data sufficient for a full PSG test. If PSG data are to be collected, the preferred minimal set of sensors includes sensors for two EEG channels, one EOG channel, one chin EMG channel, one airflow channel, one ECG channel, one thoracic respiratory effort channel, one abdominal respiratory effort channel, one pulse oximetry channel, and one shin or leg EMG channel. More preferably, the minimal set of PSG sensors is augmented with at least one additional channel of EOG, one channel of snore, one channel of body position (ex., an accelerometer), one channel of video, and optionally one channel of audio.

Electro-physiological signals such as EEG, ECG, EMG, EOG, electroneurogram (ENG), electroretinogram (ERG), and the like can be collected via electrodes placed at one or several relevant locations on the subject's body. For example when measuring brain wave or EEG signals, electrodes may be placed at one or several locations on the subject's scalp. In order to obtain a good electro-physiological signal, it is desirable to have low impedances for the electrodes. Typical electrodes placed on the skin may have an impedance in the range of from 5 to 10 kΩ. It is in generally desirable to reduce such impedance levels to below 2 kΩ. A conductive paste or gel may be applied to the electrode to create a connection with an impedance below 2 kΩ. Alternatively or in conjunction with the conductive gel, a subject's skin may be mechanically abraded, the electrode may be amplified, or a dry electrode may be used. Dry physiological recording electrodes of the type described in U.S. Pat. No. 7,032,301 are herein incorporated by reference. Dry electrodes are advantageous because they use no gel that can dry out, skin abrasion or cleaning is unnecessary, and the electrode can be applied in a hairy area such as the scalp. Additionally if electrodes are used as the sensors, preferably at least two electrodes are used for each channel of data—one signal electrode and one reference electrode. Optionally, a single reference electrode may be used for more than one channel.

When electrodes are used to collect EEG or brain wave signals, common locations for the electrodes include frontal (F), parietal (P), mastoid process (A), central (C), and occipital (O). Preferably for the present invention, when electrodes are used to collect EEG or brain wave data, at least one electrode is placed in the occipital position and referenced against an electrode placed on the mastoid process (A). More preferably, when electrodes are used to collect EEG or brain wave data, electrodes are placed to obtain a second channel of data from the central location. If further EEG or brain wave signal channels are desired, the number of electrodes required will depend on whether separate reference electrodes or a single reference electrode is used.

If electrodes are used to collect cardiac signals using an ECG, they may be placed at specific points on the subject's body. The ECG is used to measure the rate and regularity of heartbeats, determine the size and position of the heart chambers, assess any damage to the heart, and diagnose sleeping disorders. An ECG is important as a tool to detect the cardiac abnormalities that can be associated with respiratory-related disorders.

As the heart undergoes depolarization and repolarization, electrical currents spread throughout the body because the body acts as a volume conductor. The electrical currents generated by the heart are commonly measured by an array of twelve electrodes placed on the arms, legs, and chest. Although a full ECG test typically involves twelve electrodes, only two are required for many tests such as a sleep study. When electrodes are used to collect ECG with the present invention, preferably only two electrodes are used. When two electrodes are used to collect ECG, preferably one is placed on the subject's left-hand ribcage under the armpit, and the other preferably on the right-hand shoulder near the clavicle bone. Optionally, a full set of twelve ECG electrodes may be used, such as if the subject is suspected to have a cardiac disorder. The specific location of each electrode on a subject's body is well known to those skilled in the art and varies between both individuals and types of subjects. If electrodes are used to collect ECG, preferably the electrode leads are connected to a component of the data acquisition system that includes a processing or pre-processing module that measures potential differences between selected electrodes to produce ECG tracings.

The two basic types of ECG leads are bipolar and unipolar. Bipolar leads (standard limb leads) have a single positive and a single negative electrode between which electrical potentials are measured. Unipolar leads (augmented leads and chest leads) have a single positive recording electrode and use a combination of the other electrodes to serve as a composite negative electrode. Either type of lead is acceptable for collecting ECG signals in the present invention.

Other sensors can be used to measure various parameters of a subject's respirations. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices also preferably measure nasal pressure, respiratory inductance plethysmography, thoracic impedance, expired carbon dioxide, tracheal sound, snore sound, blood pressure and the like. Measurement of respiratory effort is preferably measured by a respiration piezo-electric sensor, inductive plethysmography esophageal pressure, surface diaphragmatic EMG, and the like. Measurement of oxygenation and ventilation is preferably measured by pulse oximetry, transcutaneous oxygen monitoring, transcutaneous carbon dioxide monitoring, expired end carbon dioxide monitoring, and the like.

Optionally, sensors for directly or indirectly measuring respirations can be located in the conduit connecting the PAP or CPAP blower to the gas delivery mechanism. These sensors can include airflow sensors, air pressure sensors, or other sensors to measure characteristics of the gas. Further optionally, sensors can be located near the blower mechanism. These blower sensors can estimate or indirectly measure airflow or air pressure by measuring fan speed or power consumption. Methods of determining airflow or air pressure from sensors placed in or on a PAP or CPAP device are generally known in the art, and any such method is appropriate for the present invention.

One example of such a sensor for measuring respirations either directly or indirectly is a respiration belt. Respiration belts can be used to measure a subject's abdominal and/or thoracic expansion over a measurement time period. The respiration belts may contain a strain gauge, piezo-electric, pressure transducer, or other sensors that can indirectly measure a subject's respirations and the variability of respirations by providing a signal that correlates to the thoracic/abdominal expansion/contractions of the subject's thoracic/abdominal cavity. If respiration belts are used, they may be placed at one or several locations on the subject's torso or in any other manner known to those skilled in the art. Preferably, when a thoracic respiration belt is used, it is positioned below the axilla to measure rib cage excursions. When an abdominal respiration belt is used, it is positioned at the level of the umbilicus to measure abdominal excursions. Optionally, at least two belts are used, with one positioned at the axilla and the other at the umbilicus.

Another example of a sensor or method for measuring respirations either directly or indirectly is a nasal cannula or a facemask used to measure the subject's respiratory airflow. Nasal or oral airflow can be measured quantitatively and directly with a pneumotachograph consisting of a pressure transducer connected to either a standard oxygen nasal cannula placed in the nose, a facemask over the subject's mouth and nose, or the PAP or CPAP gas delivery mechanism. Airflow can be estimated by measuring nasal or oral airway pressure that decreases during inspiration and increases during expiration. Inspiration and expiration produce fluctuations on the pressure transducer's signal that is proportional to airflow. A single pressure transducer can be used to measure the combined oral and nasal airflow. Alternatively, the oral and nasal components of these measurements can be acquired directly through the use of at least two pressure transducers, one transducer for each component. Optionally, the pressure transducer(s) are internal to the patient interface box. If two transducers are used for nasal and oral measurements, preferably each has a separate air port into the patient interface box.

When respirations are measured via airflow or air pressure transducers, preferably the sensors are internal to the PAP or CPAP device itself, either in the PAP or CPAP gas delivery mechanism (i.e., the mask or cannula), or positioned near the blower as described above. Transducers in the PAP or CPAP mask or cannula operate identically to the masks and cannulae described above. Optionally, sensors can be located in the conduit connecting the PAP or CPAP blower to the gas delivery mechanism. Methods of determining airflow or air pressure from sensors placed in or on a PAP or CPAP device are generally known in the art, and any such method is appropriate for the present invention.

Sensors placed on a mask or cannula can also be used to determine other physiological characteristics. Software filtering can obtain "snore signals" from a single pressure transducer signal by extracting the high frequency portion of the transducer signal. This method can eliminate the need for a separate sensor, such as a microphone or another transducer, and also reduces the system resources required to detect both snore and airflow. A modified nasal cannula or facemask connected to a carbon dioxide or oxygen sensor may be used to measure respective concentrations of these gases. In addition, a variety of other sensors can be connected with either a nasal cannula or facemask to measure a subject's respirations directly or indirectly.

Still another example of a sensor or method of directly or indirectly measuring respirations of the subject is a pulse oximeter. The pulse oximeter can measure the oxygenation of the subject's blood by producing a source of light at two wavelengths (typically at 650 nm and 905, 910, or 940 nm). Hemoglobin partially absorbs the light by amounts that differ depending on whether it is saturated or desaturated with oxygen. Calculating the absorption at the two wavelengths leads to an estimate of the proportion of oxygenated hemoglobin. Preferably, pulse oximeters are placed on a subject's earlobe or fingertip. More preferably, the pulse oximeter is placed on the subject's index finger. In one embodiment of the present invention, a pulse oximeter is built-in or hard-wired to the interface box. Alternatively, the pulse oximeter can be a separate unit in communication with either the interface box or the base station via either a wired or wireless connection.

Kinetic data can be obtained by accelerometers placed on the subject. Alternatively, several accelerometers can be placed in various locations on the subject, for example on the head, wrists, torso, and legs. These accelerometers can provide both motion and general position/orientation data by measuring gravity. These accelerometers can be used to detect when patients go to sleep or to detect movements during sleep which are important factors in assessing the actual sleep time which is an important parameter used to generate an accurate assessment of nocturnal respiratory events (such as apnea/hypopnea events, which is the sum of all apneas and hypopneas divided by sleep time; or apnea/hypopnea index [AHI]). A video signal can also provide some kinetic data after processing. Alternatively, stereo video signals can provide three-dimensional position and motion information. Kinetic data includes but is not limited to frequent tossing and turning indicative of an unsuitable mattress, excessive movement of bedding indicating unsuitable sleeping temperatures, unusual movement patterns indicating pain, and the subject's sleeping position.

Other sensors can be used to measure various parameters of a subject's physiological, kinetic, or environmental conditions. These other parameters are preferably measured using sensors or devices such as a photodetectors, light meters, accelerometers, pneumotachometers, sphygmomanometers (for measuring blood pressure), strain gauges, thermal sensors, pH sensors, chemical sensors, gas sensors (such as carbon monoxide detectors), transducers, piezo sensors, magnetometers, pressure sensors, static charge-sensitive beds, audio monitors, microphones, reflective markers, video monitors, hygrometers, and the like. Because the system is programmable, potentially any transducer-type sensor that outputs an electrical signal can be used with the system.

Various embodiments of the present invention include the step of connecting sensors to a data acquisition system. The sensors can be connected to the data acquisition system either before or after they are applied to the subject. The sensors can be permanently hardwired to at least part of the data acquisition system. More preferably, the sensors are connected to at least part of the data acquisition system via a releasable connector. Optionally, the sensors can be connected to at least part of the data acquisition system via non-releasable connector that does not permit disconnection without destruction of the connector. The physiological sensors are generally hardwired (permanently or via a connector) to the data acquisition system, but the ongoing evolution in wireless sensor technology may allow sensors to contain transmitters. Optionally, such sensors are wirelessly connected to the data acquisition system. As such, these sensors and the wireless connection method are considered to be part of the present invention. With the advances in microelectromechanical systems (MEMS) sensor technology, the sensors may have integrated analog amplification, integrated A/D converters, and integrated memory cells for calibration, allowing for some signal conditioning directly on the sensor before transmission.

Preferably, the sensors are all connected in the same way at the same time, although this certainly is not required. It is possible, but less preferable, to connect the sensors with a combination of methods (i.e., wired or wireless) at a combination of times (i.e., some before application to the subject, and some after application to the subject). The sensors can be connected to various parts of the data acquisition system. For example, a thoracic respiratory effort belt can be connected to a patient interface box while a pulse oximeter can be connected a base station. Further, some sensors may not be attached to the subject at all. Examples of such sensors include airflow sensors that are part of the PAP or CPAP device and video cameras or microphones that are placed in the subject's sleeping area. Although these sensors are not attached to the subject, they are still connected to at least one component of the data acquisition system.

Various embodiments of the present invention use a data acquisition system capable of both (a) receiving signals from the sensors applied to or placed near the subject; and (b) retransmitting the signals or transmitting another signal based at least in part on at least one of the collected signals. In its simplest form, the data acquisition system preferably should interface with the sensors and retransmit the signals from the sensors. Preferably, the data acquisition system wirelessly transmits the signals from the sensors. Optionally, the data acquisition system also pre-processes the signals from the sensors and transmits the pre-processed signals. Further optionally, the data acquisition is also capable of storing the signals from the sensors and/or any pre-processed signals.

Optionally, the data acquisition system can be a single box, such as a patient interface box, containing a sensor interface module, a pre-processor module, and a transmitter module. Further optionally, the data acquisition system could consist of several boxes that communicate with each other, each box containing one or more modules. For example, the data acquisition system could consist of: (a) a patient interface box containing a sensor interface module, a pre-processor, a transmitter, and a receiver; and (b) a base station box containing a second pre-processor, a transmitter, and a receiver. In this example, the transmitter and receiver of the patient interface box are used to communicate with the base station box. The transmitter and receiver of the base station box are used to both communicate with the patient interface box and a remote monitoring station, remote analysis station, remote data storage station, and the like. Similarly, the data acquisition could consist of (a) a patient interface box containing a sensor interface module, a transmitter, and a receiver; (b) a processor box containing a pre-processor, a transmitter, and a receiver; and (c) a base station box containing only a receiver and a transmitter. In these configurations, it is not necessary for the transmitters to be of the same type. For example, the transmitter in the patient interface box can be a wired, Bluetooth, or other transmitter designed for short distances, and the transmitter in the base station box can be a WiFi, IEEE 802.11, TCP/IP, or other transmitter designed to establish connections over larger distances.

Several data acquisition systems are suitable for use with the present invention. Preferably, the data acquisition system is a device from Cleveland Medical Devices, Inc. (CleveMed). All current suitable CleveMed data acquisition systems include a patient interface box and a base station. The three CleveMed patient interface boxes described below allow for data backup and storage on a removable SD memory card, with a single 1 GB card providing over 60 hours of recording. The current CleveMed data acquisition systems also each include a base station weighing 130 g that is powered by USB. The USB cable also provides a wired link between the base station and a PC. The CleveMed patient interfaces and base stations contain integrated wireless technology for real-time data transmission within 100 feet line of sight. The CleveMed patient interface boxes currently suitable for use with the present invention include the SleepScout™, Crystal Monitor® 20, and Sapphire™ PSG systems.

The SleepScout™ is a wireless patient interface box that includes a total of 9 input channels for ECG, EMG, thoracic and abdominal respiratory efforts, snore and a generic auxiliary DC input. Two of the channels are fully-programmable, adding flexibility by allowing for any combination of EEG, ECG, EOG or EMG. SleepScout™ also includes several built-in sensors, including body position, pulse oximetry, pressure-based airflow, and a differential pressure transducer that allows for PAP or CPAP titration studies. The SleepScout™ patient interface box weighs 190 g and is powered by two AA lithium batteries. The SleepScout™ transmits data in the 2.4-2.484 GHz ISM band.

The CleveMed Sapphire™ is a wireless patient interface box that includes a total of 22 input channels, including 6 EEG, 2 EOG, 5 EMG, as well as ECG, temperature, body position, and respiratory effort. Six of the channels are EEG, allowing the Sapphire™ to meet guidelines for conducting polysomnogram tests. The Sapphire™ also includes several built-in sensors, including body position, pulse oximetry, and a generic auxiliary DC input. The Sapphire™ patient interface box weighs 538 g and is powered by two AA lithium batteries. The Sapphire™ transmits data in multiple bands, allowing dynamic selection of Wireless Medical Telemetry Service (WTMS) bands (608-614 MHz, 1427-1432 MHz) and two ISM bands (902-928 MHz or 2.4-2.485 GHz), depending on the availability and saturation of transmission bands in the testing location.

The CleveMed Crystal® Monitor 20 is a family of wireless patient interface boxes. Each Crystal® Monitor 20 includes a total of 14 input channels, including two each for EEG, EOG, and EMG, as well as ECG and thoracic and abdominal respiratory efforts. The Crystal® Monitor 20 also includes several built-in sensors, including body position, pulse oximetry, pressure-based airflow, and a generic auxiliary DC input. The Crystal® Monitor 20 patient interface box weighs 210 g and is powered by two AA lithium batteries. The Crystal® Monitor family transmits data in multiple bands; the Crystal® 20-B transmits in the 900 MHz ISM band, and the Crystal® 20-S transmits in the 2.4 GHz ISM band. Selection of the appropriate Crystal® Monitor depends upon the availability and saturation of transmission bands in the testing location.

The data acquisition system is preferably portable. By portable, it is meant, among other things, that the device is capable of being transported relatively easily. Relative ease in transport means that the device is easily worn and carried, generally in a carrying case, to the point of use or application and then worn by the subject without significantly affecting any range of motion. Furthermore, any components of the data acquisition system that are attached to or worn by the subject, such as the sensors and patient interface box, should also be lightweight. Preferably, these subject-contacting components of the device (including the sensors and the patient interface box) weigh less than about 10 lbs., more preferably less than about 7.5 lbs., even more preferably less than about 5 lbs., and most preferably less than about 2.5 lbs. The subject-contacting components of the device preferably are battery-powered and use a data storage memory card and/or wireless transmission of data, allowing the subject to be untethered. Furthermore, the entire data acquisition system (including the subject-contacting components as well as any other sensors, a base station, or other components) preferably should be relatively lightweight. By relatively lightweight, it is meant preferably the entire data acquisition system, including all components such as any processors, computers, video screens, cameras, and the like preferably weigh less in total than about 20 lbs., more preferably less than about 15 lbs., and most preferably less than about 10 lbs. This data acquisition system preferably can fit in a reasonably sized carrying case so the subject or assistant can easily transport the system. By being lightweight and compact, the device should gain greater acceptance for use by the subject.

Various embodiments of the present invention use a data acquisition system capable of storing and/or retransmitting the signals from the sensors or storing and/or transmitting another signal based at least in part on at least one of the signals. The data acquisition system can be programmed to send all signal data to the removable memory, to transmit all data, or to both transmit all data and send a copy of the data to the removable memory. When the data acquisition system is programmed to store a signal or pre-processed signal, the signals from the sensors can be saved on a medium in order to be retrieved and analyzed at a later date. Media on which data can be saved include, but are not limited to chart recorders, hard drive, floppy disks, computer networks, optical storage, solid-state memory, magnetic tape, punch cards, etc. Preferably, data are stored on removable memory. For both storing and transmitting or retransmitting data, flexible use of removable memory can either buffer signal data or store the data for later transmission. Preferably, nonvolatile removable memory can be used to customize the system's buffering capacity and completely store the data.

If the data acquisition system is configured to transmit the data, the removable memory acts as a buffer. In this situation, if the data acquisition system loses its connection with the receiving station, the data acquisition system will temporarily store the data in the removable memory until the connection is restored and data transmission can resume. If, however, the data acquisition system is configured to send all data to the removable memory for storage, then the system does not transmit any information at that time. In this situation, the data stored on the removable memory can be retrieved by either transmission from the data acquisition system, or by removing the memory for direct reading.

The method of directly reading will depend on the format of the removable memory. Preferably the removable memory is easily removable and can be removed instantly or almost instantly without tools. The memory is preferably in the form of a card and most preferably in the form of a small easily removable card with an imprint (or upper or lower surface) area of less than about two in$^2$. If the removable memory is being used for data storage, preferably it can write data as fast as it is produced by the system, and it possesses enough memory capacity for the duration of the test. These demands will obviously depend on the type of test being conducted, tests requiring more sensors, higher sampling rates, and longer duration of testing will require faster write speeds and larger data capacity. The type of removable memory used can be almost any type that meets the needs of the test being applied. Some examples of the possible types of memory that could be used include but are not limited to Flash Memory such as CompactFlash, SmartMedia, Miniature Card, SD/MMC, Memory Stick, or xD-Picture Card. Alternatively, a portable hard drive, CD-RW burner, DVD-RW burner or other data storage peripheral could be used. Preferably, a SD/MMC-flash memory card is used due to its small size. A PCMCIA card is least preferable because of the size and weight.

When the data acquisition system is programmed to retransmit the signals from the sensors, preferably the data acquisition system transmits the signals to a processor for analysis. More preferably, the data acquisition system immediately retransmits the signals to a processor for analysis. Optionally, the data acquisition system receives the signals from one or more of the aforementioned sensors and stores the signals for later transmission and analysis. Optionally, the data acquisition system both stores the signals and immediately retransmits the signals.

When the data acquisition system is programmed to retransmit the signals from the sensors or transmit a signal based at least in part on the signal from the sensors (collectively "to transmit" in this section), the data acquisition system can transmit through either a wireless system, a tethered system, or some combination thereof. When the system is configured to transmit data, preferably the data transmission step utilizes a two-way (bi-directional) data transmission. Using two-way data transmission significantly increases data integrity. By transmitting redundant information, the receiver (the processor, monitoring station, or the like) can recognize errors and request a renewed transmission of the data. In the presence of excessive transmission problems, such as transmission over excessive distances or obstacles absorbing the signals, the data acquisition system can control the data transmission or independently manipulate the data. With control of data transmission it is also possible to control or re-set the parameters of the system, e.g., changing the transmission channel or encryption scheme. For example, if the signal transmitted is superimposed by other sources of interference, the receiving component could secure a flawless transmission by changing the channel. Another example would be if the transmitted signal is too weak, the receiving component could transmit a command to increase the transmitting power. Still another example would be for the receiving component to change the data format of the transmission, e.g., in order to increase the redundant information in the data flow. Increased redundancy allows easier detection and correction of transmission errors. In this way, safe data transmissions are possible even with the poorest transmission qualities. This technique opens a simple way to reduce the transmission power requirements, thereby reducing the energy requirements and providing longer battery life. Another advantage of a bi-directional digital data transmission lies in the possibility of transmitting test codes in order to filter out external interferences, for example, refraction or scatter from the transmission current. In this way, it is possible to reconstruct falsely transmitted data.

Data compression using lossless encoding techniques can provide basic throughput optimization, while certain lossy encoding techniques will offer far greater throughput while still providing useful data. Lossy encoding techniques may include but are not limited to decimation, or transmission of a compressed image of the data. The preferred method for encoding will include special processing from the transmitter that will preprocess the data according to user-selectable options, such as digital filtering, and take into the account the desired visual representation of that information, such as pixel height and target image width. Facilities can be made within the system to control the encoding in order to optimize utilization on any given network. Control over the encoding methods may include, but is not limited to selection of a subset of the entire set of signals, target image size, and decimation ratio.

Data encryption can be applied to secure data transmissions over any network. Encryption methods may include but are not limited to simple obfuscation and sophisticated ciphers. The preferred embodiment of secure data transmission that is compatible with HIPAA and HCFA guidelines will be implemented using a virtual private network. More preferably, the virtual private network will be implemented using a specialized security appliance, such as the PIX 506E, from Cisco Systems, Inc, capable of implementing IKE and IPSec VPN standards using data encryption techniques such as 168-bit 3DES, 256-bit AES, and the like. Still more preferably, secure transmission will be provided by a third party service provider or by the healthcare facility's information technology department. The system will offer configuration management facilities to allow it to adapt to changing guidelines for protecting patient health information (PHI).

Several preferable embodiments of this method employ a wireless data acquisition system. This wireless data acquisition system consists of several components, each wirelessly connected. Data is collected from the sensors described above by a patient interface box. The patient interface box then wirelessly transmits the data to a separate signal pre-processing module, which then wirelessly transmits the pre-processed signal to a receiver. Alternatively, the patient interface box processes the signal and then directly transmits the processed signal directly to the receiver using wireless technology. Further alternatively, the patient interface box wirelessly transmits the signals to the receiver, which then pre-processes the signal. Preferably, the wireless technology used by the data acquisition system components is radio frequency based. Most preferably, the wireless technology is digital radio frequency based. The signals from the sensors and/or the pre-processed signals are transmitted wirelessly to a receiver, which can be a base station, a transceiver hooked to a computer, a personal digital assistant (PDA), a cellular phone, a wireless network, or the like. Most preferably, the physiological signals are transmitted wirelessly in digital format to a receiver.

Wireless signals between the wireless data acquisition system components are both received and transmitted via frequencies preferably less than about 2.0 GHz. More preferably, the frequencies are primarily 902-928 MHz, but Wireless Medical Telemetry Bands (WMTS), 608-614 MHz, 1395-1400 MHz, or 1429-1432 MHz can also be used. The present invention may also use other less preferable frequencies above 2.0 GHz for data transmission, including but not limited to such standards as Bluetooth, WiFi, IEEE 802.11, and the like.

When a component of the wireless data acquisition system is configured to wirelessly transmit data, it is preferably capable of conducting a RF sweep to detect an occupied frequency or possible interference. The system is capable of operating in either "manual" or "automatic" mode. In the manual mode, the system conducts an RF sweep and displays the results of the scan to the system monitor. The user of the system can then manually choose which frequency or channel to use for data transmission. In automatic mode, the system conducts a RF sweep and automatically chooses which frequencies to use for data transmission. The system also preferably employs a form of frequency hopping to avoid interference and improve security. The system scans the RF environment then picks a channel over which to transmit based on the amount of interference occurring in the frequency range.

In this application, transmitting the data wirelessly means that the data is transmitted wirelessly at least in part of the data transfer process. This means, for example, that the data may be transmitted wirelessly from the patient interface box to the base station, which then transmits the data via either a wireless method, such as a wireless cellular card, local wireless network, satellite communication system, and the like, or a wired method, such as a wired internet connection, the testing facility's LAN, and the like. Transmitting the data wirelessly also means, for example, that the data may be transmitted via wired connection from the patient interface box to a base station, which then wirelessly transmits the data wirelessly via any wireless method, such as Bluetooth, IEEE 802.11, wireless cellular card, satellite communication system, and the like to a database that distributes the data over a hardwired system to a sleep unit or lab. Transmitting the data wirelessly also means, for example, that the data may be wirelessly transmitted directly from the patient interface box via WiFi or IEEE 802.11, Bluetooth, wireless cellular card, and the like to a processor, which then transmits the processed data to the sleep unit or laboratory. Preferably, the patient interface box wirelessly transmits the data. This allows for a simplified subject hookup and improved subject mobility.

Preferably, the data acquisition system retransmits the signals from the sensors applied to the subject or transmits a signal based at least in part on at least one of the physiological, kinetic, or environmental signals at substantially a same time as the signal is received or generated. At substantially the same time preferably means within approximately one hour. More preferably, at substantially the same time means within thirty minutes. Still more preferably, at substantially the same time means within ten minutes. Still more preferably, at substantially the same time means within approximately one minute. Still more preferably, at substantially the same time means within milliseconds of when the signal is received or generated. Most preferably, a substantially same time means that the signal is transmitted or retransmitted at a nearly instantaneous time as it is received or generated. Transmitting or retransmitting the signal at substantially the same time allows the physician or monitoring service to review the subject's physiological and kinetic signals and the environmental signals and if necessary to make a determination, which could include modifying the subject's treatment protocols or asking the subject to adjust the sensors.

The receiver (base station, remote communication station, or the like) of various embodiments of the wireless data acquisition system can be any device known to receive RF transmissions used by those skilled in the art to receive transmissions of data. By way of example but not limitation, the receiver can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the receiver can further transmit data to another device and/or back. Further optionally, two different receivers can be used, one for receiving transmitted data and another for sending data. For example, with the wireless data acquisition system used in the present invention, the receiver can be a wireless router that establishes a broadband internet connection and transmits the physiological signal to a remote Internet site for analysis, preferably by the subject's physician or another clinician. Other examples of a receiver are a PDA, computer, or cell phone that receives the data transmission, optionally re-processes the information, and re-transmits the information via cell towers, land phone lines, or cable to a remote processor or remote monitoring site for analysis. Other examples of a receiver are a computer or processor that receives the data transmission and displays the data or records it on some recording medium that can be displayed or transferred for analysis at a later time. Optionally, two or more receivers can be used simultaneously. For example, the patient interface box can transmit signals to a base station receiver that processes and retransmits the signals, as well as a PDA receiver that displays the signals for a clinician to review.

One or more aforementioned sensors are used to develop the data or signals used in the present invention for, optionally, determining a quantitative level of severity of a subject's sleeping disorder and/or symptoms, and more preferably to develop a quantitative measurement of the level of severity of a subject's sleep apnea.

The signals from the one or more sensors used in various embodiments of the present invention are preferably analyzed using a processor and software that can quantitatively estimate or determine the severity of the subject's sleeping disorder or symptoms. Using either a microcontroller of a data acquisition system, a separate computer, base station or processor, a PDA, a processor on a device for treating the subject's sleeping disorder or a combination of these processors, the severity of the subject's sleeping disorder and/or symptoms including apneas is determined and is used at least in part to regulate the physical or chemical treatment of the subject. Also optionally, the one or more sensors used in the system of the present invention can also be tethered to a computer, base station, cell phone, a PDA or some other form of processor or microprocessor.

The processor or microprocessor of various embodiments of the present invention can be part of a remote communication station or base station. The remote communication station or base station can also be used only to relay a pre- or post-processed signal. Preferably, the remote communication station or base station can be any device known to receive RF transmissions such as those transmitted by the wireless data acquisition system described herein. The remote communication station or base station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device including the subject's treatment device and/or back. Further optionally, two different remote communication stations can be used, one for receiving transmitted data and another for sending data. For example, with the sleep diagnosis and treatment system of the present invention, the remote communication system of the present invention can be a wireless router, which establishes a broadband internet connection and transmits the physiological signal to a remote internet site for analysis, preferably for further input by the subject's physician or another clinician. Another example is where the remote communication system is a PDA, computer or cell phone, which receives the physiological data transmission, optionally re-processes the information, and re-transmits the information via cell towers, land phone lines, satellite, radio frequencies or cable to a remote site for analysis. Another example is where the remote communication system is a computer or processor, which receives the data transmission and displays the data or records it on some recording medium, which can be displayed or transferred for analysis at a later time.

The quantitative method for estimating or determining the severity of the subject's sleeping disorder or symptoms is preferably accomplished by using signals or data from the one or more sensors described herein. More preferably, this quantitative method is accomplished in real-time, allowing the subject's symptoms to be treated as they occur. By real-time it is meant that the quantitative diagnosis step is accomplished predictively or within a short period of time after symptoms occur which allows for immediate treatment, thereby more effectively reducing the health affects of such disorder while at the same time also minimizing side effects of the treatment chosen. By real-time, preferably the diagnosis is accomplished within 24 hours of receiving the signals from the one or more sensors on the subject, more preferably within 8 hours, even more preferably within 4 hours, still even more preferably within 1 hour, still even more preferably within 20 minutes, still even more preferably within 5 minutes, still even more preferably within 1 minute, still even more preferably within 10 seconds, still even more preferably within 1 second, still even more preferably within 0.1 seconds and most preferably within 0.01 seconds.

Various algorithms known to those skilled in the art are used to filter out noise from the signal or data, and to then quantify the level of severity of the subject's sleeping disorder or symptoms. This filtered data is then is preferably analyzed using the techniques described in the following paragraph In addition to these sleeping disorder data or signal analysis techniques various controller schemes can be used.

Various sleeping disorders have symptoms that can be predicted based on various combinations of physiological signals or data. Various embodiments of the present invention include the approach to identifying these symptoms prior to onset by identifying various characteristic shifts in the power spectrum of the sensors being used to monitor these physiological conditions. This characteristic shift in these signals or data can be identified and used to trigger an actuator on the physical or chemical treatment device(s) to provide for delivery of a certain level of treatment. The various embodiments of the present invention include but are not limited to the following signal-processing techniques that are utilized to predict the onset of these symptoms.

These are: (i) the standard deviation technique, (ii) a recursively fit ARMAX system identification model, (iii) the Short-Time Fourier Transform (SFFT) technique, and (iv) time-frequency signal analysis with a variety of different kernels. The present invention would also include other on-line signal processing algorithms known to those skilled in the art, such as wavelet analysis, which is similar to time-frequency analysis with a particular kernel function, to identify the shift in power spectrum associated with imminent flow separation that is discussed herein.

The standard deviation technique operates on the principle that there is an increase in pressure fluctuation as the flow begins to separate from the surface of an airfoil, due to either increasing angle of attack or unsteady flow. A sharp increase in the standard deviation of pressure data is observed immediately prior to stall. To trigger the deployment the flow effectors and initiate fluid flow control, a threshold standard deviation can be calculated for each pressure sensor and programmed into the control strategy.

The second embodiment of a method to identify the shift in measured power spectrum of the signal from the pressure transducer to identify stall utilizes a recursively identified system model, particularly an Auto-Regressive Moving Average (ARMA) model. Advantageously, the controller is the ORICA™ controller, an extended horizon, adaptive, predictive controller, produced by Orbital Research, Inc. and patented under U.S. Pat. No. 5,424,942, which is incorporated herein by reference. The ARMA recursive identification method attempts to fit specific models to the measured data or signals. Evaluation of this data reveals distinct, identifiable model order shifts based, which can be used to actuate the treatment device at various levels. Further analysis of the frequency spectrum of the physiological data related to various sleeping disorders reveals recognizable changes in this data or signals. This clear characterization alongside the model order shifts allows the ORICA identifier to classify discrete models based upon various physiological conditions of the subject, thus allowing precisely controlled treatments to be delivered to the subject or patient. A simple function minimization based upon the error associated with each model will enable adaptive model selection for the subject's physiological condition. As the subject's physiological conditions moves toward various critical conditions or symptoms, the model with the best fit to the data will shift into a higher order model. This model shift foretells the onset of the symptom. A second sub-method of identifying impending symptoms using the ARMA and other related models is to track the poles of the identified system model based on the subject over time. As the subject's physiological condition moves toward certain designated critical symptoms, the poles of the identified system model will move toward a condition of symptom onset, thereby indicating to the control system that certain critical symptoms are impending. Either of these two signal identification techniques based on fitting a mathematical model to the system can be utilized to predict the onset of the subject's symptoms. The ARMA model can be adapted to resemble other canonical model forms thereby demonstrating similarity to other system identification methods based on Kalman filtering and similar approaches.

A third embodiment of a method for quantifying the power spectrum measured by the one or more sensors is by using Short-Time Fourier Transforms (STFT). A Discrete Fourier transform (DFT), and its numerically efficient complement the Fast Fourier Transform (FFT), both provide frequency information of a digitized signal or data from the sensors. The DFT and FFT both assume that the signal that is being measured is stationary in time. However, in the case of the subject being tested and treated, the measured signal or data is not stationary in time, which means a typical DFT/FFT approach is inapplicable. However, for short time periods the signal maybe considered to be stationary. Therefore, it is possible to estimate the mean power spectrum by segmenting the physiological data or signals into epochs lasting anywhere from 0.1-5 seconds each, and then applying a discrete-time Fourier transform (DFT) to the windowed data. The DFT is used to calculate the power spectrum of the signal for that epoch. Then the spectral mean and median density are calculated from the power spectrum of the signals from each epoch. Using this method it is possible to identify specific frequency content in the data. As the subject begins to experience the onset of various critical symptoms, the frequency spectrum of the measured and analyzed data will shift, which indicates to the control system that the symptom is beginning.

A fourth embodiment of a signal processing method which can provide indications to the control system that various symptoms are impending, to enable either actuation of the treatment device, is to analyze the sensor data using a time-frequency transform. A time-frequency transform enables both frequency resolution and estimation stability for highly non-stationary signals, which typifies some types of such as some of the data or signals related to various physiological conditions. This is accomplished by devising a joint function of both time and frequency, a distribution that describes the energy and density of a signal simultaneously in both time and frequency. The general form of the time-frequency transform is given by the following $$P(t, w) = \frac{1}{4\prod^2} \int \int \int e^{-j\theta t - j\tau \omega + j\theta u} \phi(\theta, t) \cdot s^*\left(u - \frac{1}{2}\tau\right) s\left(u + \frac{1}{2}\tau\right) du \, d\tau \, d\theta$$

This transform can be used to calculate instantaneous power spectra of a given signal. The actual transformation distribution is selected by changing the kernel, $\Phi(\theta,\tau)$. The function [e−1] is interesting since it is possible to identify any distribution invariant to time and frequency shifts by means of its kernel, and the properties of the kernel are strictly related to the properties of the distribution, given by [e−1].

The diagnostic device of the present invention is used to provide an output which is then used either automatically to adjust the treatment device or by a clinician or the subject to adjust the device which provides the physical or chemical treatment device which is another part of the system of the present invention. There are clearly many embodiments of the present invention, and we will attempt to describe a few herein.

Also optionally, the signals or data received from the sensors through the data acquisition system can be used to train the treatment or therapeutic device. During a titration or adjustment period the (rich) diagnostic data can be used to train the treatment or therapeutic device to recognize more detailed physiological symptoms or signs of a sleeping disorder, or more particularly a sleep disorder by correlating the more robust or rich diagnostic data collected with the data acquisition device with the more limited sensor data from the therapeutic or treatment device. For example, certain conditions which routinely are recognized by a number of sensors can be correlated to the signature of the more limited data from the sensors on the therapeutic or treatment device. For instance, while a central sleep apnea is best recognized by a respiratory effort belt and pulse oximetry. Data from a diagnostic period of time can be compared with the sensor data from the treatment device to determine the signature from such data that indicates a central apnic event occurred. Preferably, the treatment device can include a neural network as part of its control mechanism which allows the treatment device to correlate the limited sensor data with the more robust data from the diagnostic period. Optionally, the treatment device can further include a library of events recorded from one or more subjects that allow for more accurate control of the treatment device, and more effective treatment of the subject.

Various embodiments of the present invention include a treatment interface device comprising at least one electronic component for receiving a signal transmitted from the data acquisition system, optionally processing the signal from the data acquisition system, and retransmitting the signal from the data acquisition system or transmitting a signal based at least in part on at least one of the signals from the data acquisition system. The treatment interface device operates essentially as part of the data acquisition system, with the exception that it also transmits to a treatment device (i.e., a PAP or CPAP device). Preferably, the treatment interface device can be used for the titration and then detached from the treatment device or removed from the subject's sleeping location. This would allow the treatment interface device to be used during titration, collected from the subject, and then reused for titration with another subject.

Preferably, the treatment interface device receives a signal from a component of the data acquisition system and transmits a command signal to the PAP or CPAP device. Like a component of the data acquisition system, the treatment interface device preferably contains a transmitter and a receiver. More preferably, the treatment interface device contains a wireless receiver and/or a wireless transmitter. The transmissions sent and received by the treatment interface device do not necessarily use the same method. For example, the treatment interface device could include both a wireless receiver to receive wireless transmissions from the data acquisition system and a USB transmitter to transmit command signals to the PAP or CPAP device. Optionally, the treatment interface device also contains a receiver or transceiver to receive data from the PAP or CPAP device. Such data could include, for example, PAP or CPAP device status information (ex., whether the device is on or off, error codes, blower speed, etc.), fluid characteristics of the pressurized gas delivered to the patient (ex., airflow, air pressure, humidity, etc.), and the like.

The treatment interface device also preferably contains a processor. Preferably, the treatment interface device uses a processor to execute an algorithm for titrating or adjusting the PAP or CPAP device. The treatment interface device processor can be used to relate all the received signals (from the subject, the environment, and the PAP or CPAP device) to each other, and to predict or determine the next appropriate treatment setting. For example, the treatment interface device could receive a pulse oximetry signal, a thoracic effort signal, and a room temperature signal from a data acquisition system, and an airflow signal from the PAP or CPAP device. The treatment interface device processor would then use the signals to calculate the next appropriate treatment setting. For example, the treatment interface device processor could use the airflow, pulse oximetry signal, thoracic effort, and room temperature to determine that the PAP pressure should be increased by 2 cm $H_2O$. The treatment interface device processor would then create a command signal to instruct the PAP device to increase the pressure appropriately. The treatment device processor is preferably capable of executing closed-loop titration, thereby automatically determining a set of final treatment values for the treatment device. The set of final treatment values for the treatment device are the parameters programmed into the treatment device (i.e., the PAP or CPAP), which the treatment device uses during operation. Once the set of final treatment values are programmed into the treatment device, the treatment device will continue to operate according to the set of final treatment values. For example, if the treatment device were a CPAP device, the set of final treatment values would be the gas pressure delivered to the patient. Similarly, if the treatment device were a bi-PAP device, the set of final treatment values would be the inspiration gas pressure and the expiration gas pressure. The set of final treatment values depends on both the type of treatment device and the results of the titration process. Essentially, the titration process is designed to determine the set of final treatment values for a given treatment device and a given subject. If the treatment interface device contains a processor, it is preferably capable of using a variety of techniques to conduct the titration, including but not limited to lookup tables, relationship algorithms, neural networks, wavelets, fast-Fourier transforms, and the like.

Various embodiments of the present invention include a treatment interface device capable of automatically conducting titration of the treatment device. In this case, the treatment device interface preferably uses a processor to enable closed-loop control for executing the titration adjustments, determining the set of final treatment values, and programming the treatment device to deliver the set of final treatment values. Optionally, the set of final treatment values is sent to a clinician for approval. Various other embodiments of the present invention include a treatment interface device capable of using closed-loop control to run the titration and determine the set of final treatment values, but the treatment interface device is not capable of independently programming the treatment device. In this case, a clinician must review the set of final treatment values, approve or adjust them, and then program the treatment device. Various other embodiments of the present invention include a treatment interface device that is only capable of conducting an open-loop titration. In this case, a clinician must conduct the titration, determine the set of final treatment values, and program the treatment device. Thus, the treatment interface device only provides the clinician with a means to control the treatment device and obtain information from it.

Various embodiments of the present invention include a PAP or CPAP device comprising an electrical connection or component for receiving a retransmitted or transmitted signal. The PAP or CPAP device can be any device known in the art that is capable of delivering a flow of gas to the subject and is capable of being titrated or adjusted. The PAP or CPAP device may receive a signal containing command information only. For example, the PAP or CPAP device could receive a command signal to increase the pressure of gas delivered to the subject, to decrease the gas pressure, or to cease operations. Optionally, the device may receive a signal containing data requiring further processing by the PAP or CPAP device. For example, the data acquisition system could transmit a signal containing pulse oximetry and respiration characteristics, which the PAP or CPAP device further processes to relate to an internal airflow signal and determine the next appropriate gas pressure setting.

The PAP or CPAP device could contain any component known in the art to receive the signals sent from the data acquisition system. For example, if the data acquisition system provides a signal transmitted via USB, the PAP or CPAP device could contain a receiver component for obtaining the transmitted USB signals. Optionally, the PAP or CPAP device may be a wireless receiver. In this case, for example, the PAP or CPAP device wirelessly receives the signals from a transmitting component of the data acquisition system (the patient interface box, the base station, or other component capable of wirelessly transmitting signals), optionally processes the signal, and makes an adjustment to the flow of gas provided to the subject. Further optionally, the PAP or CPAP device contains a component for receiving a signal transmitted from a remote monitoring station. In this case, for example, a remote monitor receives data from the data acquisition system, determines the next appropriate gas pressure setting, and transmits the setting to the PAP or CPAP device.

Various embodiments of the present invention include a PAP or CPAP device capable of processing the received signal. Such processing can be used to relate the received signals to each other and any additional signals collected by the PAP or CPAP device itself. For example, the PAP or CPAP processor could receive a pulse oximetry signal from a data acquisition system, an airflow signal from the PAP or CPAP device itself, and a signal to increase the gas pressure from a remote monitor. The PAP or CPAP processor would then relate the signals to each other, thereby creating a lookup table of values or a more sophisticated relationship algorithm. The PAP or CPAP processor is optionally capable of creating a neural network and training the network with data collected from an individual subject over several nights. Such a neural network could "teach" the PAP or CPAP device to accurately predict apnea events (confirmed with physiological sensors) based only on gas flow characteristics. In this way, the PAP or CPAP device can continue to operate correctly based on gas flow characteristics alone, and the physiological sensors become redundant.

Various embodiments of the present invention include the step of processing or pre-processing the signals received from the sensors attached to the subject. The processor or preprocessor of various embodiments of the present invention can be independent, or combined with any other component. For example, a processor or preprocessor could be a part of the patient interface box, base station, treatment interface, or PAP or CPAP device. Optionally, the processor or preprocessor could be distributed between two or more components of the device. Optionally, preprocessing can correct artifacts, derive a total sleep time, derive a snore signal, filter a signal, or compress and/or encrypt the data for transmission as described above. Preferably, the preprocessing step corrects for artifacts present in the sensor signals. Optionally, a step of more powerful processing can perform one or more of the preprocessing functions. Further optionally, more powerful processing can determine the appropriate pressure to be delivered by the PAP or CPAP to the subject. Further optionally, more powerful processing can determine whether the patient has central or obstructive sleep apnea. For example, in the case of CSA, the processing can provide a recommendation to stop CPAP treatment and use another treatment specific to CSA.

Various embodiments of the present invention include a system capable of determining the location of obstructions in the airways of subjects. This feature is helpful because one OSA treatment modality is surgical procedures that rely on excising part of the tissue causing the obstruction. In these embodiments, the system detects an obstructive apnea event, and then determines the location of the obstruction using acoustic reflectance methods. A sound wave created by an oscillating piston (tuning fork, membrane, loudspeaker, and the like), an aperture (whistle, reed, and the like), or any other method of producing a sound of known frequency is introduced into the flow of pressurized gas delivered to the patient. The sound wave can be generated inside the PAP or CPAP device, inside the mask, or at any other suitable location. Preferably, the sound is outside the audible frequency range to minimize disturbance to the subject. A pressure transducer in the system will then receive the pressure signals generated by the echo waves bouncing back from the obstructed wall inside the airways. Effectively, the data acquisition system will "listen" to the echoes coming back from inside the subject's airways. Using the delay between the known time of the original sound wave and the detected echo, the system can calculate the location of the obstruction. Measuring the pressure of the reflected sound wave can allow the system to distinguish between the obstruction and other anatomical features of the airway. It is expected that the obstruction site will generate the biggest pressure amplitude, thereby differentiating it from other nearby structures. Also, the system could be configured to "listen" for charges in frequencies or detect an echo signature to determine the density of the tissue the sounds waves are reflected from. Thus allowing for the determination between hard and soft tissue.

Signal quality of the signals from all the sensors can be affected by the posture and movement of the subject. For methods of the present invention, it is important to reduce motion artifacts from the sensor placement. Errors in the form of noise can occur when biopotential data acquisition is performed on a subject. For example, a motion artifact is noise that is introduced to a biopotential signal via motion of an electrode placed on the skin of a subject. A motion artifact can also be caused by bending of the electrical leads connected to any sensor. The presence of motion artifacts can result in misdiagnosis, prolong procedure duration and can lead to delayed or inappropriate treatment decisions. Thus, it is imperative to remove motion artifact from the biopotential signal to prevent these problems from occurring during treatment.

The present method of collecting signals from a subject includes a means of reducing motion artifacts. When physiological electrodes are used, preferably they are used with conductive gels or adhesives. More preferably, dry electrodes are used with or without conductive gels or adhesives. Still more preferably, the device's firmware and/or software uses body motion information for artifact correction. Most preferably, a combination of the above methods is used.

The most common methods for reducing the effects of motion artifacts in sensors such as electrodes have focused on skin deformation. These methods include removing the upper epidermal layer of the skin by abrasion, puncturing the skin near the electrode, or measuring skin stretch at the electrode site. The methods for skin abrasion ensure good electrical contact between the electrode and the subject's skin. In this method, an abrasive pad is mechanically rotated on the skin to abrade the skin surface before electrode placement. Similarly, medical electrodes have been used with an abrading member to prepare the skin after application of the electrode whereby an applicator gun rotates the abrading member. Methods of skin preparation that abrade the skin with a bundle of fibers have also been disclosed. These methods provide a light abrasion of the skin to reduce the electrical potential and minimize the impedance of the skin, thereby reducing motion artifacts.

Skin abrasion methods can cause unnecessary subject discomfort, prolong procedure preparation time and can vary based on operator experience. Furthermore, skin abrasions methods can lead to infection, and do not provide an effective solution to long term monitoring. Dry physiological recording electrodes could be used as an alternative to gel electrodes. Dry physiological recording electrodes of the type described in U.S. Pat. No. 7,032,301 are herein incorporated by reference. Dry physiological electrodes do not require any of the skin abrasion techniques mentioned above and are less likely to produce motion artifacts in general.

Although the above-mentioned methods reduce motion artifacts, they do not completely eliminate them and they are less effective for sensors that do not measure a biopotential signal, such as respiratory effort belts, flow meters, environmental sensors, and the like. The invention preferably incorporates a step to more completely remove motion and other artifacts by firmware and/or software correction that utilizes information collected preferably from a sensor or device to detect body motion, and more preferably from an accelerometer. In certain embodiments of the present invention, a 3-D accelerometer is directly connected to the data acquisition system. The data acquisition system receives signal inputs from the accelerometer and at least one set of other physiological or kinetic signals. The microprocessor applies particular tests and algorithms comparing the two signal sets to correct any motion artifacts that have occurred. The processor in one embodiment applies a time synchronization test, which compares the at least one set of physiological or kinetic signal data to the accelerometer signal data synchronized in time to detect motion artifacts and then remove those artifacts. Alternatively, the processor may apply a more complicated frequency analysis. Frequency analysis preferably in the form of wavelet analysis can be applied to the accelerometer and at least one set of physiological or kinetic signals to yield artifact detection. Yet another alternative is to create a neural net model to improve artifact detection and rejection. This allows for the system to be taught over time to detect and correct motion artifacts that typically occur during a test study. The above illustrations are only examples of possible embodiments of the present invention and are not limitations. The accelerometer data need not be analyzed before wireless transmission; it could be analyzed by a base station, computer, or the like after transmission. As should be obvious to those skilled in the art, a 2-D accelerometer or an appropriate array of accelerometers could also be used. Gyroscopes could be used as well for these purposes.

Sensors can be used to detect motion of the subject's body or a portion of the subject's body. The motion information can then be used to detect the posture and movement of the subject. This motion information may indicate that the subject has a sleeping disorder unrelated to breathing, such as restless legs syndrome (RLS) or other parasomnia. The motion information can be used to correct for error in the form of noise or motion artifact in the other sensor channels. To detect motion, various embodiments of the present invention include sensors, devices, and methods of determining the posture and movement of the subject. This information can be used when analyzing the physiological signals. The posture and movement of the subject is preferably determined by signals received from an accelerometer or an array of two or more accelerometers. Accelerometers are known in the art and are suitable for use as motion-monitoring units. Various other types of sensors can be additionally or alternatively used to sense the criteria (e.g., vibration, force, speed, and direction) used in determining motion. For particularly low power designs, the one or more sensors used can be largely mechanical.

Body movement of the subject will result in a high amplitude signal from the accelerometer. The data acquisition system can also monitor the sensor signals for any indication that the subject has moved, for example from a supine position to an upright position. For example, the integrated velocity signal computed from the vertical acceleration component of the sensor data can be used to determine that the subject has just stood up from a chair or sat up in bed. A sudden change in the vertical signal, particularly following a prolonged period with little activity while the subject is sleeping or resting, confirms that a posture-changing event occurred. The data acquisition system can also monitor the sleep-wake cycle of the patient. Sleep-wake data will be used to determine the total sleep time for the calculation of the apnea/hypopnea index and other sleep related indices.

In addition, a video camera can be used to detect subject movement and position, and the information then used to correct any artifacts that may have arisen from such movement. Preferably, the camera is a digital camera. More preferably, the camera is a wireless digital camera. Still more preferably, the camera is a wireless digital infrared camera. Preferably, the video acquired from the camera is processed so that the subject's movement and position are isolated from other information in the video. The movement and position data that are acquired from the video is then preferably analyzed by software algorithms. This analysis will yield the information needed to make artifact corrections of the physiological signals. Optionally, alternative analysis of the video signal can indicate additional sleeping disorders, such as restless legs syndrome (RLS), sleepwalking, or other parasomnia.

One specific embodiment of the present invention using video subject movement detection involves the use of specially marked electrodes. The electrodes can be any appropriate electrode known in the art. The only change to the electrode is that they preferably have predetermined high contrast marks on them to make them more visible to the video camera. These marking could be manufactured into the electrodes or simply be a sticker that is placed on the back of the electrodes. These markings enable the video system to accurately distinguish the electrodes from the rest of the video image. Using the markers on each visible electrode, the system can calculate of the movement of each individual electrode, thus allowing for more accurate artifact correction.

In another specific embodiment of the invention, the system can detect subject movement by monitoring the actual movement of the subject's body. Software is applied to the video that first isolates the position of the subject's body, including limbs, and then continues to monitor the motion of the subject.

There are numerous advantages to using video over other means of artifact detection and correction. Foremost, video allows for the calculation of movement artifacts from each individual electrode without the need for accelerometers. This makes the use of video very cost effective in relation to other available methods. The video also can be used in conjunction with the accelerometer data to correct for motion artifacts, thus increasing the precision and accuracy of the system's motion artifact correction capabilities.

Current auto-titrating machines adjust PAP or CPAP pressure based on airflow/pressure alone. The advantage of using multiple parameters over just an airflow or pressure parameter is that the PAP or CPAP can now confirm events and differentiate between central apnea and hypopneas and obstructive apneas and hypopneas. For example, when airflow drops, existing commercial systems will "assume" the event is obstructive; however, the current invention will "know" whether it is obstructive or central by further investigating two other parameters. If pulse ox drops below 3% and thoracic effort persists, then the apnea/hypopnea is obstructive. If the pulse ox drops below 3% and the thoracic effort ceases then the apnea/hypopnea is central. If pulse ox does not drop by 3% then the event cannot be considered an hypopnea at all.

It is a benefit for auto-titrating machines to confirm or to know central apneas vs. obstructive apneas, since central events are indicative of more serious cardiovascular problems and, more often than not, they cannot be properly treated with conventional CPAP treatment. Additional treatment such as oxygen is needed. It is suspected that up to 15% of patients develop central events once they are placed on PAP or CPAP. The development of central events after PAP or CPAP administration is thought to be generated by a newly discovered and newly created disease called Complex Sleep Apnea (CompSA), which requires a very different treatment than the traditional CPAP.

A method to automatically titrate PAP or CPAP pressure is based on the above physiological parameters that are specific to the subject. The shapes of physiological signals often differ between subjects, especially during events such as hypopneas, apneas, upper airway resistance, central apneas, and others. The ability to wear a portable data acquisition system or device for a few days will allow the PAP or CPAP to be trained on the physiological signals that are specific to that subject. This "subject specific" information can then be used to better optimize auto-titration since it can now better detect hypopneas, apneas, etc.

Preferably, the titration method of the present invention includes a step whereby the titration analysis runs over a minimum period of time, preferably at least 15 minutes, before pressure adjustment occurs. This period is needed to make sure pressure is not titrated up or down without sufficient confirmation of the event. For example, in the event a subject holds their breath for whatever reason, perhaps a bad dream, if the adjustments are made quickly a traditional system may unnecessarily increase pressure because the system has falsely detected an apnea. This is why it is necessary to wait a sufficient period of time, so that non-pathogenic irregular breathing does not affect the PAP or CPAP titration.

Various embodiments of the present invention include the step of conducting PAP or CPAP titration that is attended from a remote location. Such remote attendance can be accomplished in several ways, for example by an individual in a remote location (a remote monitor) periodically or continuously viewing the data transmitted from the data acquisition system, including signals from the sensors and a preprocessed signal or signals based at least in part on at least one of the sensors. Remote monitoring can be achieved at various levels, including but not limited to, post-titration approval, titration approval, and active titration. Further, each level of monitoring can be either periodic or continuous, and can incorporate automatic alerts. Several illustrative examples of monitoring are described below.

In a post-titration approval monitoring scheme, the remote monitor receives a report of the titration process after completion. In this example, the subject receives a completely automated titration system that independently determines the appropriate pressure of the delivered gas. While the subject sleeps or attempts to sleep, the system automatically adjusts to find the set of final treatment values (i.e., the optimal gas pressure). Then the PAP or CPAP device programs itself to continue delivering the set of final treatment values. The system also sends the collected data and set of final treatment values to the remote monitor, who reviews the collected data and approves or rejects the system's set of final treatment values. If the monitor approves the system's set of final treatment values, the subject can return all the equipment other than the PAP or CPAP device and then use the PAP or CPAP device for ongoing treatment.

In this scenario, the remote monitor is not actively engaged in the titration process. This type of monitoring is typically periodic, with the remote monitor reviewing the data at a single point (after the end of the titration), or at multiple points, for example at the end of each night during a multi-night titration. This type of monitoring could also be continuous, in that the remote monitor continuously receives data from the titration system. Post-titration approval monitoring is generally suited to subjects with relatively simple apnea and few complicating factors. Preferably, the review portion of the post-titration approval monitoring takes place within a few weeks of the titration night(s). More preferably, the review takes place within one week; more preferably within three days; still more preferably within one day; still more preferably within six hours; still more preferably within one hour of the end of the titration nights.

In a titration approval monitoring scheme, the remote monitor receives a report of the titration process after completion. In contrast to the post-titration approval, however, the remote monitor must approve the set of final treatment values before the PAP or CPAP device is programmed to continue delivering that pressure. In this example, the subject could receive an automated titration system that independently determines the set of final treatment values by automatically adjusting while the subject sleeps. The system then sends the collected data and set of final treatment values to the remote monitor, who reviews the collected data and approves or modifies the system's set of final treatment values. If the monitor approves the system's set of final treatment values, the remote monitor programs the PAP or CPAP device to continue using set of final treatment values. Optionally, the subject could receive a semi-automated titration system that periodically changes treatment values. The system sends the collected data and corresponding treatment values to the remote monitor, who reviews all the data and determines the set of final treatment values. After the remote monitor determines the set of final treatment values, the PAP or CPAP device is programmed to deliver it.

This type of monitoring is typically periodic, with the remote monitor reviewing the data at a single point (after the end of the titration), or at multiple points, for example at the end of each night during a multi-night titration, or several times during the titration nights. This type of monitoring could also be continuous, in that the remote monitor continuously receives data from the titration system. Preferably, the remote monitor determines the optimal gas pressure within one day; still more preferably within six hours; still more preferably within one hour of the end of the titration nights, and most preferably within 20 minutes of the end of the titration.

In an active titration monitoring scheme, the remote monitor receives signals from the system during the titration phase. Preferably, the remote monitor receives data every hour; more preferably the remote monitor receives data every twenty minutes; more preferably every five minutes; and most preferably the remote monitor receives continuous streaming data during the titration phase. In contrast to the post-titration approval and titration approval, the remote monitor is actively engaged in the titration process. In this example of monitoring, the subject could receive a titration system that collects and transmits data to the remote monitor. The remote monitor then reviews the data and determines the next level of gas pressure for the titration. The remote monitor transmits the appropriate command to the PAP or CPAP device (ex., to increase or decrease the gas pressure), and data collection continues until the treatment value requires adjustment. After the remote monitor has completed the titration and determined a set of final treatment values, the PAP or CPAP device is programmed to continue using the set of final treatment values. This type of monitoring can be periodic, with the remote monitor reviewing the data at multiple points, for example just before each change in PAP or CPAP gas pressure. This type of monitoring could also be continuous, with the remote monitor continuously receiving and reviewing data.

Other types of remote monitoring can include only monitoring at the beginning of the titration to assess the quality of the collected signals. For example, the subject can set up the titration system, and the remote monitor can view preliminary data for adequacy. If a sensor has been improperly placed or incorrectly connected, the remote monitor can instruct the subject to take remedial action. In this way, the remote monitor can ensure receipt of sufficient and adequate data to perform the titration correctly.

Each level of monitoring can include an alert function wherein the monitor receives alerts of predetermined events. For example, the monitor could be alerted when the subject's oxygen saturation drops below a predetermined threshold, when the PAP or CPAP device is instructed to deliver a gas pressure over a safety threshold, every time the system changes the pressure, when an electrode's impedance increases, if a sensor malfunctions, or for any other event. The system can also be programmed to alert the remote monitor of more complex events, such as detection of an apnea event after the PAP or CPAP has reached a defined gas pressure setting, a drop in oxygen concentration combined with cessation of thoracic breathing activity, or a sensor has moved and no back-up sensors are available. Preferably, the alert function is provided in all of the monitoring schemes described above.

Preferably, the remote monitor is capable of communicating with the subject, subject's assistant, or other individual near the subject. Such communication allows the remote monitor to provide instructions to the subject, subject's assistant, or other individual near the subject, for example, to adjust a sensor, close window blinds, remove a source of noise, turn off any equipment, or wake the subject. More preferably, the remote monitor is capable of two-way communication with the subject, subject's assistant, or other individual near the subject. Such communication allows the subject, subject's assistant, or other individual close to the subject to ask the remote monitor questions, for example, to clarify instructions.

Various embodiments of the present invention include a step of monitoring a subject from a separate monitoring location. Data transmitted in a remote monitoring application may include, but are not limited to, physiological data, kinetic data, environmental data, PAP or CPAP device data, audio, and video recording. It is preferable that both audio and video communications be components of the envisioned system in order to provide interaction between the subject and remote monitor.

Preferably, the data is transmitted from a base station to a database or remote monitoring location with a wireless module or card through a cellular service provider. The envisioned remote monitoring application may allow for multiple remote monitoring locations anywhere in the world. Remote data collection to monitoring station configurations may include, but are not limited to one-to-one, one-to-many, many-to-one, or many-to-many. The envisioned system may include a central server, or group of servers that can collect data from one or more remote sites and offer delivery to multiple viewing clients.

It is preferable that the remote monitoring application employ a wireless network link between the subject and caregiver such as a cellular wireless network. Other wireless techniques include but are not limited to satellite communications, direct radio, infrared links, and the like. Data transmission through a wired network such as dial-up modem, digital subscriber line (DSL), or fiber-optic, while less preferable, can also be used. Bandwidth management facilities will be employed to facilitate remote monitoring in low-speed communication networks. Several data compression techniques are envisioned to maximize system utilization in low-bandwidth environments.

The envisioned remote monitoring step will require data processing, storage, and transmission. This step may be completed or accomplished in one or more modules of the data acquisition system. The preferred embodiment realizes the remote system as two separate components with a patient interface module that can collect, digitize, store, and transmit data to a base station module that can store, process, compress, encrypt, and transmit data to a remote monitoring location. The preferred embodiment of the remote monitoring system will consist of several system modules. A patient interface module will collect physiological and kinetic data from the subject and transmit the signals to a base station module. The base station module will receive the physiological and kinetic data from the patient interface module, and will also preferably directly connect to any environmental sensors and any PAP or CPAP sensors. The base station module will preferably consist of an embedded computer equipped with a cellular wireless data/voice card and a night-vision video acquisition system. The embedded computer will collect, analyze, compress, and encrypt the data and relay them to one or more viewing caregivers. The remote monitoring systems will broadcast their dynamically assigned IP addresses to a dedicated address server, which will be used for lookup by the viewing caregivers. Computer software used by caregivers will enumerate each remote monitoring system in the field using the aforementioned address server and allow caregivers to select one or more for monitoring. The software will have the ability to control data acquisition including start and stop of acquisition, as well as system reconfiguration.

The software preferably will also provide real-time control over the display of data including page width, amplitude, color, montage, and the like. The software will also provide both real-time video and audio communication with the subject using dual services from the cellular card. Video will preferably be transmitted through the data connection, and audio will preferably be transmitted through the voice connection.

While the equipment and methods used in the various embodiments of the present invention can be used in rooms or buildings adjacent to the subject's sleeping location, due to the equipment's robust nature these methods are preferably performed over greater distances. Preferably, the subject's sleeping location and the remote locations, for example the location of the remote monitor, are separate buildings. Preferably, the subject's sleeping location is at least 1 mile from the remote location(s) receiving the data;

more preferably, the subject's sleeping location is at least 5 miles from the remote location(s) receiving the data; even more preferably, the subject's sleeping location is at least twenty miles from the remote location(s) receiving the data; still more preferably, the subject's sleeping location is at least fifty miles from the remote location(s) receiving the data; still even more preferably, the subject's sleeping location is at least two hundred-fifty miles from the remote location(s) receiving the data; more preferably, the subject's sleeping location is in a different state from the remote location(s) receiving the data; and most preferably, the subject's sleeping location is in a different country from the remote location(s) receiving the data.

Various embodiments of the present invention include the step of evaluating the received signals to determine if they are adequate for later analysis. This step can be performed or accomplished a number of ways. In the simplest form, the signal can be evaluated once just prior to the start of the sleep study. In another form, the signal is evaluated periodically during the study to determine its quality. Preferably, the signal(s) are evaluated both at the start of the study and periodically during the study. Most preferably, the signals are evaluated at the beginning of the study and continuously during the study. If the signals are evaluated for adequacy, preferably the subject can be contacted to adjust the sensor as necessary. In this way, corrective action can adjust an inadequate signal to increase the value of the sleep study data and enable later analysis.

The data collected for the sleep analysis conducted under the various methods of the present invention can be viewed by any number of medical personnel and the subject themselves, if appropriate. Preferably, the data is available to a sleep technician, to a doctor making the analysis/diagnosis based on the data, and others involved in these methods. This data can be reviewed at multiple locations including but not limited to the doctor's home or office, or anywhere else the doctor or other individuals associated with the analysis/diagnosis have access to the internet or an intranet.

Referring now to the drawings and, in particular to FIG. 1, there is shown a block diagram of the present invention. An external input 12 from sensor 14 is input to signal processing module 16. Although, one sensor 14 and one external input 12 are shown, the signal processing module 16 is capable of accepting multiple external inputs 12 from multiple sensors 14. The signal processing module 16 generates a signal 18 encoded with data corresponding to the external input 12. The signal processing module 16 transmits the signal 18 by wireless means to a base station 40. In FIG. 1, the wireless means is shown as radio frequency (RF). In this case, the signal processing module generates a radio frequency signal 18 by frequency modulating a frequency carrier and transmits the radio frequency signal through module antenna 20. The base station 40 receives the radio frequency signal 18 through base antenna 42, demodulates the radio frequency signal 18, and decodes the data. It is understood that other wireless means can be utilized with the present invention, such as infrared and optical, for example. Although one module antenna 20 and one base antenna 42 is shown in this embodiment, it is understood that two or more diversity antennas can be used and are included in the present invention. An external programming means 60, shown in FIG. 1 as a personal computer, contains software which is used to program the signal processing module 16 and the base station 40 through data interface cable 62. The data interface cable 62 is connected to the base station 40 and signal processing module 16 by respective connectors 64. The same data interface cable 62 or two different interface cables 62 can be used, one for the base station 40 and one for the signal processing module 16. The signal processing module 16 and the base station 40 can be programmed by connecting a data interface cable 62 between it and an external programming means 60 or by radio frequency (or other type) of signals transmitted between a base station 40 to the signal processing module 16 or to another base station 40. RF signals, therefore, can be both transmitted and received by both signal processing module 16 and base station 40. In this event the signal processing module 16 also includes a module receiver 29 while the base station 40 also includes a base transmitter 84, in effect making both the signal processing module 16 and the base station 40 into transceivers. In addition, the data interface cable 62 also can be used to convey data from the base station 40 to the external programming means 60. If a personal computer is the external programming means 60, it can monitor, analyze and display the data in addition to its programming functions. The base receiver 80 and module receiver 29 can be any appropriate receivers, such as direct or single conversion types. The base receiver 80 preferably is a double conversion superheterodyne receiver while the module receiver 29 preferably is a single conversion receiver. Advantageously, the receiver employed will have automatic frequency control to facilitate accurate and consistent tuning of the radio frequency signal 18 received thereby.

Figure 2:
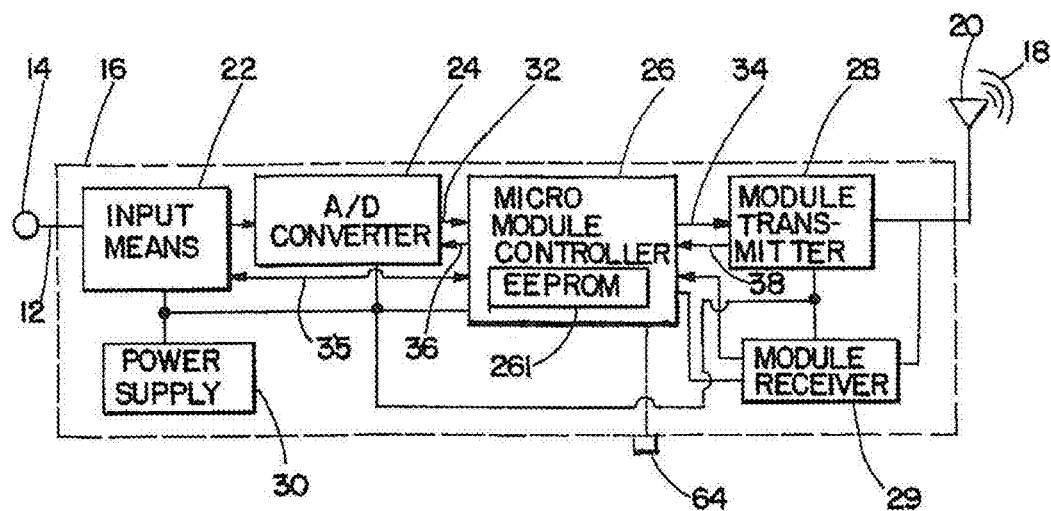
FIG. 2 Block diagram of one embodiment of the signal processing step of the present invention.

Referring now to FIG. 2, there is shown a block diagram of the signal processing module 16 with the sensor 14 and the module antenna 20. The signal processing module 16 comprises input means 22, analog-to-digital (A/D) means 24, a module microcontroller 26 with a nonvolatile memory, advantageously, an EEPROM 261, a module transmitter 28, a module receiver 29 and a module power supply 30. Although the module antenna 20 is shown externally located from the signal processing module 16, it can also be incorporated therein. The module antenna 20 may be a printed spiral antenna printed on a circuit board or on the case of the signal processing module 16 or other type of antenna. A module power supply 30 provides electrical power to the signal processing module 16 which includes the input means 22, A/D means 24, module microcontroller 26 module transmitter 28 and module receiver 29.

The input means 22 is adjustable either under control of the module microcontroller 26 or by means of individually populatable components based upon the specific external input 12 characteristics and range enabling the input means 22 to accept that specific external input 12. For example, if the input is a 4-20 mA analog signal, the input means 22 is programmed by the module microcontroller 26 and/or populated with the components needed to accept that range and characteristic of signals. If the input characteristics change the programming and/or components change accordingly but the same platform circuit board design is utilized. In other words, the same platform design is utilized notwithstanding the character, range, or quantity (number of external inputs 12) [up to a predetermined limit] of the input. For example, bioelectric signals such as EEG, EMG, EKG, and EOG have typical amplitudes of a few microvolts up to a few tens of millivolts. For a given application, a specific frequency band of interest might be from 0.1 Hz to 100 Hz, whereas another application may require measurement of signals from 20 Hz to 10 KHz. Alternatively, measurement of vital signs such as body temperature and respiration rate may deal with signals in a range of +5 volts, with a frequency content from DC (0 Hz) to 20 Hz. For other applications such as industrial process monitoring, the information of interest may be contained in the signal as a current, such as a 4 to 20 mA current loop sensor, or it may take the form of resistance, impedance, capacitance, inductance, conductivity, or some other parameter, The present invention provides a single device for measuring such widely disparate signal types and presents distinct economic advantages, especially to small enterprises such as a medical clinic located in a rural area, which would be empowered by this invention to conduct tests which would otherwise have required subject travel to a large medical center, with all the attendant cost thereof.

This is possible due to the selectively adaptable input means 22 and A/D means 24, the frequency agile module transmitter 28 and base transmitter 84, and the programmability of the module microcontroller 26 and EEPROM 261. One universal platform design then can be utilized for all applications. In addition, the signal processing module can comprise multiple copies of the input means 22 and the A/D means 24. Cost savings can be achieved by multiplexing at several different points in the input means 22 and the A/D means 24 allowing hardware to be shared among external inputs 12.

After receipt by the input means 22, the external input 12 is inputted to the A/D means 24. The A/D means 24 converts the input to a digital signal 32 and conditions it. The A/D means 24 utilizes at least one programmable A/D converter. This programmable A/D converter may be an AD7714 as manufactured by Analog Devices or similar. Depending upon the application, the input means 22 may also include at least one low noise differential preamp. This preamp may be an INA126 as manufactured by Burr-Brown or similar. The module microcontroller 26 can be programmed to control the input means 22 and the A/D means 24 to provide specific number of external inputs 12, sampling rate, filtering and gain. These parameters are initially configured by programming the module microcontroller 26 to control the input means 22 and the A/D means 24 via input communications line 35 and A/D communications line 36 based upon the input characteristics and the particular application. If the application changes, the A/D converter is reconfigured by reprogramming the module microcontroller 26. In this manner, the input means 22 and the A/D means 24 can be configured to accept analog inputs of 4-20 mA, +/−5 volts, +/−15 volts or a range from +/−microvolts to millivolts. They also can be configured to accept digital inputs, for detection of contact closure, for example.

The module microcontroller 26 controls the operation of the signal processing module 16. In the present invention, the module microcontroller 26 includes a serial EEPROM 261 but any nonvolatile memory (or volatile memory if the signal processing module remains powered) can be used. The EEPROM 261 can also be a separate component external to the module microcontroller 26. Advantageously, the module microcontroller 26 may be PIC16C74A PIC16C74B or a PIC16C77 both manufactured by MicroChip, or an Amtel AT90S8515 or similar. The module microcontroller 26 is programmed by the external programming means 60 through the connector 64 or through radio frequency signal from the base station 40. The same module microcontroller 26, therefore, can be utilized for all applications and inputs by programming it for those applications and inputs. If the application or inputs change, the module microcontroller 26 is modified by merely reprogramming. The digital signal 32 is inputted to the module microcontroller 26. The module microcontroller 26 formats the digital signal 32 into a digital data stream 34 encoded with the data from the digital signal 32. The digital data stream 34 is composed of data bytes corresponding to the encoded data and additional data bytes to provide error correction and housekeeping functions. Advantageously, the digital data stream 34 is organized in data packets with the appropriate error correction data bytes coordinated on a per data packet basis. These packets can incorporate data from a single input channel or from several input channels in a single packet, or for some applications may advantageously include several temporally differing measurements of one or a plurality of input channels in a single packet. The digital data stream 34 is used to modulate the carrier frequency generated by the transmitter 28.

The module transmitter 28 is under module microcontroller 26 control. The module transmitter 28 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 34 is used to frequency modulate the carrier frequency resulting in the radio frequency signal 18 which is then transmitted through the module antenna 20. The generation of the carrier frequency is controlled by the module microcontroller 26 through programming in the EEPROM 261, making the module transmitter 28 frequency agile over a broad frequency spectrum. In the United States and Canada a preferred operating band for the carrier frequency is 902 to 928 MHz. The EEPROM 261 can be programmed such that the module microcontroller 26 can instruct the module transmitter 28 to generate a carrier frequency in increments between 902 to 928 MHz. as small as about 5 to 10 KHz. In the US and other countries of the world, the carrier frequency may be in the 2400 to 2483.5 MHz. band, 5.725 to 5.875 GHz. band, or the 24.0 to 24.25 GHz. band, or other authorized band. This allows the system to be usable in non-North American applications and provides additional flexibility.

The voltage controlled crystal oscillator (not shown) in the module transmitter 28, not only provides the reference frequency for the module transmitter 28 but, advantageously also, provides the clock function 38 for the module microcontroller 26 and the A/D means 24 assuring that all components of the signal processing module 16 are synchronized. An alternate design can use a plurality of reference frequency sources where this arrangement can provide certain advantages such as size or power consumption in the implementation.

The module receiver 29 in the signal processing module 16 receives RF signals from the base station 40. The signals from the base station 40 can be used to operate and control the signal processing module 16 by programming and reprogramming the module microprocessor 26 and EEPROM 261 therein.

The base station 40 has a base antenna 42 through which RF signals 18 are received. Base microcontroller 86 controls the operation of the base station 40 including base receiver 80, base transmitter 82, and base power supply 88. Base receiver 80 receives the RF signal 18 from base antenna 42. The base receiver 80 demodulates the RF signal 18 and the base microcontroller 86 removes any error correction and performs other housekeeping tasks. The data is then downloaded through connector 64 to the external programming means 60 or other personal computer (PC) or data storage/viewing device for viewing in real time, storage, or analysis.

Figure 4:
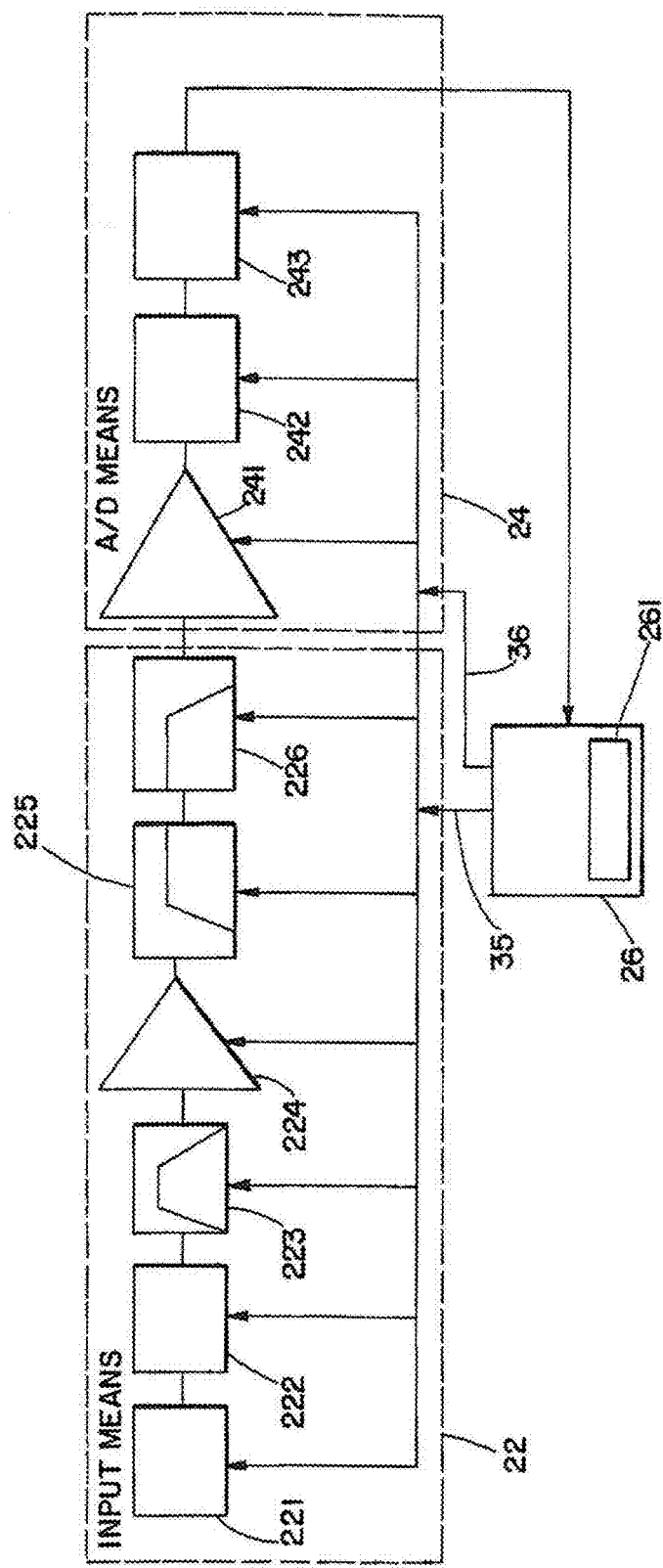
FIG. 4 Block diagram of an embodiment of a base station of part of the diagnostic device of the sleeping disorder treatment system of the present invention.

Referring now to FIG. 4, there is shown a block diagram of the input means 22 and A/D means 24 of the signal processing module 16, which provides for the data acquisition function of the present invention. The signal processing module 16 is variably configurable through software programming initiated by the external programming means 60 to the EEPROM 261 of the microcontroller 26. The variable configurability enables the signal processing module 16 to receive external inputs 12 having different characteristics and ranges and to provide variable sampling rate, filtering and gain of the external inputs 12 based upon such characteristics and range and/or the specific application. For example, if the present invention is utilized in a biomedical environment, EEG diagnosis and monitoring for instance, the sampling rate will need to be much higher than it would be for an industrial setting measuring thermocouple readings. The ability to reconfigure the system for varying signal characteristics arises at three separate levels in the present invention. For maximum flexibility, such reconfiguration can be carried out during a series of measurements by means of the wireless link, which is understood in this context to be bidirectional. Depending on the characteristics of the received signal 18, the base station 40 can command the signal processing module 16 to reconfigure the input means 22 and/or A/D means 24 to accept an external input 12 of larger amplitude, or a different frequency range, where signal characteristics change significantly during the course of a series of measurements. Alternatively, for cost, size, and power advantages, this adjustment could be carried out prior to a series of measurements, with the configuration information stored in memory in the signal processing module 16, where this memory is advantageously implemented in a nonvolatile form such as EEPROM 261, allowing the configuration information to be retained, for instance, across power outages and obviating the need for module receiver 29 and base transmitter 84, saving cost. A third alternative, which provides advantages in certain technical parameters, is to arrange the implementation of the signal processing module 16 such that minor changes in component values or parameters can reconfigure the same basic hardware to accept widely divergent external input 12 types. This reconfiguration could take place at the factory, providing cost and inventory advantages to the manufacturer, or it could be performed by the end user, providing similar cost advantages to the user in allowing one piece of equipment to perform multiple tasks.

A number of configurable components are shown in FIG. 4. Any given component of this arrangement, though, may be omitted, and, in some cases, the order of the components may be changed to gain certain advantages such as physical size, power consumption, or cost, without changing the basic spirit of the invention. Components in this FIG. 4 may be combined, either by having a single component carry out the function of two or more of the components shown or by combining functions within a single package such as an integrated circuit or hybrid module. Certain components may also operate with a fixed configuration, limiting the flexibility of certain parameters while retaining the advantages of configurability in other components.

The external input 12 inputs to the input protection network 221, which protects the signal processing module 16 against damage caused by faults or unanticipated conditions encountered at the external inputs 12. Depending on the rigors expected to be encountered in any given application and the tolerance to size and weight, the input protection network 221 may be omitted, may consist of a simple resistor network, or may include more elaborate protection such as diodes, zener diodes, transorbs, gas discharge tubes, and other components commonly known to those of ordinary skill in the art. Typically, the input protection network 221 is not configurable but its configurability in the present invention provides advantages in certain applications. Configuration options can include adjustable limits on input voltage and/or current as well as rates of change of those parameters, and other electrical parameters as well. These configuration changes can be achieved by changes to component values on a common platform for smallest size, or can be changed under processor control by means of various switches such as relays. A signal within normally expected ranges passes essentially unchanged to the measurement type means 222.

The measurement type means 222 allows selection of the external input 12 configuration. The measurement type means 222 may be used to configure the input circuitry to accept external inputs 12 which are single-ended voltage (a voltage with respect to a common reference shared between several signals), differential voltage (voltage between two defined conductors), differential current (current flowing through a conductor), single-ended current (current flowing to a common reference), frequency, capacitance, inductance, resistance, impedance, conductivity, or any other electrical parameter. The measurement type means 222 converts the external input 12 to a common parameter such as voltage or current, which can be interpreted by the succeeding blocks regardless of the original type of external signal 12 measured. One input channel can be built with several different measurement type means, which can be selectively enabled by means of an analog switch, such as that found in the AD7714 chip in the present invention. It is understood that the AD7714 chip can provide many of the functions of the A/D means 24 and the input means 22 thus reducing the overall size of the signal processing module 16. In the preferred embodiment, the output of the measurement type means 222 is a varying voltage carrying the information which was present in the original signal, or in certain cases, a series of voltage measurements, which are then conveyed to the prefilter 223.

The prefilter 223 allows rejection of external inputs 12 of large signals which are outside the frequency band of interest, so that such signals do not saturate the low-noise preamplifier 224. The prefilter 223 can be advantageously arranged to be a relatively simple filter to provide cost, size, and power advantages, because it need only reject out of band signals to the extent necessary to protect the low-noise preamplifier 224. A typical application might use a simple "R-C" filter to reject offset voltages in an AC-coupled application, or to reject extremely high frequencies which fall well beyond the frequency band of interest, or a combination of the two. Configurability of this section can be limited to simply enabling or bypassing the prefilter 223, or may be more elaborate in allowing selection of cutoff frequencies. In the preferred embodiment this prefilter consists of a simple RC filter which can be bypassed under firmware control, to minimize noise injection; however, an alternate embodiment could incorporate electrically adjustable components such as electronic potentiometers or varactors to provide even more flexibility at the expense of size and noise injection. The prefiltered signal is then passed to the low-noise preamplifier 224.

The low-noise preamplifier 224 is advantageous in certain applications to allow application of gain to the external input 12 early in the signal chain, before significant noise is introduced by the inherent characteristics of certain components, such as thermal noise. Configurability of the gain applied at this step provides an advantage in allowing the present invention to accept larger external inputs 12 using a low gain (unity gain or lower), or alternatively to accurately measure very small external inputs 12 with minimal noise by using higher gain. This gain can be selectively chosen to be either a fixed value or unity gain under processor control by means of the signal selector built into the AD7714 used in the preferred embodiment, or can be designed to allow a selection of one of several gains by means of analog switches combined with a plurality of gain setting resistors. Gain applied at this stage has the net effect of dividing any downstream noise by the gain factor applied here. This more robust signal output by the preamplifier 224 is then passed to the AC coupling filter 225.

The AC coupling filter 225 is a highpass filter used to allow the system to reject the DC offset or steady state value of an external input 12 wherein the offset is not of interest, allowing additional gain to be applied to the changes in the external input 12. For instance, bioelectric signals such as EEG, EMG, or ECG are normally of interest only for the changes in those signals, and the absolute offset level is not of interest for diagnostic purposes. The cutoff frequency may be configured to allow adjustment of various parameters such as settling time, or may be adjusted to zero to effectively bypass the AC coupling filter 225. In the preferred embodiment, the filter may be bypassed by use of the signal selector switch in the AD7714; however, the use of adjustable components such as electronic potentiometers or varactors would allow more flexibility in choosing the cutoff frequency, at the expense of size and power consumption. The resulting signal, now stripped of any interfering DC offset if so configured, is then passed to the antialias filter 226.

The antialias filter 226 is a lowpass filter required to guard against false signals caused by aliasing between external input 12 content and sampling rate of downstream sampling functions such as multiplexing or analog-to-digital conversion. The Nyquist sampling theorem shows that any frequency content in the sampled signal which is higher than one-half the sampling rate of the sampling function will cause aliasing, which results in false signals. In practice the antialias filter 226 is more commonly set to a smaller fraction of the sampling rate, usually between ¼ and ¹/₁₀ the sampling rate. Regardless of the rate or ratio used, the cutoff frequency of the antialias filter 226 must change when the sampling rate changes significantly, to retain the most advantageous ratio of the sampling rate to the filter passband. The programmable cutoff frequency of the antialias filter 226 is thus required to allow for variable sampling rates. In the preferred embodiment, the high sampling rate of the delta sigma modulator in the AD7714 permits the use of a simple fixed RC type filter, with the antialias filtering begin provided as an inherent digital filter in the AD7714; however, an alternate embodiment might use a switched capacitor filter such as the MAX7409 or other filter with a programmable cutoff frequency. The resulting filtered signal is then conveyed to the programmable gain amplifier 241 in the A/D means 24.

The programmable gain amplifier 241 adjusts the external input 12 amplitude to match the amplitude accepted by the A/D converter 242. In the preferred embodiment this programmable gain amplifier is included in the AD7714 integrated circuit, but this function could also be provided with a dedicated programmable gain amplifier, or alternatively through the use of analog switches or adjustable components such as potentiometers or DACs. If too much gain is applied, the programmable gain amplifier 241 itself or downstream components will saturate, introducing severe distortion and usually rendering the external input 12 immeasurable. If, on the other hand, insufficient gain is applied here, the quantization noise of the analog-to-digital conversion process comes to dominate the external input 12, causing a severe degradation in the signal-to-noise ratio. For instance, a typical 16-bit A/D converter 242 can distinguish between $2^{16}$ or 65536 distinct levels. With an A/D converter 242 input range of +/−3 volts, each level represents 92 µV. If insufficient gain is applied to the external input 12 such that the total signal swing is only 200 µV, the A/D converter 242 will convert at most three distinct levels, rendering fine features of the external input 12 totally illegible. The module microcontroller 26 therefore adjusts the gain applied in the programmable gain amplifier 241 such that the expected external input 12 as processed and filtered by the preceding elements as described above, is amplified to cover as much of the A/D converter 242 input range as practical, or some other gain which optimizes signal features of interest. Additionally, in some applications it is advantageous to have the module microcontroller 26 adjust this gain dynamically depending upon the actual measured external input 12. For instance, the module microcontroller 26 might increase the programmable gain amplifier 241 gain when a measured external input 12 is very small, and then decrease the gain to avoid saturation when the external input 12 amplitude increases. This automatic gain control provides an increase in the total dynamic range achievable by the system without requiring expensive, large, and power-hungry components such as very high resolution A/D converters 242. The signal resulting from application of the specified gain is then passed to the A/D converter 242.

At least two parameters of a typical A/D converter 242 can be readily adjusted to achieve various goals as the situation dictates. First, the sampling rate may be adjusted to balance the conflicting goals of high fidelity measurements and low digital data rate. Where a signal has no high frequency content of interest, the sampling rate may be adjusted to a very low rate to minimize the demands on downstream processes such as digital filtering or telemetering of the data. On the other hand, sampling an external signal 12 with significant high-frequency content of interest demands a higher sampling rate. In the preferred embodiment, the sampling rate is programmable via the AD7714; in other implementations the sampling rate can be made adjustable by means of an externally applied sampling clock to an A/D converter. The adjustable sampling rate allows the controller to adapt the A/D converter 242 to best meet the system demands of the moment.

In a similar fashion, selection of the resolution provided by the A/D converter 242 must balance faithful reproduction of the external input 12 against total digital data rate. Depending on the particular A/D converter 242 used, there may also be a tradeoff of the maximum achievable sampling rate against the selected resolution, wherein selection of a higher resolution lowers the maximum attainable sampling rate. Again the module microcontroller 26 can adjust this parameter to best meet the system requirements, selecting higher resolution when smaller changes in the measured signal amplitude must be reported, and lower resolution when the lack of such a requirement allows advantages in the form of either a higher sampling rate or a lower digital data rate. In the preferred embodiment, the AD7714 can be programmed to either 16 bit or 24-bit resolution, and the firmware running in the microcontroller can selectively transmit 8, 12, 16, or 24 bits of the acquired data. The digital filter 243, the module microcontroller 26, or other downstream process can also reject certain portions of the digital data stream to provide an effective decrease in resolution where this decrease is advantageous, especially when the data must later cross a bandwidth-limited link such as a RF, IR or optical link. The A/D converter 242 passes the signal, now in the form of a succession of digital values, to the digital filter 243 for further processing.

The digital filter 243 extracts external input 12 parameters of interest while rejecting other signals, commonly referred to as noise. Implementation of the digital filter 243 could alternatively be in the form of analog filters applied anywhere in the signal chain prior to the A/D converter 242, but implementation as a digital filter 243 provides advantages as to programmability, calibration, drift, and accuracy. The digital filter 243 could be implemented in many forms, depending upon the demands of the particular application. In the preferred embodiment, the digital filter is inherent in the analog to digital conversion process inside the AD7714, but it is understood that the digital filter 243 could be implemented as firmware inside the module microcontroller 26 itself, or as a digital signal processor, or as a specialized integrated circuit, or by some other means. Regardless of implementation, the programmability of the digital filter 243 allows the system to readily adapt to changing measurement requirements, whether those changes are brought about by changes in the environment, changes in the external input 12 itself, or changes in the focus of the overall system. The resulting output from the digital filter 243 is a stream of digital values, ready for further processing such as assembly into the desired format for transmission by the firmware.

Figure 5:
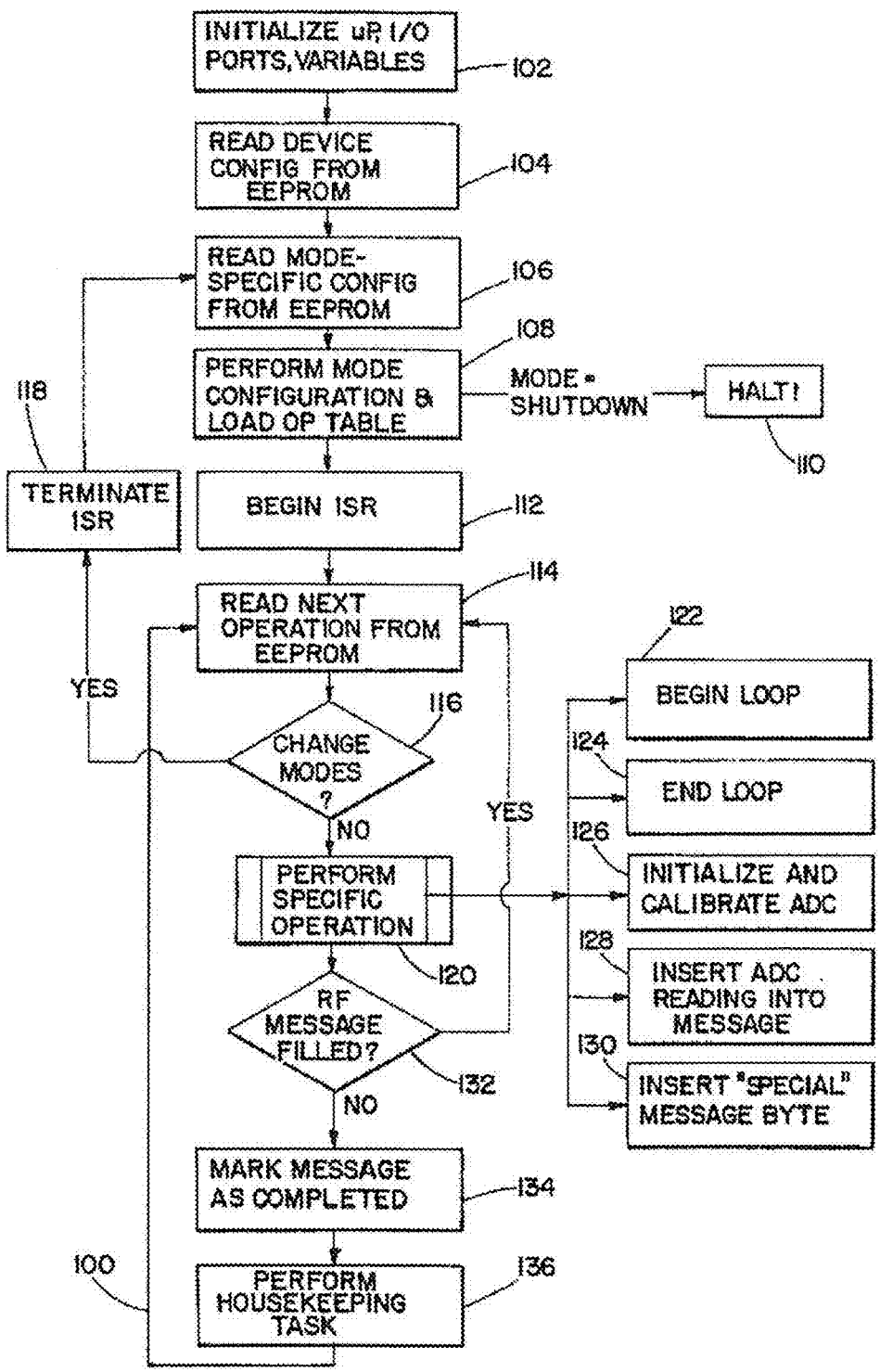
FIG. 5 Block diagram of an embodiment of the programming firmware in the signal processing module of part of the diagnostic device of the sleeping disorder treatment system of the present invention.

Referring now to FIG. 5 there is shown a block diagram of the firmware of the present invention. The signal processing module 16 firmware defines several modes of operation 100. There are several "test" modes which are used during factory calibration of the device. In addition, there are several operation modes which have mode-specific configuration. For example, the signal processing module 16 can be programmed to operate in a first operational mode in which it transmits calibration data (used to properly zero the analog inputs) for the first three seconds of operation (or for some other predetermined time), and then switches to a second operational mode which transmits analog signal information as collected from the A/D converters 242. The configuration for each mode of operation is programmed in the non-volatile memory EEPROM 261.

Once power is first applied to the signal processing module 16, the module microcontroller 26 performs the basic device initialization, including proper configuration of the I/O ports and internal variables 102. Next, the module microcontroller 26 reads the initial device configuration 104 from the EEPROM 261. This configuration controls the input means 22 of the signal processing module 16, including the number of external inputs (also herein referred to as channels), the resolution of the A/D converter 242, and the sampling rate of each individual input channel. This configuration also controls the operation of the module transmitter 28 in the signal processing module 16, including the carrier frequency, modulation type, output power control, and the length in bytes of each transmitted RF message packet. This configuration also describes the initial mode of operation for the signal processing module 16.

Once the initial configuration has been read, the module microcontroller 26 enters the first mode of operation described in the configuration. It reads the mode-specific configuration 106, which includes the state of the module transmitter 28 and the analog inputs as used in the mode. This configuration can reside in EEPROM 261 or in module microcontroller 26 memory. The module microcontroller 26 then initializes all the peripheral devices according to this mode configuration 108. In the special case that this is the "shutdown" mode, the module microcontroller 26 will perform a software power-down 110.

Once the mode has been initialized, the module microcontroller 26 begins execution of the interrupt service routine (ISR) 112, which is responsible for transmitting the data in the form of messages along the modulated RF carrier. Operation of the interrupt service routine is asynchronous and distinct from the mainline code, and is described later.

The module microcontroller 26 begins execution of the mode-specific "opcodes" 114, which are a sequence of instructions contained either in EEPROM 261 or in the module microcontroller 26 memory. These opcodes are performed for each operational mode. The module microcontroller 26 reads the first operational code from the EEPROM 261 and interprets the opcode, performing an appropriate action: If the opcode instructs the module microcontroller 26 to change modes 116, the module microcontroller 26 terminates the ISR 118 and returns to the mode initialization, and begins execution of a new operational mode; if the opcode instructs the module microcontroller 26 to begin a loop construct 120, the module microcontroller 26 begins the loop by initializing a loop counter variable 122; if the opcode instructs the module microcontroller 26 to end a loop construct, the module microcontroller 26 increments the loop counter variable and determines if the loop is complete 124. If not, the module microcontroller 26 resets the index of current opcode to the beginning of the loop, otherwise it sets the index of the next opcode to after the loop; if the opcode instructs the module microcontroller 26 to initialize a single A/D converter 242, the module microcontroller 26 will perform the specified calibration 126; if the opcode instructs the module microcontroller 26 to the read a single A/D converter 242, the module microcontroller 26 will take the reading and insert the data into the current message to be transmitted over the RF carrier 128; if the opcode instructs the module microcontroller 26 to insert a special byte of data into the RF message, the module microcontroller 26 will insert this data into the message 130. This special message byte may include an identifier to uniquely identify the signal processing module 16, an error check field such as a cyclic redundancy check, or some data representing the internal state of the signal processing module 16 such as the RF frequency, measured temperature, etc.

After each opcode has been read and interpreted, the module microcontroller 26 determines if the RF message has been completely filled and is ready to be transmitted over the RF carrier 132. If it has, the module microcontroller 26 marks a flag variable for the interrupt service routine to begin transmitting the RF message 134.

Next, the module microcontroller 26 performs any housekeeping tasks, such as updating the RF tuning parameters based on changes in temperature, updating timers, etc. 136. Finally, the module microcontroller 26 returns to execute the next opcode in the sequence 114.

Figure 6:
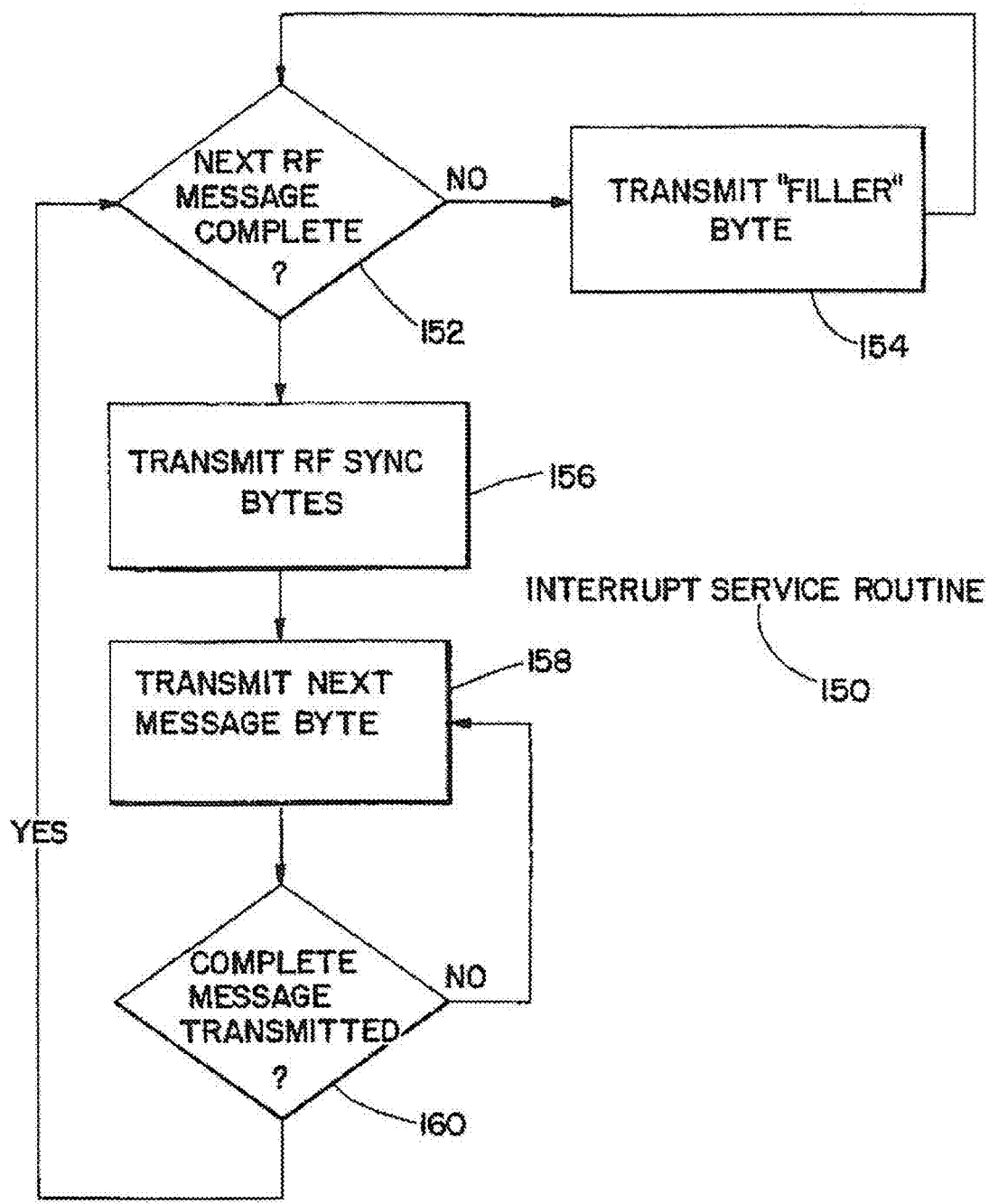
FIG. 6 Block diagram of an embodiment of the programming of the interrupt service routine in the firmware in the signal processing module of part of the diagnostic device of the sleeping disorder treatment system of the present invention.

Referring now to FIG. 6 there is shown a block diagram of the software programming function of the ISR 150. The ISR is responsible for transmitting the individual message bytes over the RF carrier. The ISR is executed by a hardware interrupt which occurs immediately before every byte to be transmitted over the RF carrier. The ISR detects whether an RF message is completely filled 152. If the ISR detects (based on the flag variable) that an RF message is not yet completely filled by the main code, the ISR transmits a "filler" byte, or a byte with an even number of "1" and "0" bits 154. This acts to maintain an even (50%) modulation duty cycle on the carrier frequency.

Once the ISR detects that the main code has filled an RF message to be transmitted, it transmits the RF sync bytes 156. These are two unique bytes transmitted at the beginning of every RF message which are easily identified by the base station 40 as the start of a message.

Once the RF sync bytes have been transmitted, the ISR transmits each message byte of the RF message, in sequence 158. Once the RF message has been completely transmitted 160, the ISR resumes transmitting filler bytes until the next RF message is filled by the main code.

Because of the phase locked loop based frequency synthesizer used in the present invention, the module transmitter 28 and base transmitter 84 are frequency agile over the frequency range. Since the module receiver 29 and the base receiver 80 employ automatic frequency control, the present invention consumes relatively low power as the module transmitter 28 and base transmitter 84 can be intermittently powered down without loosing reception due to drift or sacrificing data transmission accuracy. The utilization of programmable firmware allows inexpensive and flexible operation for the inputting, conditioning and processing of any type, character and range of the external inputs. This also allows the module microcontroller 26, in response to the variation of the external inputs 12 or, in response to instructions received by RF signal through the module receiver 29, to adapt the signal processing module 16 based upon the variations allowing the signal processing means 16 to input, condition, process and transmit said external input notwithstanding said variation. The present invention performs this adaptation without the need to modify or alter hardware or select or use different hardware already present in the device. In other words all adaptation can be accomplished by software programming totally.

One or more sensors are used to develop the data or signals used in the present invention for determining a quantitative level of severity of a subject's sleeping disorder and/or symptoms. In various embodiments, preferably at least two EEG electrodes are used to develop this data. In other embodiments, preferably, at least two ECG electrodes are used. In still other embodiments, preferably a pulse oximeter is used. In still even other embodiments, preferably, either an $O_2$ or $CO_2$ blood gas monitor is used.

The signals from the one or more sensors used in various embodiments of the present invention are preferably analyzed using a processor and software that can quantitatively estimate or determine the severity of the subject's sleeping disorder or symptoms. Using either the microcontroller 26 of a data acquisition system, a separate computer, base station or processor, a PDA, a processor on a device for treating the subject's sleeping disorder or a combination of these processors, the severity of the subject's sleeping disorder and/or symptoms is determined and is used at least in part to regulate the physical or chemical treatment of the subject. Also optionally, the one or more sensors used in the system of the present invention can also be tethered to a computer, base station, cell phone, a PDA or some other form of processor or microprocessor.

The processor or microprocessor of various embodiments of the present invention can be part of a remote communication station or base station. The remote communication station or base station can also be used only to relay a pre- or post-processed signal. Preferably, the remote communication station or base station can be any device known to receive RF transmissions such as those transmitted by the wireless data acquisition system described herein. The remote communication station or base station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device including the subject's treatment device. Further optionally, two different remote communication stations can be used, one for receiving transmitted data and another for sending data. For example, with the sleep diagnosis and treatment system of the present invention, the remote communication system of the present invention can be a wireless router, which establishes a broadband internet connection and transmits the physiological signal to a remote internet site for analysis, preferably for further input by the subject's physician or another clinician. Another example is where the remote communication system is a PDA, computer or cell phone, which receives the physiological data transmission, optionally re-processes the information, and re-transmits the information via cell towers, land phone lines, satellite, radio frequencies or cable to a remote site for analysis. Another example is where the remote communication system is a computer or processor, which receives the data transmission and displays the data or records it on some recording medium, which can be displayed or transferred for analysis at a later time.

The quantitative method for estimating or determining the severity of the subject's sleeping disorder or symptoms is preferably accomplished by using signals or data from the one or more sensors described herein. More preferably, this quantitative method is accomplished in real-time, allowing the subject's symptoms to be treated as they occur. By real-time it is meant that the quantitative diagnosis step is accomplished predictively or within a short period of time after symptoms occur which allows for immediate treatment, thereby more effectively reducing the health affects of such disorder while at the same time also minimizing side effects of the treatment chosen. By real-time, preferably the diagnosis is accomplished within 24 hours of receiving the signals from the one or more sensors on the subject, more preferably within 8 hours, even more preferably within 4 hours, still even more preferably within 1 hour, still even more preferably within 20 minutes, still even more preferably within 5 minutes, still even more preferably within 1 minute, still even more preferably within 10 seconds, still even more preferably within 1 second, still even more preferably within 0.1 seconds and most preferably within 0.01 seconds.

Figure 7:
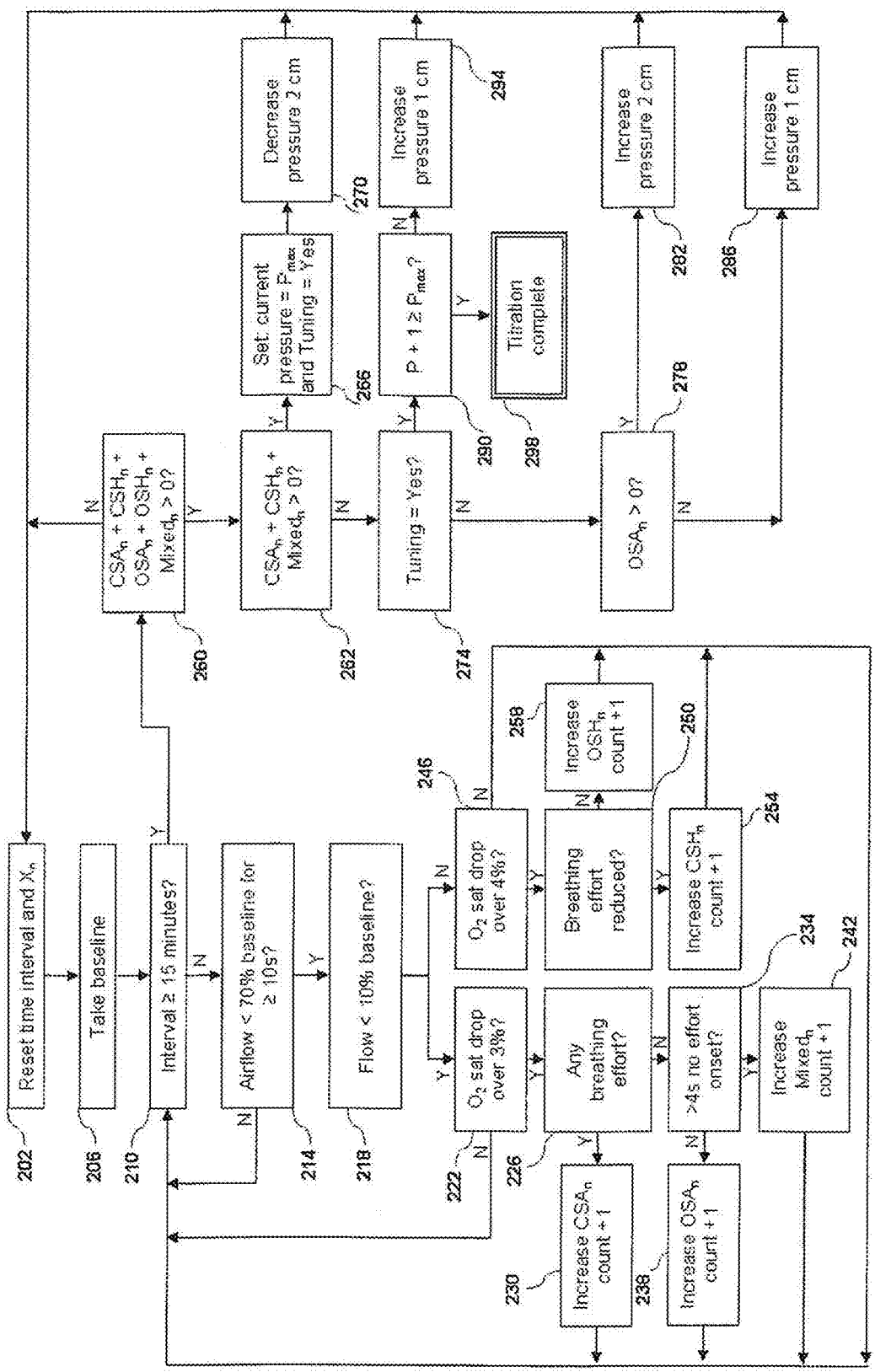
FIG. 7 Flowchart of one embodiment of the sleep disorder treatment system of the present invention showing analysis of the physiological signals and adjustment of the treatment device.

FIG. 7 shows a flow diagram of one example titration algorithm that adjusts the pressure of a CPAP device based on at least the measured airflow, respiratory effort, and blood oxygen concentration. The algorithm in FIG. 7 consists of a counting phase and an adjustment phase. The adjustment phase operates in titration mode, during which large pressure adjustments are made, and tuning mode, during which fine pressure adjustments are made to establish the optimum air pressure.

First, a time interval and all event counters are reset 202. The system then establishes a baseline 206, which is used for comparisons throughout the time interval. If the time interval has elapsed 210, the system evaluates the event counters and makes adjustments as necessary. The time interval 210 in FIG. 7 is shown as 15 minutes, but any time period may be suitable. For example, early in the titration phase, smaller intervals of 5 minutes may be more appropriate, while later in the titration phase intervals of 30 minutes or more may be used.

If the time interval has not elapsed 210, the subject's airflow is compared to the baseline 214. If the subject's current airflow drops below 70% of the baseline for 10 seconds or more 214, the system evaluates the effects of a severe reduction in airflow. If the airflow drops to below 10% of the baseline 218, the decrease in airflow may indicate an instance of apnea. In this situation, the subject's oxygen saturation is compared to the baseline 222. If the subject's oxygen saturation has not decreased more than 3% 222, the decrease in airflow is not an event at all, and the system returns to monitoring the subject's airflow 210. If the subject's oxygen saturation does decrease more than 3% 222, the system checks for a breathing effort 226. If the subject is attempting to breathe, the event is considered an obstructive sleep apnea (OSA), and the $OSA_n$ count is increased by one 230. The system then returns to monitoring the subject's airflow 210. If, however, the subject is not attempting to breathe, the system continues to look for breathing effort 226. If the subject does not attempt to breathe for more than 4 seconds 234 the event is considered a central sleep apnea (CSA), and the $CSA_n$ count is increased by one 238. The system then returns to monitoring the subject's airflow 210. In contrast, if the subject does attempt to breathe within 4 seconds 234 the event is considered a mixed sleep apnea, and the $Mixed_n$ count is increased by one 242. The system then returns to monitoring the subject's airflow 210.

Returning to the airflow comparison 218, if the subject's airflow is reduced to 70% of the baseline for 10 seconds or more, but the airflow does not drop to 10% of the baseline, the system evaluates the effects of a mild reduction in airflow. If the airflow does not drop to below 10% of the baseline 218, the mild decrease in airflow may indicate an instance of hypopnea. In this situation, the subject's oxygen saturation is compared to the baseline 246. If the subject's oxygen saturation has not decreased more than 4% 246, the decrease in airflow is not an event at all, and the system returns to monitoring the subject's airflow 210. If the subject's oxygen saturation does decrease more than 4% 246, the system checks for a breathing effort 250. If the subject is attempting to breathe, the event is considered an obstructive sleep hypopnea (OSH), and the $OSA_n$ count is increased by one 258. The system then returns to monitoring the subject's airflow 210. If, however, the subject is not attempting to breathe, the event is considered a central sleep hypopnea (CSH), and the $CSH_n$ count is increased by one 254. The system then returns to monitoring the subject's airflow 210.

The system continues to monitor the subject throughout the time interval 210. After the time interval is over, the system evaluates the subject's condition and calculates the next change in pressure. If the pressure should be adjusted 260, an adjustment algorithm is applied. In FIG. 7, the system looks for any event 260, but in other embodiments of the present invention the system could evaluate only a few variables, for example the number of CSA events. Optionally, the system could evaluate the ratio of counted events, changes in the number of events between timeperiods, or any other condition capable of being recorded or calculated by the system. In FIG. 7, If no events have been detected (i.e., all event counters $OSA_n$, $CSA_n$, $OSH_n$, $CSH_n$, and $Mixed_n$ are 0) 260, the subject's condition is acceptable, and no treatment changes are required. The system then returns and resets the time interval and all event counters $OSA_n$, $CSA_n$, $OSH_n$, $CSH_n$ and $Mixed_n$ 202. At this point, the system is also capable of recording the previous counter values, recording the total number of events, and the like. In this way, the system can compare the subject's status between intervals. For example, the subject's status during the first time interval can be compared to the status during the current or final interval, or the subject's status can be evaluated over consecutive intervals. Such comparisons can provide information on, for example, trends, and overall effectiveness of the treatment.

If an adjustment is appropriate 260, the system determines if any central or central-based events have occurred 262. If the subject has experienced a central sleep apnea, central sleep hypopnea, or mixed apnea event, the system sets the current pressure as a maximum threshold, and sets a flag to initiate the tuning phase of the titration 266. The new maximum pressure $P_{max}$ is the highest value of pressure that the system can now attain. Under no circumstances will the system automatically increase the air pressure beyond $P_{max}$, although in some embodiments the pressure could be manually adjusted above the maximum value. After setting the maximum pressure and initiating the tuning mode, the system decreases the CPAP pressure by 2 cm $H_2O$ 270. The system then returns and resets the time interval and all event counters $OSA_n$, $CSA_n$, $OSH_n$, $CSH_n$ and $Mixed_n$ 202.

If no central or central-based events have occurred, the system checks to see if it is in tuning mode 274. If the system is in tuning mode, and the subject has experienced an obstructive event (but not a central or central-based event) 274, the system compares the result of the next pressure change to the maximum pressure 290 (established previously at 266). If the next pressure increase of 1 cm $H_2O$ will be less than the maximum allowable pressure $P_{max}$ 266, the system increases the pressure by 1 cm $H_2O$. After making the adjustment, the system then returns to the counting phase and resets the time interval and all event counters $OSA_n$, $CSA_n$, $OSH_n$, $CSH_n$ and $Mixed_n$ 202. In contrast, if the next pressure increase will be greater than or equal to the maximum allowable pressure $P_{max}$ 266, the titration is complete. The system no longer adjusts the gas pressure, although it may continue to count the subject's events and record other data through the remainder of the night.

If the system is not in tuning mode 274, the system evaluates if the obstructive events were apneas or hypopneas 278. If the events were apneas, the system increases the gas pressure by 2 cm $H_2O$ 282. If the events were hypopneas, the system increases the gas pressure by only 1 cm $H_2O$ 286. In either case, after adjusting the pressure accordingly, the system then returns and resets the time interval and all event counters $OSA_n$, $CSA_n$, $OSH_n$, $CSH_n$ and $Mixed_n$ 202.

The adjustment algorithm shown in FIG. 7 is relatively simple. More sophisticated calculations and decisions can also be used. For example, the system can evaluate the trends occurring across time periods by considering how the numbers of detected events changes, or the system can use the ratio of central-type events to obstructive-type events to refine the changes in pressure. The system could also, for example, consider the number and type of adjustments previously made. Such a step would prevent system oscillation that can occur near the end of titration as the system attempts to refine the optimal pressure. The system could use a variety of analysis and calculation techniques, including lookup tables, fast-Fourier transforms, wavelet analysis, neural networks, and the like.

Although FIG. 7 depicts control of a CPAP machine, any appropriate treatment device may be used. In this situation, the treatment device control algorithm would be adjusted to consider the capabilities of the treatment device. For example, if the treatment device is a more advanced bi-level PAP machine, the treatment device control algorithm could adjust the inspiration air pressure only. The action taken can also vary. For example, the pressure can be increased by differing amounts depending on the phase of titration, or the number of prior adjustments, or the severity of the breathing events. As further illustration, if the system determines that the subject has an sleep-related breathing disorder that is untreatable with the current treatment device (for example, a CPAP device cannot deliver a sufficiently high pressure, or the treatment device is inappropriate for the subject's condition), the system can shut down or provide a safe pressure for the remainder of the night before recommending another treatment method.

Although the titration phase of FIG. 7 is triggered only by the end of the time interval 210, various other conditions could also require pressure adjustments. For example, if the system detects a severe central apnea event, the gas pressure could be immediately reduced. Similarly, if the system detects several severe apneas in a single time period, the titration phase could begin before the end of the time period. Other safety mechanisms can be programmed into the system as well. For example, the system can be programmed to ignore the sensor signals if the data becomes corrupted (for example, if the sensor becomes disconnected).

Figure 8:
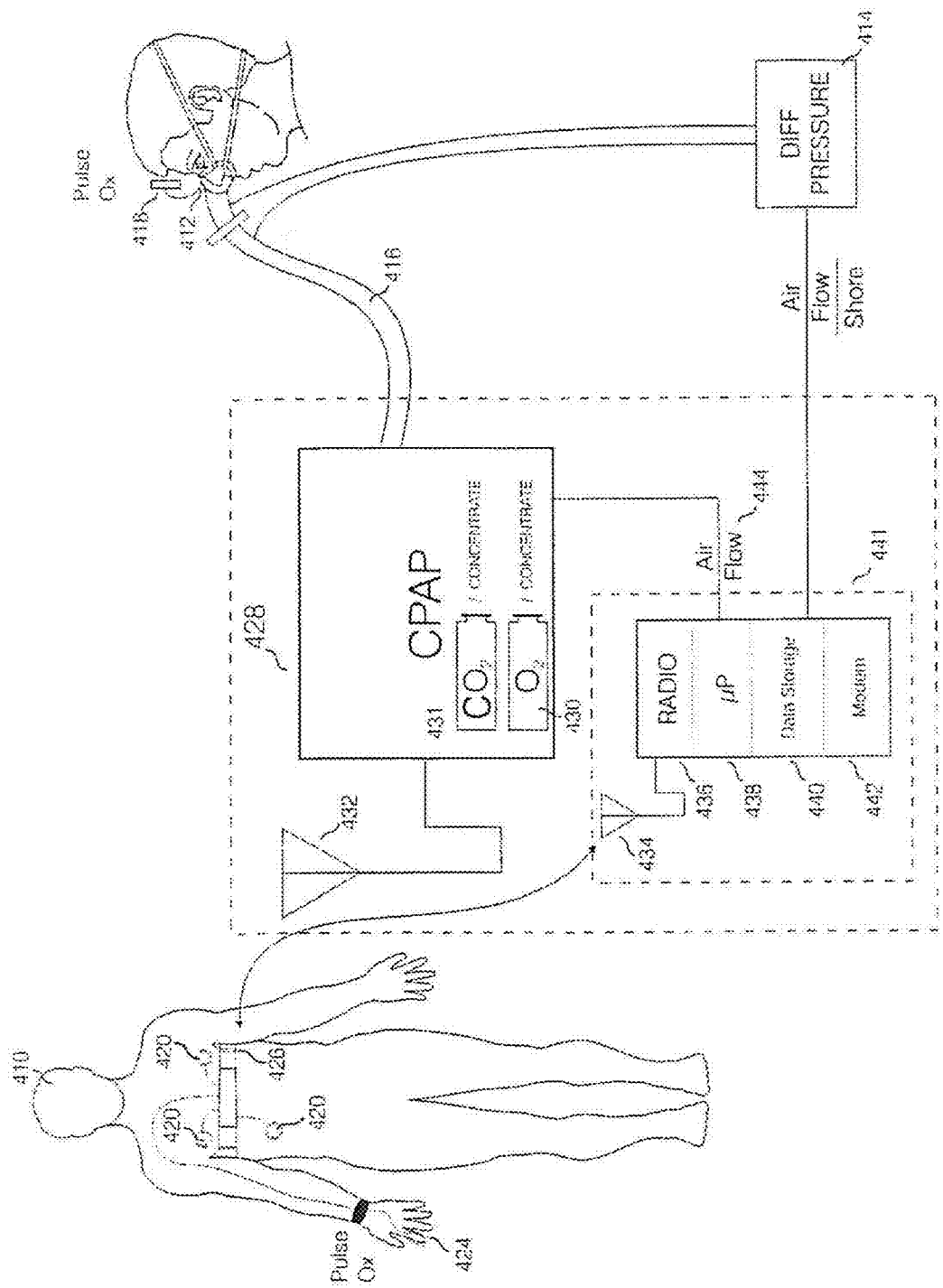
FIG. 8 Schematic view of one embodiment of the sleep disorder treatment system of the present invention.

FIG. 8 shows a schematic view of one embodiment of the sleep disorder treatment system of the present invention. In FIG. 8, a number of sensors 420, 424, 418, and 426 are connected to a subject 410. The subject 410 in this case is a human shown with a respiratory mask 412, which is connected by an air hose or subject circuit 416 to a continuous positive air pressure device 428. In this embodiment, the signal or data from one or more of these sensors is collected by a diagnostic device 441, which comprises a radio 436; an antenna 434; and a microprocessor 438 for processing the data or signals to determine a level of severity of the subject's sleeping disorder or symptoms. The diagnostic device 441 calculates a level of severity for the subject's symptoms and physiological condition. The diagnostic device 441 then transmits a signal based on this level of severity by either a tether 444 or radio signal (not shown) to an actuator (not shown) in the CPAP device 428, which controls the flow of air or gas provided to the subject by the air hose or subject circuit 416. The CPAP device 428 optionally connects to an oxygen tank 430, which can be used to increase the concentration of oxygen in the air being delivered to the subject. Further optionally, the CPAP device 428 connects to a carbon dioxide tank 431, which can be used to increase the concentration of carbon dioxide in the air being delivered to the subject. The CPAP device 428 could connect to both the oxygen tank 430 and the carbon dioxide tank 431, only one of the tanks, or neither. In addition, optionally the treatment device 428 has a sensor in the air hose 416, which can measure the differential pressure 414 and thereby accurately measure air flow provided to the subject. Also optionally, the device can have a nebulizer (not shown) with a reservoir and pump to injecting medication into the nebulizer.

Figure 3:
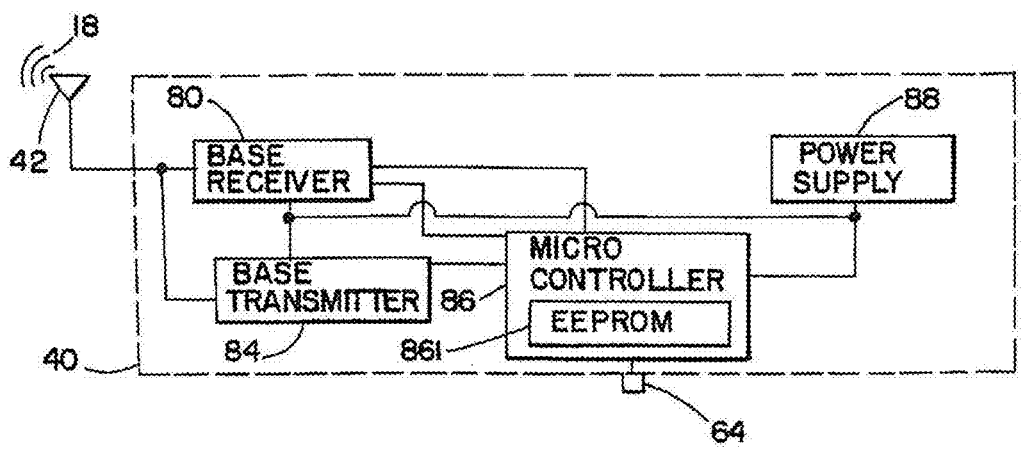
FIG. 3 Block diagram of one embodiment of the base station used in the present invention.
Figure 9:
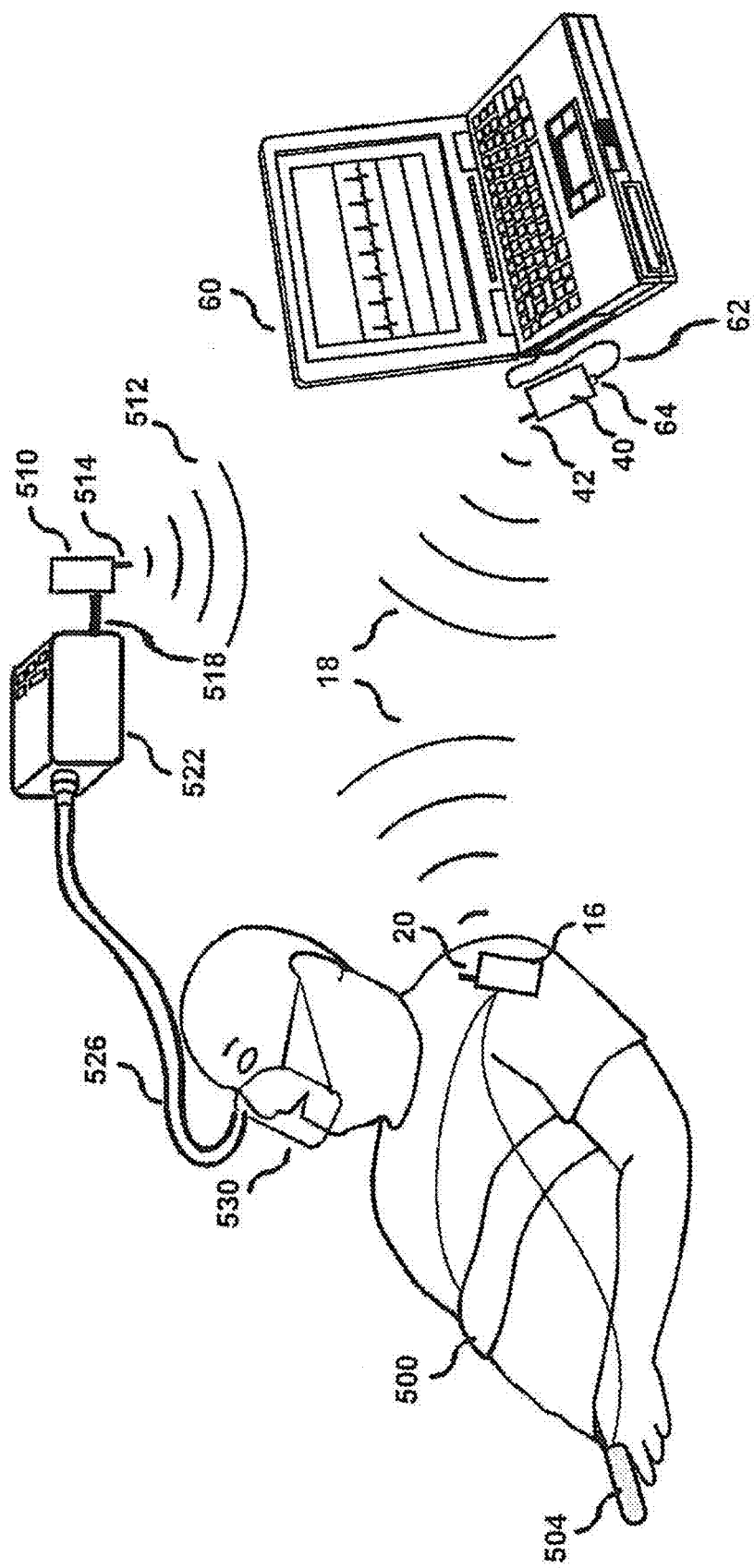
FIG. 9 Schematic representation of one embodiment of the present invention used with a subject to acquire EEG signals from the subject and then transmit them to the receiver and attached computer.

FIG. 9 shows a diagram outlining the treatment titration system in more detail. In FIG. 9, a patient interface box 16 receives signals (not shown) from a respiratory belt 500 and a pulse oximeter 504 placed on the subject. The sensors 500 and 504 can be any of the sensors described herein or known in the art. In a simple embodiment of the present invention, the patient interface box 16 generates a wireless signal 18 encoded with data corresponding to the signals from the respiratory belt 500 and a pulse oximeter 504. The patient interface box 16 transmits the wireless signal 18 to base station 40. In FIG. 9, the wireless signal 18 is shown as radio frequency (RF). In this case, the patient interface box 16 generates a radio frequency signal 18 by frequency modulating a frequency carrier and transmits the radio frequency signal through the module antenna 20. The base station 40 receives the radio frequency signal 18 through base antenna 42, demodulates the radio frequency signal 18, and decodes the data. It is understood that other wireless means can be utilized with the present invention, such as infrared and optical, for example. RF wireless transmission is preferred. Although one module antenna 16 and one base antenna 42 are shown in this embodiment, it is understood that two or more types of antennas can be used and are included in the present invention. An external programming means 60, shown in FIG. 9 as a personal computer, contains software that is used to program the patient interface box 16 and the base station 40 through data interface cable 62. The data interface cable 62 is connected to the base station 40 by connector 64. Instead of a data interface cable 62, the patient interface box 16 and the base station 40 can be programmed by radio frequency (or other type) of signals transmitted between an external programming means and a base station 40 and the patient interface box 16 or to another base station 40. RF signals, therefore, can be both transmitted and received by both patient interface box 16 and base station 40. In this event the patient interface box 16 also includes a module receiver 29 (shown in FIG. 2) while the base station 40 also includes a base transmitter 84 (shown in FIG. 3), in effect making both the patient interface box 16 and the base station 40 into transceivers. In addition, the data interface cable 62 also can be used to convey data from the base station 40 to the external programming means 60. If a personal computer is the external programming means it can monitor, analyze, and display the data in addition to its programming functions. The base receiver 80 and module receiver 29 (shown in FIG. 3 and FIG. 2, respectively) can be any appropriate receivers, such as direct or single conversion types. The base receiver 80 preferably is a double conversion superheterodyne receiver while the module receiver 29 preferably is a single conversion receiver. Advantageously, the receiver employed will have automatic frequency control to facilitate accurate and consistent tuning of the radio frequency signal 18 received thereby.

The external programming means 60 also contains a processor used to calculate the next appropriate gas flow level to be delivered to the subject. In the illustrated embodiment, the external programming means 60 uses data originally collected from the respiratory belt 500 and the pulse oximeter 504 to calculate the appropriate flow level. The external programming means is capable of performing a variety of analysis and calculation techniques, including lookup tables, fast-Fourier transforms, wavelet analysis, use of a neural network, and the like. Optionally, the data processing and calculation can be performed by the base station 40. Further optionally, the processing and calculation can be distributed between the patient interface box 16, the base station 40, and the external programming means 60.

After the appropriate flow level has been calculated, the external programming means 60 transmits a command signal to the treatment device interface 518, which then relays the command signal to the treatment device 522 via a connection 518. In FIG. 9, the external programming means 60 transmits the command signal to the treatment device interface 518 via wireless RF signal 512. The RF signal 512 is received by an RF antenna 514 on the treatment device interface 518. Optionally, the command signal can be transmitted by any other wireless means. Although the command signal transmission 512 is shown in FIG. 9 to be of the same type as the sensor signal transmission 18, this is not necessary. Optionally, the two wireless transmissions can be of different types. Optionally, the command signal can be transmitted from the external programming means 60 by a wired connection to the treatment device interface 518.

The treatment device interface 518 connects to the treatment device 522 with a connector 518. In FIG. 9, the treatment device 522 is shown as a CPAP device, but the treatment device 522 may be any device known in the art for the treatment of sleep-related breathing disorders, including but not limited to a bi-level PAP device, an auto-PAP or auto-CPAP device, an ASV device, and the like. FIG. 9 also shows the connector 518 as a USB connection. Optionally, the treatment device interface 518 can be completely enclosed within the treatment device 522 itself. In this case, the treatment device would be essentially modified to directly receive the command signal from the external programming means 60. Once the treatment device 522 receives the command signal the treatment device performs the command and changes the treatment provided to the subject. In FIG. 9, the treatment device 522 is a CPAP device, which increases or decreases the pressure of the gas delivered to the subject via conduit 526 and mask 530.

Optionally, the treatment device 522 may contain additional sensors. For example, if the treatment device 522 is a CPAP device, it may contain an air flow or air pressure sensor (not shown). If the treatment device 522 contains a sensor, that sensor information would be integrated into the command calculation process. This integration can take place in any of the system components. For example, the treatment device sensor information could be included in a processing step performed within the treatment device 522, at the external programming means or at the base station 40.

Figure 10:
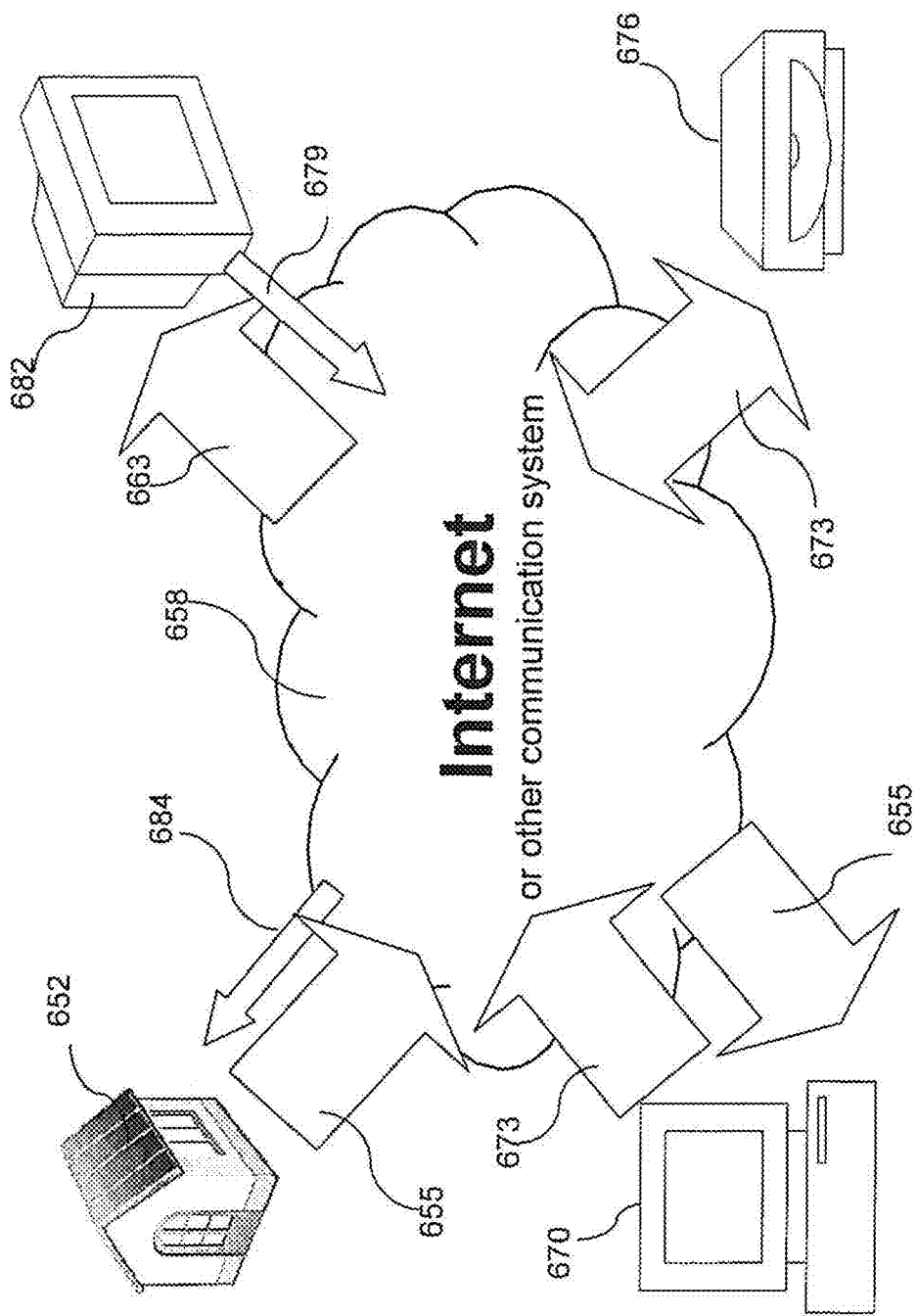
FIG. 10 Schematic representation of one embodiment of the present invention showing the remote data acquisition method.

FIG. 10 is schematic of the remote data acquisition device and system of the present invention. In FIG. 10, a wireless data acquisition system 50 is used to receive, filter, and optionally analyze signals 27 from sensors (not shown) on a subject (not shown). The wireless data acquisition system 50 transmits a signal based, at least in part, on one or more of the signals from the sensors on the subject. The data acquisition system 50 transmits a signal 55 preferably in real time from the subject's home 52 to a server 70 for analysis. The signal 55 is transmitted over the internet or other communication system 58. Such other communication systems include satellites, cellular networks, local area networks (LAN), other wide area networks (WAN), or other telecommunications system. If the signal 55 is transmitted over the internet 58, preferably the signal 55 is transmitted using a cellular card provided by cellular providers such as for example Sprint, Cingular, AT&T, T-Mobile, Alltel, Verizon or the like. The signal 55 that is transmitted over the internet or other communication system 58 can be compressed to provide better resolution or greater efficiency. The server 70 performs data analysis (not shown). The analyzed data 73 is then entered into a database 76. The analyzed data 73 in the database 76 is then accessible and can be requested 79 and sent to multiple review stations 82 anywhere in the world via the internet or other communications system 58 for further analysis and review by clinicians, technicians, researchers, doctors and the like. Signal 84 is a command signal for adjusting a parameter of the treatment device. For example the signal 84 could instruct the PAP device to increase the pressure delivered to the subject. The communications systems used for data transmission need not be the same at all stages. For example, the a cellular network can be used to transmit data between the subject's home 52 and the remote analysis server 70. Then the internet can be used to transmit data between the remote analysis server 70 and the database 76. Finally in this example, a LAN can be used to transmit data between the database 76 and a review station 82.

FIG. 9 shows a diagram outlining the wireless data acquisition system in more detail. In FIG. 9, a patient interface box 85 receives signal (not shown) from a sensor 91. This sensor 91 can be an EEG electrode (as shown) or any of the other sensors described herein or known in the art. Although one type of sensor 91 is shown, the patient interface box 85 is capable of accepting multiple signals from multiple sensors 91. In a very simple embodiment of the present invention, the patient interface box 85 generates a wireless signal 94 encoded with data corresponding to the signal from the sensor 91. The patient interface box 85 transmits the wireless signal 94 to base station 97. In FIG. 9, the wireless signal 94 is shown as radio frequency (RF). In this case, the patient interface box 85 generates a radio frequency signal 94 by frequency modulating a frequency carrier and transmits the radio frequency signal through module antenna 100. The base station 97 receives the radio frequency signal 94 through base antenna 103, demodulates the radio frequency signal 94, and decodes the data. It is understood that other wireless means can be utilized with the present invention, such as infrared and optical, for example. RF wireless transmission is preferred. Although one module antenna 100 and one base antenna 103 are shown in this embodiment, it is understood that two or more types of antennas can be used and are included in the present invention. An external programming means 106, shown in FIG. 9 as a personal computer, contains software that is used to program the patient interface box 85 and the base station 97 through data interface cable 109. The data interface cable 109 is connected to the base station 97 by connector 112. Instead of a data interface cable 109, the patient interface box 85 and the base station 97 can be programmed by radio frequency (or other type) of signals transmitted between an external programming means 106 and a base station 97 and the patient interface box 85 or to another base station 97. RF signals, therefore, can be both transmitted and received by both patient interface box 85 and base station 97. In this event the patient interface box 85 also includes a module receiver 133 (shown on FIG. 2) while the base station 97 also includes a base transmitter 84, in effect making both the patient interface box 85 and the base station 97 into transceivers. In addition, the data interface cable 109 also can be used to convey data from the base station 97 to the external programming means 106. If a personal computer is the external programming means 106, it can monitor, analyze, and display the data in addition to its programming functions. The base receiver 80 and module receiver 133 (shown on FIG. 5) can be any appropriate receivers, such as direct or single conversion types. The base receiver 80 preferably is a double conversion superheterodyne receiver while the module receiver 133 (shown on FIG. 5) preferably is a single conversion receiver. Advantageously, the receiver employed will have automatic frequency control to facilitate accurate and consistent tuning of the radio frequency signal 94 received thereby.

Figure 11:
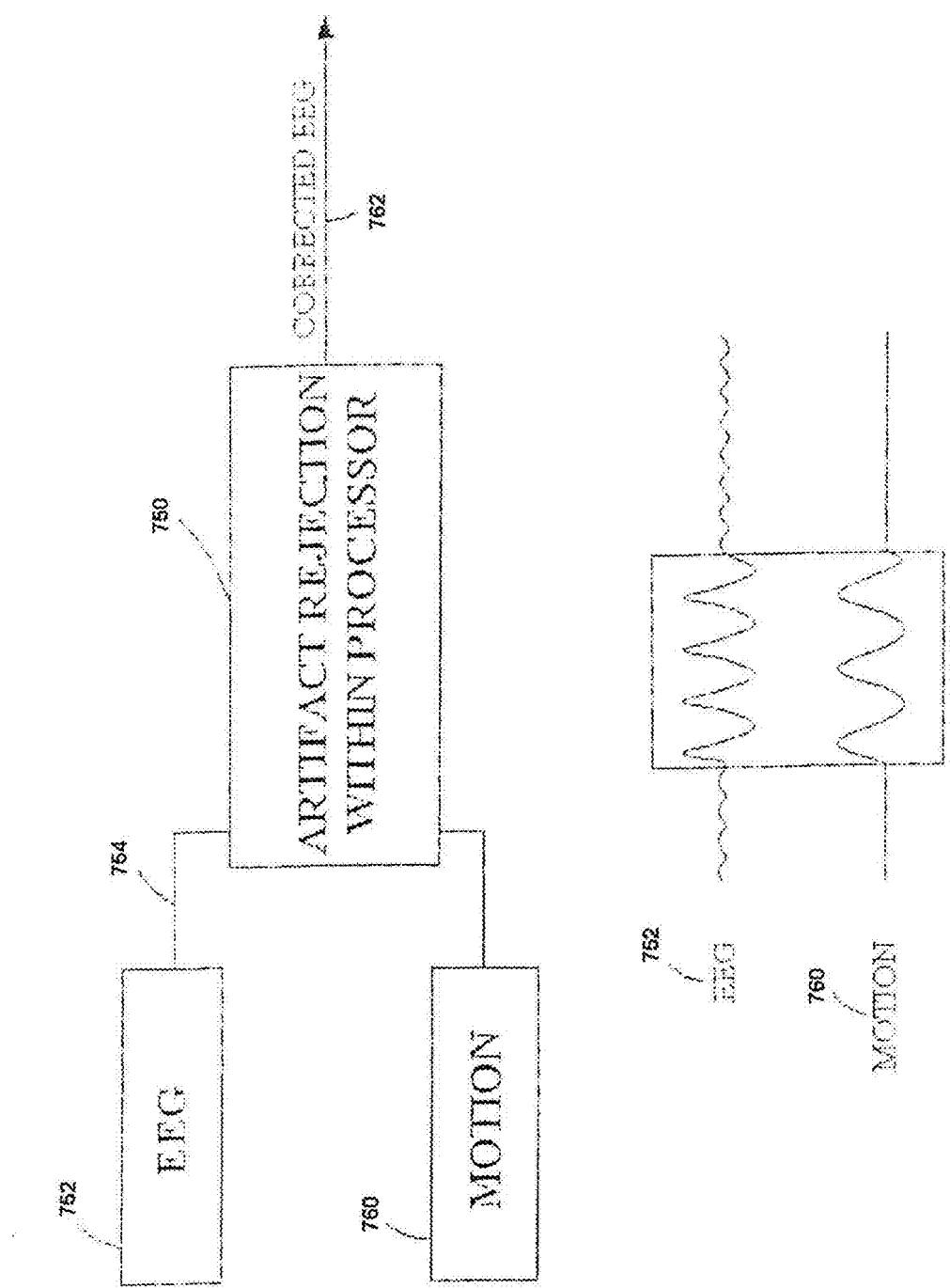
FIG. 11 Block diagram of one embodiment of the present invention showing the motion artifact rejection process.

FIG. 11 is a diagram of an artifact rejection module 750 that can be used in either the data acquisition system (not shown) or a computer or processor (not shown) linked to the data acquisition unit of the present invention. In FIG. 11, a subject's EEG signal 752 is preferably continuously fed 754 into artifact rejection algorithms within the data acquisition unit processor. Simultaneously sensor signals 760 from the subject's movement or motion are also fed into the artifact rejection processor so the EEG signal can be corrected 762 for effects of abnormal or prejudicial motion by the subject. The sensors for determining the subject's motion are described above, but the most preferred is an accelerometer that is incorporated into the EEG data acquisition unit itself.

A method for the detection and treatment of disordered breathing during sleep employing wavelet analysis is provided in which data related to respiratory patterns are analyzed with wavelet analysis. Thus allowing for automatic continuous titration and adjustment of PAP and other treatment module therapy.

More specifically, this method according to one embodiment of the present invention comprises the following steps: placing a mask with a tube over a subject's airway, the mask being in communication with a source of a pressurized breathing gas controlled by a PAP, thereby establishing a respiratory circuit; periodically sampling the gas flow in the circuit; periodically sampling one or several other parameters related to the subjects physiological state; periodically calculating values for one or several parameters distinctive of a physiological pattern; periodically feeding the parameter values to a processing unit programmed to recognize physiological patterns characteristic of sleep disorders; analyzing the parameter values with wavelet analysis; controlling pressurized breathing gas supply and other treatment modules or devices in response to the output from the processing unit utilizing wavelet analysis.

Each sensor and/or transducer may generate an analog signal representative of variables being monitored. The monitoring means may include means for amplifying and/or performing analog processing on the analog signal. The latter may perform filtering and/or other wave shaping functions. The processed signal may be fed to an analog to digital converter to convert each analog signal to a corresponding digital signal. Each digital signal may be fed to a digital processor such as a microprocessor or microcomputer. The digital processor includes software for deriving subject's respiratory state. The software may include means such as an algorithm for determining from the data a gas pressure value which substantially prevents a deterioration of the respiratory state. Preferably the algorithm utilizes wavelet analysis to detect and correct the respiratory event by changing one or several treatment parameters. The result may be used to control delivery of gas to the subject to cancel out or substantially compensate the effects of a sleeping or breathing disorder. In the event that the disorder is not substantially corrected the software may be adapted to activate delivery of a drug such as albuterol, or ipratropium bromide, or the like. This may circumvent what may otherwise be a fatal or severe asthma attack. Other drugs or substances may be used depending on the subject's special needs. Such as oxygen ($O_2$) or carbon dioxide ($CO_2$) gas could be delivered to the subject. As mentioned earlier these gases can be used to aid in respiration. As oxygen can mitigate or relieve the effects of many apneas, while a dose of carbon dioxide gas can be used to trigger respiratory effort in central and complex apneas. The software may additionally be adapted to determine quantity requirements of the drug, gas or other therapeutic agent. The latter may be based on the subject's history and the extent to which the disorder fails to respond to traditional gas pressure treatment. These drugs and therapeutic agents could be delivered by any means known in the art, but could include nebulizers, pressurized gas delivering, intravenous auto injection, or simply allowing the air to flow over a piece of dry ice to sublimate carbon dioxide into the subject's breathing air.

For a better understanding of the detailed description of the invention, it is necessary to present an overview of the wavelet analysis of the present invention.

The wavelet analysis of the present invention, preferably represents a signal as a weighted sum of shifted and scaled versions of the original mother wavelet, without any loss of information. A single wavelet coefficient is obtained by computing the correlation between the scaled and time shifted version of the mother wavelet and the analyzed part of a signal. For efficient analysis, scales and shifts take discrete values based on powers of two (i.e., the dyadic decomposition). For implementation, filter bank and quadrature mirror filters are utilized for a hierarchical signal decomposition, in which a given signal is decomposed by a series of low- and high-pass filters followed by downsampling at each stage, see FIG. 3. This analysis is referred to as Discrete Wavelet Transform (DWT). The particular structure of the filters is determined by the particular wavelet family used for data analysis and by the conditions imposed for a perfect reconstruction of the original signal.

The approximation is the output of the low-pass filter, while the detail is the output of the high-pass filter. In a dyadic multiresolution analysis, the decomposition process is iterated such that the approximations are successively decomposed. The original signal can be reconstructed from its details and approximation at each stage (e.g., for a 3-level signal decomposition, a signal S can be written as S=A3+D3+D2+D1), see FIG. 13. The decomposition may proceed until the individual details consist of a single sample. The nature of the process generates a set of vectors (for instance $a_3$, $d_3$, $d_2$, and $d_1$ in the three level signal decomposition), containing the corresponding coefficients. These vectors are of different lengths, based on powers of two, see FIG. 14. These coefficients are the projections of the signal onto the mother wavelet at a given scale. They contain signal information at different frequency bands (e.g., $a_3$, $d_3$, $d_2$, and $d_1$) determined by the filter bank frequency response. DWT leads to an octave band signal decomposition that divides the frequency space into the bands of unequal widths based on powers of two, see FIG. 15.

The Stationary Wavelet Transform (SWT) is obtained in a similar fashion, however, the downsampling step is not performed. This leads to a redundant signal decomposition with better potential for statistical analysis. The frequency space division is the same as for DWT, see FIG. 6.

Figure 13:
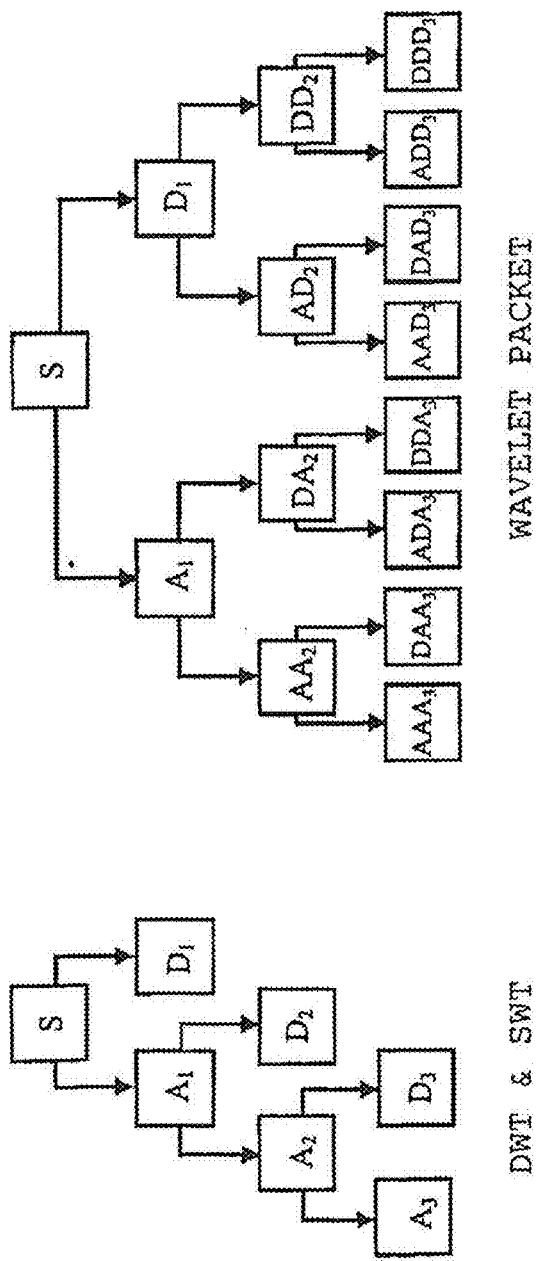
FIG. 13 Analysis tree for Discrete Wavelet Transform (DWT)/Stationary Wavelet Transform (SWT) and wavelet packet decomposition.
Figure 14:
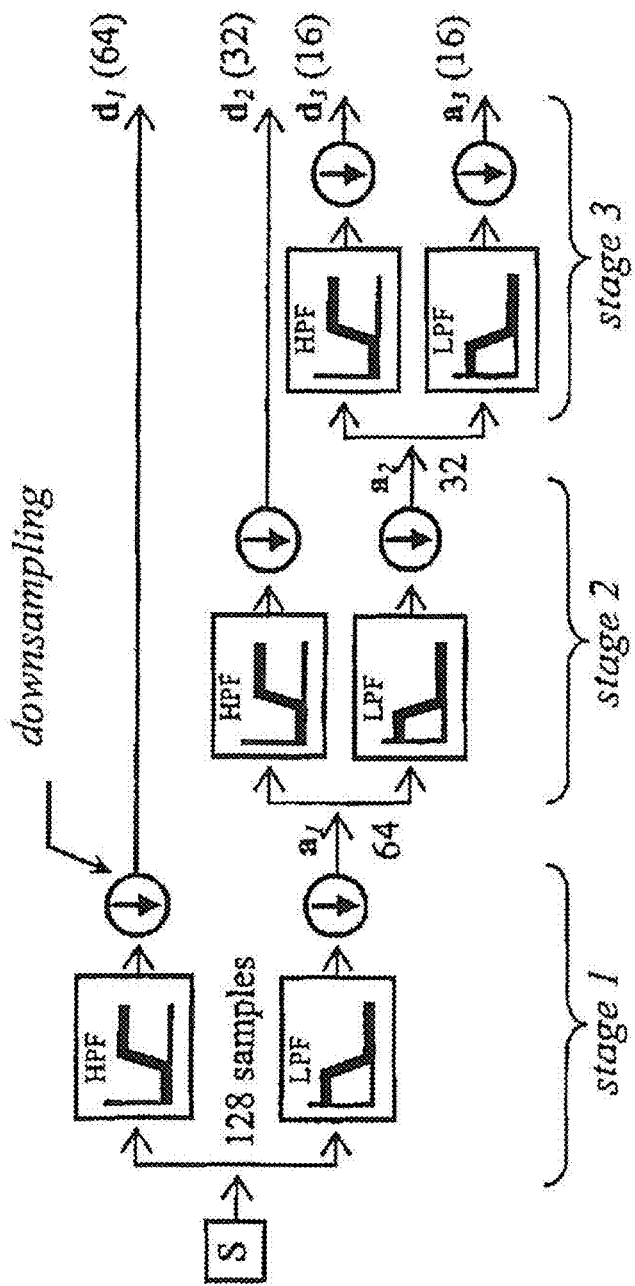
FIG. 14 Schematic diagram illustrating a three-level Discrete Wavelet Transform (DWT) filter bank.
Figure 15:
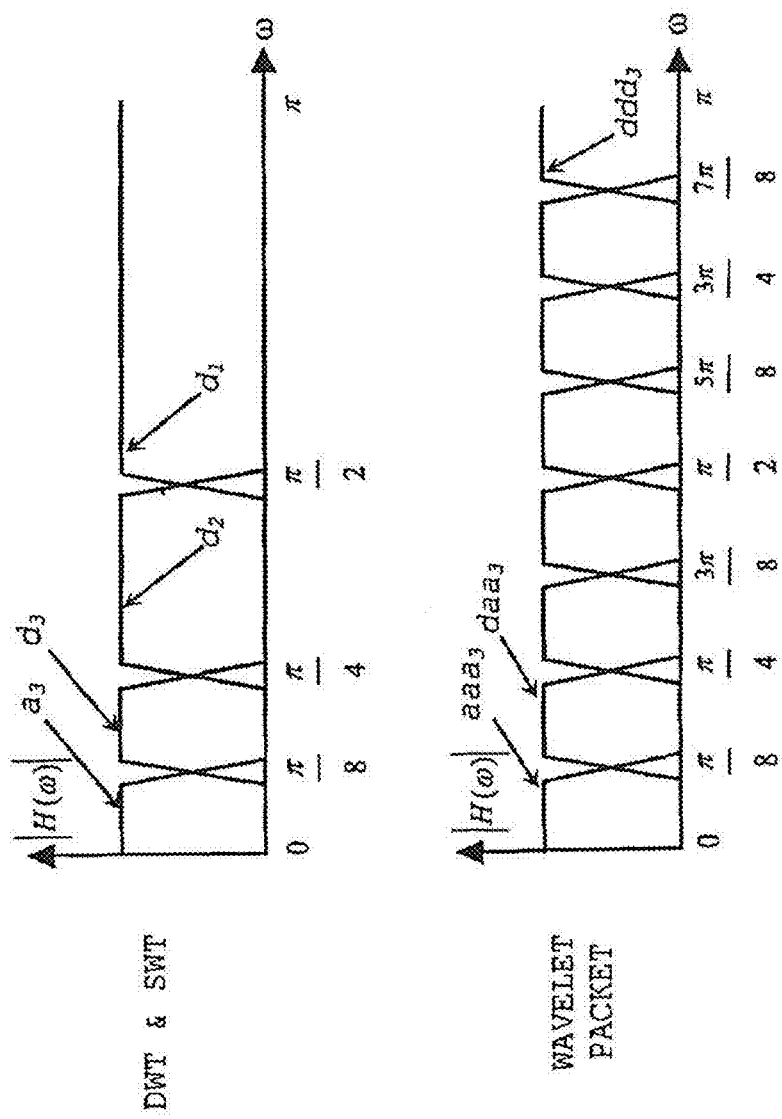
FIG. 15 Illustration of the frequency bands for the analysis trees shown in FIG. 13.

Despite its high efficiency for signal analysis, DWT and SWT decompositions do not provide sufficient flexibility for a narrow frequency bandwidth data analysis (FIG. 13). Wavelet packets, as a generalization of standard DWT, alleviate this problem. At each stage, details as well as approximations are further decomposed into low and high frequency signal components. FIG. 13 shows the wavelet packet decomposition tree. Accordingly, a given signal can be written in a more flexible way than provided by the DWT or SWT decomposition (e.g., at level 3 we have S=A1+AD2+ADD3+DDD3, where DDD3 is the signal component of the narrow high frequency band $ddd_3$). Wavelet packet analysis results in signal decomposition with equal frequency bandwidths at each level of decomposition. This also leads to an equal number of the approximation and details coefficients, a desirable feature for data analysis and information extraction. FIG. 15 illustrates frequency bands for the 3-level wavelet packet decomposition.

Specifically in our application wavelets were adopted due to their suitability for the analysis of non-stationary or transitory features, which characterize most signals found in biomedical applications. Wavelet analysis uses wavelets as basis functions for signal decomposition.

In the present invention the use of wavelet transform significantly reduces the computational complexity when performing the task of assessing the subjects' physiological state based on the acquired signal or signals. Neither a large number of reference signals nor an extensive amount of clinical data is needed to produce the index disclosed herewith.

This invention involves an observed data set acquired in real-time from a subject. This data set is further compared, in real time, with one or more reference data sets which characterize distinct physiological states. The comparison yields an index that is later referred to WAVelet index (abbreviated WAV). The WAVelet index can then be used to assist in distinguishing among the various physiological states, in distinguishing increasing and decreasing rates of respiration, and in distinguishing increasing and decreasing level of both obstructive and central airway apneas, and in distinguishing increasing and decreasing respiratory flow rates and the like.

The observed and reference data sets are statistical representations of the wavelet coefficients obtained by applying a wavelet transform onto corresponding observed and reference signals. These coefficients may be obtained through a wavelet transform of the signal such as standard dyadic discrete wavelet transform (DWT), discrete stationary wavelet transform (SWT), or wavelet packet transform. In this respect, filters yielding coefficients in a frequency band, chosen such that their statistical representation differentiates between respiratory states, can be used for this type of analysis. The choice of this transformation determines the computational complexity of the method and the resolution of the final index. The observed and reference data sets are obtained by calculating a statistical representation of the transformation coefficients.

The reference data sets represent distinct physiological states taken from the continuum from normal (i.e. no irregularities) to full apnea (i.e. complete lack of ventilation). They can be extracted off-line from a group of subjects or subjects. They are then stored for real-time implementation. The transformation selected maximizes the dissimilarity between each of the reference data sets.

The comparison between the observed data set against the reference data sets can be based on the computation of the correlation between these functions. However, a computationally less demanding solution is to quantify the similarity between these functions by computing the L1 (Manhattan), L2 (Euclidean), or any distance metrics. In the preferred embodiment, where two reference data sets are used, the result of this comparison yields two values, each expressing the likelihood of the subject's physiological states are normal or irregular and to what degree. These two values are further combined into a single value corresponding to a univariate index of normal/irregular physiological states state, the WAVelet index. This value corresponds to the type and level of the condition, which is used to create a proper control signal to the gas flow generator, or turbine, or to other treatment modules.

Most any variant of PAP or CPAP therapy, such as bi-level CPAP therapy or therapy in which the mask pressure is modulated within a breath, can also be monitored and/or controlled using the methods described herein. Less complex variants of PAP or CPAP therapy could be used, but the benefits would be much less apparent.

Figure 16:
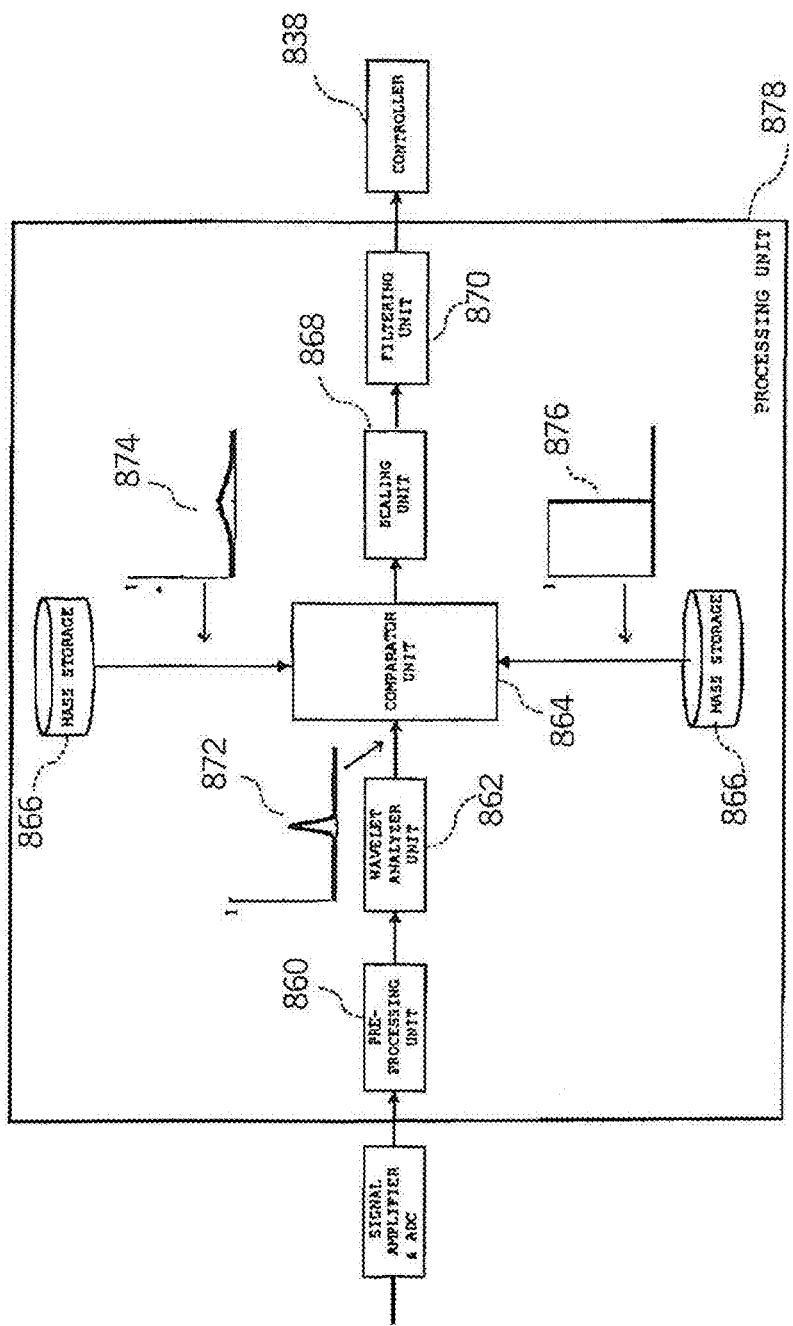
FIG. 16 Schematic diagram of one embodiment of the data acquisition system of the present invention for estimating the physiological state based on wavelet analysis.

The following figures give a more detailed description of example control algorithms of the present invention. This example deals specifically with control of respiratory gas flow using high noise physiological signals, although other treatment parameters can be modified using the same method with proper modification. Also, the respiratory gas flow control and the other treatment methods can be used concurrently to correct the subject's physiological state. Some parts of this example embodiment may not be needed in some applications depending on the level of noise associated with a particular physiological signal. FIG. 16 gives an overview of the wavelet analysis functions of the present invention in its preferred embodiment. The invention is based on the wavelet decomposition of the sensor signals in the wavelet analyzer unit 862. This unit 862 applies the wavelet transform onto the finite signal delivered by the preprocessing unit 860, and then extracts the observed data set 872 correlated to the respiratory state from the corresponding wavelet coefficients. This feature function is further delivered to the comparator unit 864, where it is compared with two reference data sets 874, 876 corresponding to the respiratory state. These reference data sets are calculated off-line and stored in 66 for the real time comparison in the comparator 864. The result of comparison is further integrated into an index of respiration, which is the input of the scaling 868 and filtering 870 units.

Parts of the processing unit 878 contained in the controller 38 that involve signal analysis are detailed in the following.

Pre-Processing Unit

The basic function of the pre-processing unit 80 is to further "clean-up" the signal being analyzed and to reject finite signals that contain artifacts or are corrupted. The exact operation of the preprocessing unit will heavily depend on the type of sensor and physiological parameter being monitored. The following description is supplied to give a simple overview of the basic function of the preprocessing unit and a possible method of implementation.

Figure 12:
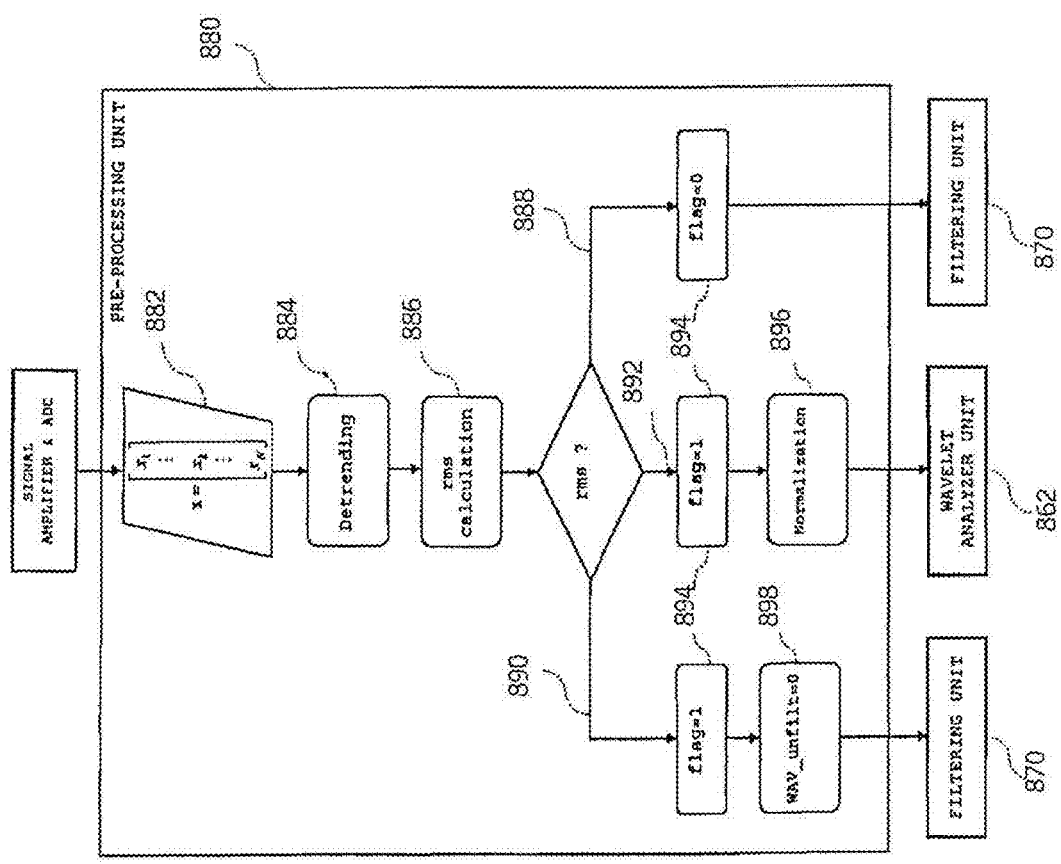
FIG. 12 Flowchart illustrating one preprocessing function of the present invention.

Once a finite signal has been acquired, it is sent to the pre-processing unit, see FIG. 12. It's first stored as a vector x 882 of length N. The mean value $6x\_=k=1N\times k$ is removed 884. The root mean square amplitude 86 of the finite signal is then calculated as:

$$7 \text{ rms}=1Nk=1N(xk)2 \tag{9}$$

Finite signals with amplitudes greater than some maximum value and less than some minimum value are then rejected. It is assumed that they either contain artifacts or the data is corrupted possibly due disconnection of a sensor. If the amplitude is within the two bounds 892, a flag 894 indicating that the finite signal is not corrupted takes the value 1. In this case, the finite signal is normalized 896 as:

$$8\times k=xk \text{ rms}, k=1,N \tag{10}$$

The amplitude normalization allows better focus on the phase and frequency content of the finite signal, rather than its amplitude. So amplitude normalization is especially well suited for bio-potential measurements such as EEG, EMG, or ECG.

If an artifact is present 888, the flag is put to 0 and the algorithm proceeds to the scaling unit 811. If normal breathing is detected 890, the flag takes the value 1 and the variable WAV_unfilt 898 takes the value of 0. The apparatus then proceeds to send the signal to the filtering unit 870. The apparatus then proceeds to the next stage, (i.e. the wavelet analyzer unit denoted by 862 in FIG. 12 and FIG. 16).

Wavelet Analyzer Unit

The wavelet analyzer unit 862 first calculates the wavelet coefficients applying the SWT and the wavelet filter to the pre-processed finite signal. The coefficients are obtained by convolution of the signal with the wavelet filter.

The coefficients corresponding to the band selected in the off-line analysis as the most discriminating (in this embodiment: d, are then stored in a vector C. The probability density function is then obtained by calculating the histogram of the coefficients in vector C. The vector of histogram contains b coefficients, where b is chosen number of bins (e.g. 100). Each element of this vector is then divided by the total number of coefficients in d.sub.1 band, i.e. by the length of a vector C. The result is a vector pdf of length b, which represents the probability density function of wavelet coefficients in d.sub.1 band obtained by the wavelet decomposition of the finite signal x.

Comparator Unit

Figure 17:
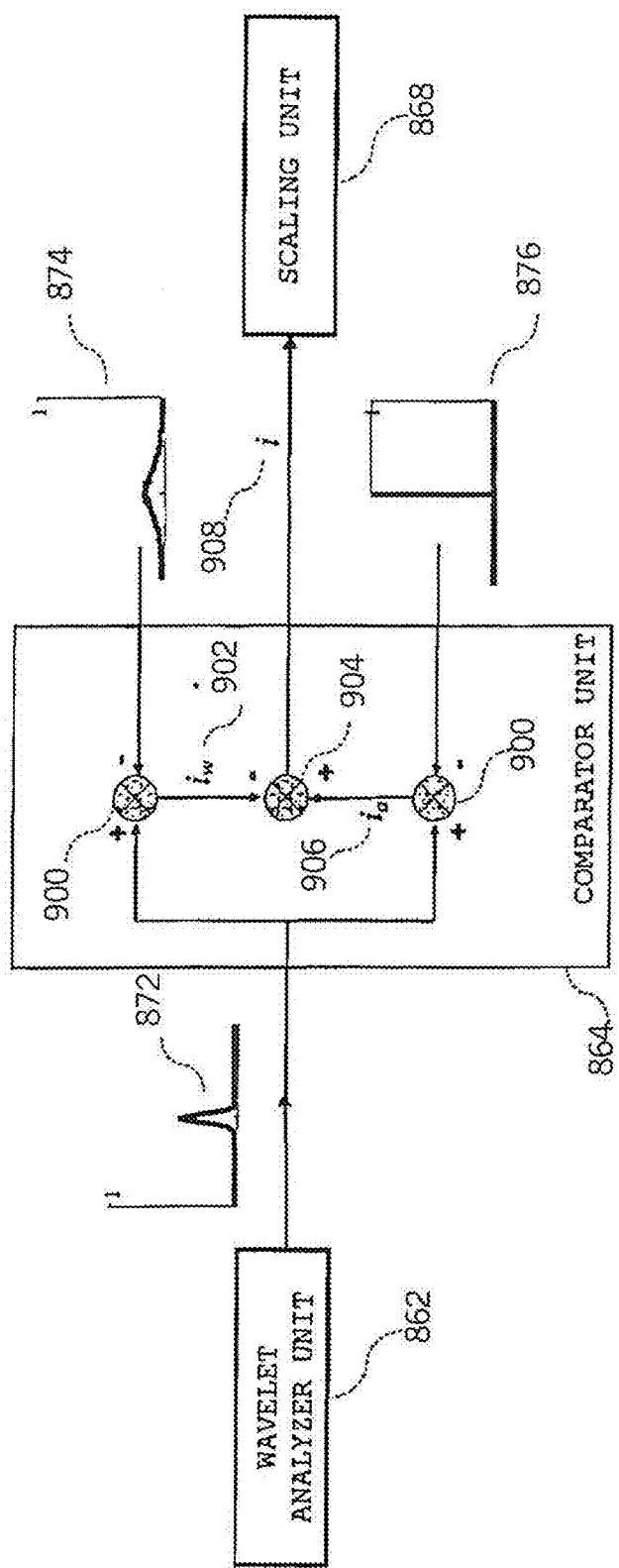
FIG. 17 Schematic diagram illustrating the function of a comparator unit.

The resulting pdf vector is input into comparator unit 864, see FIG. 17. This unit compares the pdf vector of a current signal 872 with two reference vectors pdf.sub.w and pdf.sub.a representing two known respiratory states non-apneic 874 and apneic 876.

The non-apneic reference data set 74 is derived from a combination of signals obtained from a group of healthy subjects (population norming). This reference data set can be then stored on a mass storage device for future real time comparison. Another possibility is to record the subject's respiratory signals while the subject is in a non-apneic state, and then derive the reference data set (self-norming).

The apneic reference data set 876 is the PDF of the wavelet coefficients of an apneic signal, which is either derived or recorded from an actual subject which mimics the most severe level of apneas.

The comparison 900 between the pdf 872 calculated in the wavelet analyzer unit 862 and the two reference data sets pdf.sub.w 874 and pdf.sub.a 876 is achieved using the L1 distance metric. This comparison yields two values i.sub.w 902 and i.sub.a 906.

An index i 908 is then generated by calculating 904 the difference between i.sub.w 902 and i.sub.a 906:

$$i = i.sub.a - i.sub.w \quad (12)$$

The output of the comparator unit is then input to the scaling unit 868.

Scaling Unit

The index i 908 is scaled in order to take values between 0% (corresponding to an apneic signal) and 100% (corresponding to the non-apneic baseline) with higher values indicating higher level of respiratory function:

$$i = i.\text{multidot.scale} + \text{offset} \quad (13)$$

scale and offset are two fixed values calculated in the offline analysis. The result of the scaling is further stored into the variable WAV_unfilt 898.

Filtering Unit

The variable WAV_unfilt 898 contains the unfiltered version of the final WAVelet index. The random character of the some signals dictates that in order to extract a more representative trend of the subject's respiratory state it may be necessary to smooth this variable using a filter.

A new value WAV_unfilt is delivered by the scaling unit 868 for every finite signal (i.e. every second or every fraction of a second in the preferred embodiment). However, note that if the current epoch is corrupted with an artifact, the variable WAV_unfilt can take an arbitrary value, as it will not be used to derive the final value of the index.

The result of the averaging filter is stored in the variable WAV. However, when calculating the average, only uncorrupted finite signals are taken into account by investigating the corresponding flag variable. The WAV variable is finally sent to the controller 838 which then produces the appropriate command signal.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What we claim is:

1. A method of treating a sleep-related breathing disorder comprising steps of:
    attaching a first sensor for collecting data to a subject sleeping at home or at a facility remote from a sleep analysis lab and receiving positive airway pressure (PAP) or continuous positive airway pressure (CPAP) therapy;
    concurrently providing therapy during a first time period to the subject with a PAP or CPAP device while data is being collected from the first sensor;
    connecting, before or after attaching the first sensor to the subject, the first sensor to a data acquisition system, the data acquisition system comprising a data acquisition box, which is separate from the PAP or CPAP device and adapted for receiving a first electrical signal from the first sensor;
    collecting data from the first sensor attached to the subject during the first time period while the subject attempts to sleep;
    collecting data from a second sensor during the first time period, the second sensor which is integrated into the separate PAP or CPAP device from the PAP or CPAP device and transmitting the data from the second sensor to the data acquisition system, the separate PAP or CPAP device adapted for delivering a flow of pressurized gas to the subject; and
    adjusting or titrating the therapy to the subject using at least part of the data from both the first and second sensor signals to improve therapy to the subject during a second time period after the first time period when data is no longer collected.

2. The method of claim 1, wherein the data acquisition box and the PAP or CPAP device each have a wireless RF connection and the data from the second integrated sensor is transmitted wirelessly directly from the PAP or CPAP device to the data acquisition box in real time.

3. The method of claim 1, with the further step wherein the data from the first and second sensors is at least in part transmitted from the data acquisition system by cellular service to a remote data storage station for review remotely by medical personnel, and the medical personnel provides a command signal transmitted by cellular service for titrating or adjusting the PAP or CPAP device automatically if necessary to adjust the flow or by communicating with an individual near the subject or with the subject to adjust the PAP or CPAP device.

4. The method of claim 1, wherein the steps of the method can be used to adjust or titrate the PAP or CPAP device to better identify and distinguish between obstructive, central and complex sleep apneas during the second time period when data is no longer collected from the first sensor.

5. The method of claim 1, wherein the data acquisition system comprises the first and an additional third sensors having signals, the sensors including a respiratory effort belt sensor, and a pulse oximetry sensor; and the second sensor of the PAP or CPAP device is a flow or pressure sensor wherein the PAP or CPAP device is adjusted or titrated using in part data from all three sensors to improve therapy to the subject utilizing the PAP or CPAP after the time period when data is no longer collected from the first and third sensors.

6. The method of claim 1, wherein the separate PAP or CPAP device is automatically titrated or adjusted based on physiological signals that are specific to the subject being treated for improved treatment during the second time period when data is no longer collected from the first sensor.

7. A method of determining the effectiveness of the therapy used in treating a sleep-related breathing disorder comprising steps of:
    attaching a first sensor for collecting data to a subject sleeping at home or at a facility remote from a sleep analysis lab and receiving positive airway pressure (PAP) or continuous positive airway pressure (CPAP) therapy;
    concurrently providing therapy during a first time period to the subject with a PAP or CPAP device while data is being collected from the first sensor;
    connecting, before or after attaching the first sensor to the subject, the first sensor to a data acquisition system, the data acquisition system comprising a data acquisition box, which is separate from the PAP or CPAP device and adapted for receiving a first electrical signal from the first sensor;
    collecting data from the first sensor attached to the subject during the first time period while the subject attempts to sleep;
    collecting data from a second sensor during the first time period, the second sensor which is integrated into the separate PAP or CPAP device from the PAP or CPAP device and transmitting the data from the second sensor to the data acquisition system, the separate PAP or CPAP device adapted for delivering a flow of pressurized gas to the subject;
    determining an effectiveness of the therapy delivered by the separate PAP or CPAP device using at least part of the data from both the first and second sensor signals.

8. The method of claim 7, wherein the data acquisition box and the PAP or CPAP device each have a wireless RF connection and can communicate directly with each other through the wireless connection in real-time.

9. The method of claim 7, wherein the data from the first and second sensors is in part transmitted from both devices in real-time.

10. The method of claim 7, wherein the steps of the method can be used to adjust and titrate the PAP or CPAP device to better identify and distinguish between obstructive, central and complex sleep apneas after the time period when data is no longer collected from the first sensor.

11. The method of claim 7, wherein the separate PAP or CPAP device is automatically titrated or adjusted based on physiological signals from the data acquisition system that are specific to the subject being treated for improved treatment during the second time period when data is no longer collected from the first sensor.

12. The method of claim 7, wherein the PAP or CPAP device is adjusted or titrated by utilizing more robust data collection by relating the data from the first sensor to the second sensor for improved treatment during the second time period when data is no longer collected from the first sensor.

13. The method of claim 7, wherein the data acquisition system comprises an additional third sensor having a signal, the sensors including a respiratory effort belt sensor, and a pulse oximetry sensor; and the second integrated sensor of the PAP or CPAP device is a flow or pressure sensor wherein the PAP or CPAP device is adjusted or titrated using in part data from all three sensors to improve therapy to the subject utilizing the PAP or CPAP after the time period when data is no longer collected from the first and third sensors.

14. The method of claim 13, wherein the data acquisition system comprises an additional fourth sensor for determining body position of the subject.

15. A method of treating a subject's sleep apnea comprising steps of:
    providing a therapy to a subject using a PAP or CPAP device while sleeping, the PAP or CPAP comprising a flow or pressure sensor, and a processor both which are integrated into the PAP or CPAP device;
    collecting data with the PAP or CPAP device from the flow or pressure sensor during a time period of the therapy;
    analyzing with the processor the collected data to determine a quantified level of severity data based on the subject's sleep apnea symptoms during the therapy;
    transmitting, in either order, both 1) the collected data and/or the quantified level of severity data to a cellular phone via a radio frequency wireless link; and 2) the collected data and/or the quantified level of severity data to the remote station from either a) the PAP or CPAP device via a cellular system, or b) the cellular phone to a remote station via the cellular system or the Internet for further analysis with a second processor or a server at the remote station and review of the collected data, the quantified level of severity and/or this analysis by a clinician, technician or physician; and
    further determining the therapy efficacy data with either the processor of the PAP or CPAP device, the second processor or server configured with a second software at the remote station, or the cellular phone using the first software further provided to receive and display the quantified level of severity data and/or therapy efficacy data to the subject or a care provider.

16. The method of claim 15, wherein the cellular phone and the PAP or CPAP device each have a Bluetooth standard wireless RF connection and can communicate directly with each other through the wireless connection in real time.

17. The method of claim 15, wherein the therapy can be modified based in part on the wirelessly transmitted data or information.

18. The method of claim 17, where a rich data set is used to determine treatment from the collected data from multiple nights of treatment.

19. The method of claim 15, wherein the steps of the method can be used to train the PAP or CPAP to adjust or titrate itself to better identify and distinguish between obstructive, central and complex sleep apneas during a second time period with data from the first sensor.

20. The method of claim 15, wherein the therapy can be adjusted or titrated through a wireless connection from the remote location by the technician, clinician or physician.

21. The method of claim 20, wherein the PAP or CPAP is adjusted or titrated in real-time by the technician, clinician or physician from a remote location.

22. The method of claim 15, including the step of storing the collected data, the quantified level of severity data from either the PAP or CPAP device transmitted to the remote station, and/or data based on the transferred data on a database with similar data from treatments of many other subjects.

23. The method of claim 22, wherein the database is stored on a central server or on a group of servers remote to the test location, the central servers or the group of servers upon which the second software is stored on a computer readable medium and executed by the central server or the group of servers.

24. The method of claim 23, including the step of analyzing the data on the database with a relationship algorithm or a neural network to determine an optimal treatment for the subject.

25. The method of claim 23, wherein the PAP or CPAP device, the software on the cellular phone or the remote station determine a total sleep time.

26. The method of claim 23, wherein the processor of the PAP or CPAP device analyzes the collected data, in part, using one or more of a Short-Time Fourier Transform, a Discrete Fourier Transform, a Fast Fourier Transform, a recursively identified system model, a standard deviation technique, a time-frequency signal analysis and/or a Wavelet signal analysis to determine the quantified level of severity data.

27. The method of claim 23, wherein the processor of the PAP or CPAP device analyzes the collected data, in part, using a time-frequency signal analysis to determine the quantified level of severity data.

28. The method of claim 15, wherein the PAP or CPAP further comprises a firmware and/or a third software which along with the first software can be updated from the remote station or a different remote server.

29. The method of claim 15, further comprising the step of alerting the subject's technician, clinician or physician of issues related to the therapy efficacy.

* * * * *